(12) United States Patent
Wrobleski et al.

(10) Patent No.: US 10,308,652 B2
(45) Date of Patent: Jun. 4, 2019

(54) TRICYCLIC HETEROCYCLIC COMPOUNDS USEFUL AS INHIBITORS OF TNF

(71) Applicant: BRISTOL-MYERS SQUIBB COMPANY, Princeton, NJ (US)

(72) Inventors: Stephen T. Wrobleski, Flemington, NJ (US); Gregory D. Brown, Lansdale, PA (US); Shuqun Lin, Newtown, NJ (US); Jingwu Duan, Yardley, PA (US); Zhonghui Lu, King of Prussia, PA (US); Murali T. G. Dhar, Newtown, PA (US); Hai-Yun Xiao, Belle Mead, NJ (US); Andrew J. Tebben, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/558,708

(22) PCT Filed: Mar. 17, 2016

(86) PCT No.: PCT/US2016/022738
§ 371 (c)(1),
(2) Date: Sep. 15, 2017

(87) PCT Pub. No.: WO2016/149437
PCT Pub. Date: Sep. 22, 2016

(65) Prior Publication Data
US 2018/0111937 A1 Apr. 26, 2018

Related U.S. Application Data

(60) Provisional application No. 62/134,779, filed on Mar. 18, 2015.

(51) Int. Cl.
| | |
|---|---|
| C07D 487/14 | (2006.01) |
| C07D 491/147 | (2006.01) |
| A61K 31/5025 | (2006.01) |
| A61P 37/00 | (2006.01) |
| C07D 471/14 | (2006.01) |
| C07D 487/06 | (2006.01) |
| A61P 29/00 | (2006.01) |
| A61P 27/00 | (2006.01) |

(52) U.S. Cl.
CPC ............ C07D 471/14 (2013.01); A61P 29/00 (2018.01); A61P 37/00 (2018.01); C07D 487/06 (2013.01); C07D 487/14 (2013.01); C07D 491/147 (2013.01)

(58) Field of Classification Search
CPC . C07D 487/12; C07D 487/14; C07D 491/147
See application file for complete search history.

(56) References Cited

U.S. PATENT DOCUMENTS

| | | | |
|---|---|---|---|
| 6,894,068 B2 | 5/2005 | Michejda et al. | |
| 9,512,124 B2 | 12/2016 | Alexander et al. | |
| 9,856,253 B2 * | 1/2018 | Breinlinger | .......... C07D 471/04 |
| 2005/0113397 A1 | 5/2005 | Takemura et al. | |
| 2005/0124638 A1 | 6/2005 | Swayze et al. | |
| 2016/0304517 A1 * | 10/2016 | Breinlinger | .......... C07D 471/04 |

FOREIGN PATENT DOCUMENTS

| | | |
|---|---|---|
| CN | 101717397 B | 11/2012 |
| WO | WO 2004/050035 A2 | 6/2004 |
| WO | WO 2009/045174 A1 | 4/2009 |
| WO | WO 2011/119565 A1 | 9/2011 |
| WO | WO 2012/148550 A1 | 11/2012 |
| WO | WO 2012/160030 A1 | 11/2012 |
| WO | WO 2013/186229 A1 | 12/2013 |
| WO | WO 2014/009295 A1 | 1/2014 |
| WO | WO 2014/009296 A1 | 1/2014 |
| WO | WO 2015/086496 A1 | 6/2015 |
| WO | WO 2015/086498 A1 | 6/2015 |
| WO | WO 2015/086500 A1 | 6/2015 |
| WO | WO 2015/086505 A1 | 6/2015 |
| WO | WO 2015/086506 A1 | 6/2015 |
| WO | WO 2015/086507 A1 | 6/2015 |
| WO | WO 2015/086509 A1 | 6/2015 |
| WO | WO 2015/086511 A1 | 6/2015 |
| WO | WO 2015/086512 A1 | 6/2015 |
| WO | WO 2015/086513 A1 | 6/2015 |
| WO | WO 2015/086519 A1 | 6/2015 |
| WO | WO 2015/086523 A1 | 6/2015 |
| WO | WO 2016/149436 A1 | 9/2016 |

(Continued)

OTHER PUBLICATIONS

Priority Document for PCT/EP2015/059687 filed May 4, 2015 for WO 2016177690. (Year: 2015).*
Torres-Castiblanco et al. Biomédica 2018;38: pp. 17-26. (Year: 2018).*
Chaudhary, Vikas, et al., "Scaffold-hopping and hybridization based design and building block strategic synthesis of pyridine-annulated purines: discovery of novel apoptotic anticancer agents", Royal Society of Chemistry, XP-002757555, 2015, vol. 5, pp. 26051-26060.
Chimirri, Alba, et al., "Synthesis and Antitumor Activity of 1H,3H-Thiazolo[3,4-α]benzimidazole Derivatives", Arch. Pharm. Pharm. Med. Chem., 2001, vol. 334, pp. 203-208.
Chimirri, A., et al., "Synthesis and biological activity of novel 1H,3H-thiazolo[3,4-a]benzimidazoles: non-nucleoside human immunodeficiency virus type 1 reverse transcriptase inhibitors", Antiviral Chemistry & Chemotherapy, 1999, vol. 10, pp. 211-217.

(Continued)

*Primary Examiner* — Emily A Bernhardt
(74) *Attorney, Agent, or Firm* — Gary Greenblatt

(57) ABSTRACT

Disclosed are compounds of Formula (I) or a salt thereof, wherein: X is N; W is: —(CR3R3)2-5-, —(CR3R3)x-Y—(CR3R3)y-, —Y—(CR3R3)2-3-Y—, —CR3R3-Y—(CR3R3)2-Y—, —Y—(CR3R3)2-Y—CR3R3-; and Y, R1, R2, R3, R5, R6, R8, x, and y are define herein. Also disclosed are methods of using such compounds as modulators of TNFα, and pharmaceutical compositions comprising such compounds. These compounds are useful in treating inflammatory and autoimmune diseases.

3 Claims, 4 Drawing Sheets

(56) References Cited

FOREIGN PATENT DOCUMENTS

WO     WO 2016/149439 A1     9/2016
WO     WO -2016177690 A1 *   11/2016

OTHER PUBLICATIONS

Meng, Tao, et al., "Synthesis and biological evaluation of 6H-pyrido[2,1:2,3]imidazo[4,5-c]isoquinolin-5(6H)-ones as antimitotic agents and inhibitors of tubulin polymerization", Bioorganic & Medicinal Chemistry, 2014, vol. 22, pp. 848-855.
International Search Report, Application No. PCT/US2016/022738, dated Sep. 19, 2017.

* cited by examiner (II-a)

(II-b)

(II-c)

(III-a)

(III-b)

(III-c)

(III-d)

(IV-a)

(IV-b)

(IV-c)

(IV-d)

(IV-e)

(IV-f)

(V-a)

(V-b)

(V-c)

(V-d)

(V-e)

(V-f)

(V-g)

(V-h)

(V-i)

TRICYCLIC HETEROCYCLIC COMPOUNDS USEFUL AS INHIBITORS OF TNF

CROSS-REFERENCE TO RELATED APPLICATIONS

This application is a national phase application under 35 U.S.C. § 371of International Patent Application No. PCT/US2016/022738, filed Mar. 17, 2016, which claims priority to U.S. Application Ser. No. 62/134779, filed Mar. 18, 2015, which are expressly incorporated fully herein by reference.

DESCRIPTION

The present invention generally relates to tricyclic heterocyclic compounds useful as modulators of TNFα signaling. Provided herein are tricyclic heterocyclic compounds, compositions comprising such compounds, and methods of their use. The invention further pertains to pharmaceutical compositions containing at least one compound according to the invention that are useful for the treatment of conditions related to TNFα activity, including inflammatory and autoimmune disorders.

TNFα is the first and archetypical member of the TNF superfamily (TNFSF) of ligands. TNFSF ligands are involved in the regulation of several key biological processes including cell differentiation, cell survival, cell death, and inflammation. Ligands of the TNF superfamily play a pivotal role in the regulation and orchestration of the immune and inflammatory responses at multiple levels. A common structural feature of TNFSF ligands is the formation of trimeric complexes that can bind to and activate specific TNFSF receptors. Similar to several other family members, TNFα is a type II transmembrane protein that can be secreted as a soluble form following proteolytic cleavage by a metalloprotease. Both the transmembrane and soluble forms of TNFα form biologically active trimeric complexes that signal through TNF receptors 1 and 2. TNFα can act on multiple cell types (T cells, monocytes, endothelial cells) through TNFRs to induce activation of the immune system, production of inflammatory cytokines, osteoclastogenesis, and cell death.

Based on their physiological and pathophysiological functions, TNF and TNFSF ligands are implicated in the pathogenesis of a number of inflammatory and autoimmune disorders (see, for example, Keystone, E. C. et al., *J. Rheumatol.*, 37:27-39 (2010); and Sedger, L. M. et al., *Cytokine Growth Factor Rev.*, 25(4):453-472 (2014)). To date, a number of TNFα modulating agents have been developed and are commercially available. The mechanism of action of clinically-proven protein-based therapeutic agents directed against TNFα is to act as competitive antagonists to inhibit TNFα from binding to $TNFR_1$ and $TNFR_2$. These agents include antibodies specific to TNFα including adalimumab, golimumab, certolizumab pegol, and infliximab. Another approved agent for the treatment of TNFα -mediated disorders is etanercept, a chimera of the immunoglobulin molecule and the $TNFR_2$ ectodomain which also prevents TNFα from binding to the cellular receptors.

Being modulators of human TNFα activity, the tricyclic heterocyclic compounds are beneficial in the treatment and/or prevention of a number of human maladies. These include inflammatory and autoimmune disorders, neurological and neurodegenerative disorders, pain and nociceptive disorders, cardiovascular disorders, metabolic disorders, ocular disorders, and oncological disorders.

WO 2013/186229, WO 2014/009295, and WO 2014/009296 disclose compounds useful as modulators of TNFα.

In view of the numerous conditions that are contemplated to benefit by treatment involving modulation of TNF, it is immediately apparent that new compounds capable of modulating the signaling of TNFα and methods of using these compounds should provide substantial therapeutic benefits to a wide variety of patients.

The present invention relates to a new class of tricyclic heterocyclic compounds found to be effective inhibitors of TNFα activity. These compounds are provided to be useful as pharmaceuticals with desirable stability, bioavailability, therapeutic index, and toxicity values that are important to their drugability.

SUMMARY OF THE INVENTION

The present invention provides compounds of Formula (I) that are useful as inhibitors of TNFα, and are useful for the treatment of inflammatory and autoimmune disorders, neurological and neurodegenerative disorders, cardiovascular disorders, metabolic disorders, ocular disorders, and oncological disorders; or stereoisomers, tautomers, pharmaceutically acceptable salts, solvates or prodrugs thereof.

The present invention also provides pharmaceutical compositions comprising a pharmaceutically acceptable carrier and at least one of the compounds of Formula (I) or stereoisomers, tautomers, pharmaceutically acceptable salts, solvates, or prodrugs thereof.

The present invention also provides a method for modulation of TNFα comprising administering to a host in need of such treatment a therapeutically effective amount of at least one of the compounds of Formula (I) or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of Formula (I) or stereoisomers, tautomers, pharmaceutically acceptable salts, solvates, or prodrugs thereof.

One embodiment provides a method for treating inflammatory and autoimmune diseases. Particular, inflammatory and autoimmune diseases include, but are not limited to, systemic lupus erythematosus, psoriasis, Crohn's disease, ulcerative colitis, asthma, graft versus host disease, allograft rejection, chronic obstructive pulmonary disease, Graves' disease, rheumatoid arthritis, lupus nephritis, cutaneous lupus, ankylosing spondylitis, cryopyrin-associated periodic syndromes (CAPS), TNF receptor associated periodic syndrome (TRAPS), Wegener's granulomatosis, sarcoidosis, familial Mediterranean fever (FMF), adult onset stills, systemic onset juvenile idiopathic arthritis, psoriatic arthritis, multiple sclerosis, neuropathic pain, gout, and gouty arthritis.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of inflammatory and autoimmune diseases.

The present invention also provides a compound of Formula (I) or a pharmaceutical composition in a kit with instructions for using the compound or composition.

The present invention also provides processes and intermediates for making the compounds of the present invention or stereoisomers, tautomers, pharmaceutically acceptable salts, solvates, or prodrugs thereof.

These and other features of the invention will be set forth in the expanded form as the disclosure continues.

BRIEF DESCRIPTION OF THE DRAWINGS

The invention is illustrated by reference to the accompanying drawings described below.

DETAILED DESCRIPTION

Figure 1:
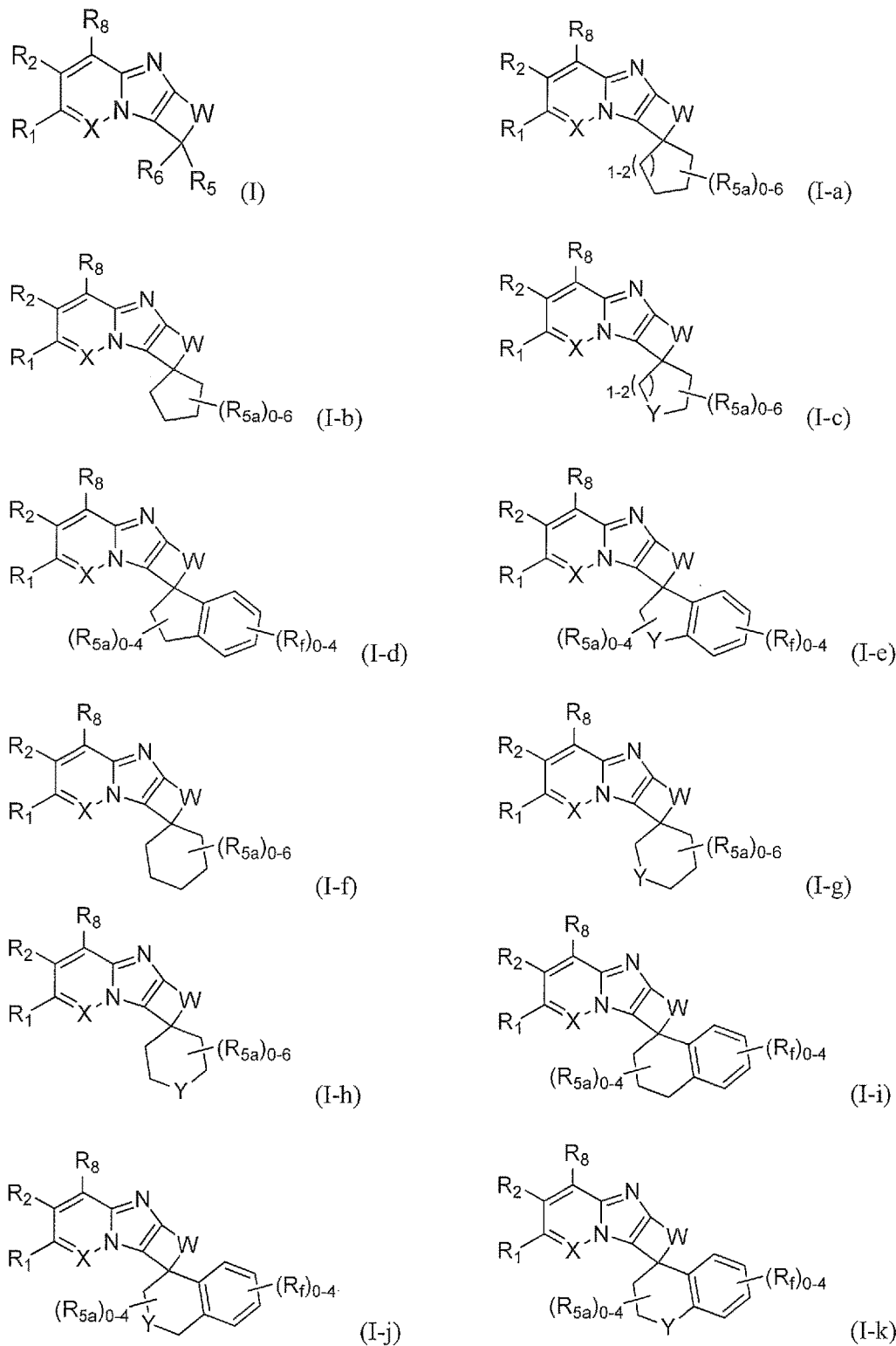
FIG. 1 shows the structures of the compounds of Formula (I), Formula (I-a), Formula (I-b), Formula (I-c), Formula (I-d), Formula (I-e), Formula (I-f), Formula (I-g), Formula (I-h), Formula (I-i), Formula (I-j), and Formula (I-k).
Figure 2:
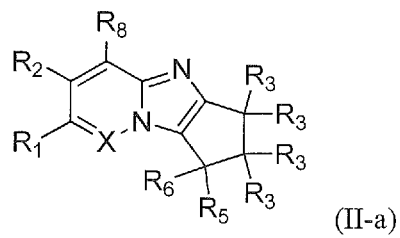
FIG. 2 shows the structures of the compounds of Formula (II-a), Formula (II-b), and Formula (II-c); and the compounds of Formula (III-a), Formula (III-b), Formula (III-c), and Formula (III-d).
Figure 2:
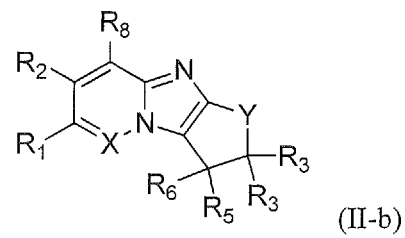
Figure 2:
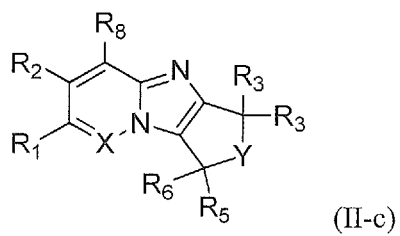
Figure 2:
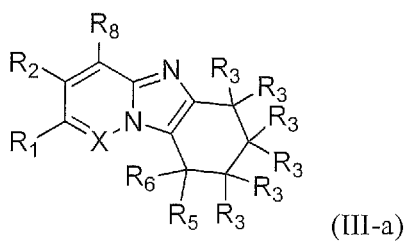
Figure 2:
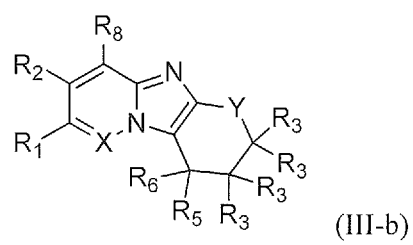
Figure 2:
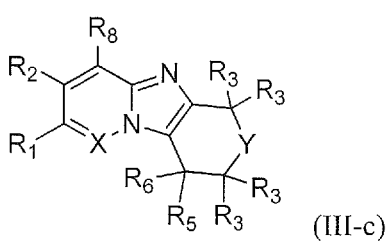
Figure 2:
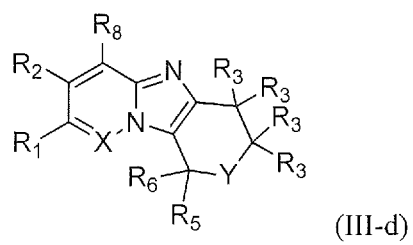
Figure 3:
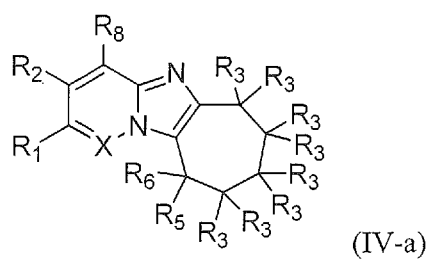
FIG. 3 shows the structures of the compounds of Formula (IV-a), Formula (IV-b), Formula (IV-c), Formula (IV-d), Formula (IV-e), and Formula (IV-f).
Figure 3:
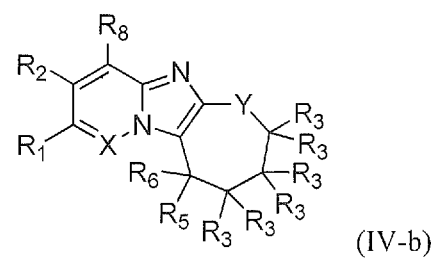
Figure 3:
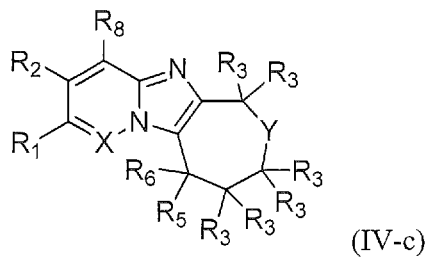
Figure 3:
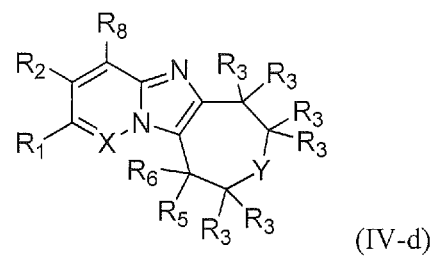
Figure 3:
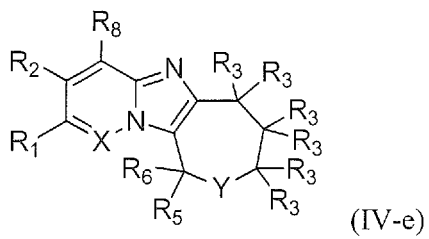
Figure 3:
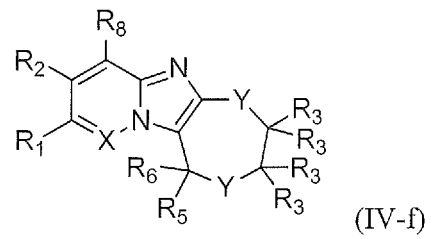
Figure 4:
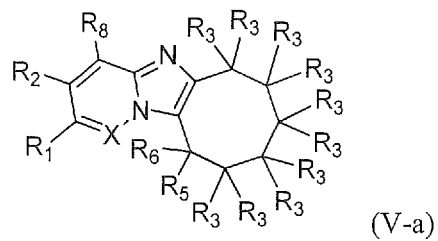
FIG. 4 shows the structures of the compounds of Formula (V-a), Formula (V-b), Formula (V-c), Formula (V-d), Formula (V-e), Formula (V-f), Formula (V-g), Formula (V-h), and Formula (V-i).
Figure 4:
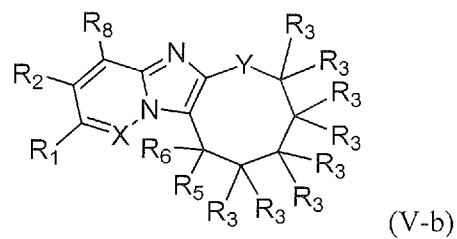
Figure 4:
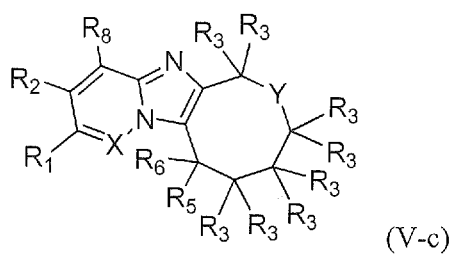
Figure 4:
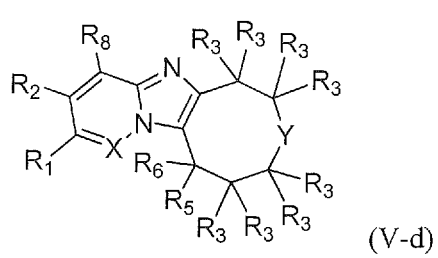
Figure 4:
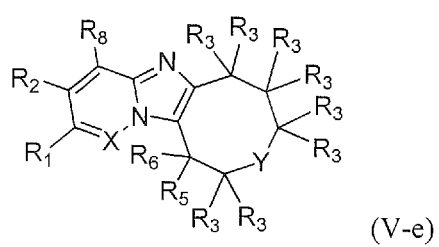
Figure 4:
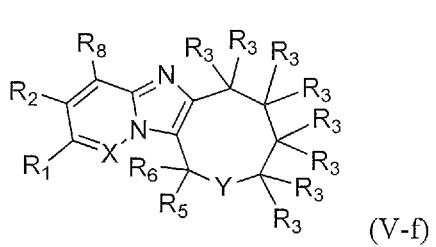
Figure 4:
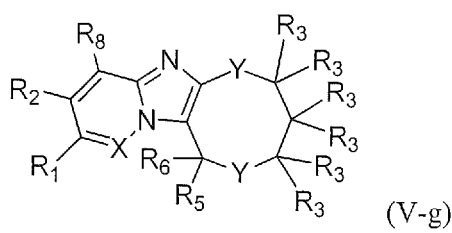
Figure 4:
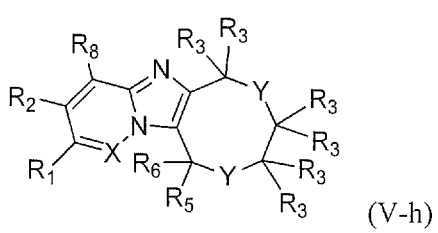
Figure 4:
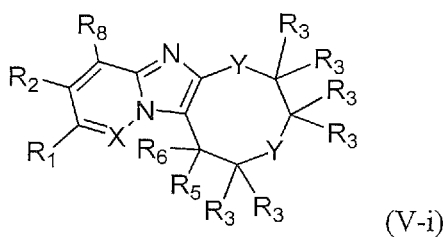

The first aspect of the present invention provides at least one compound of Formula (I)

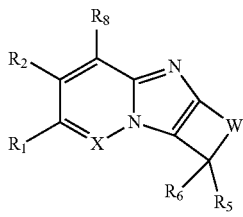

(I)

or a salt thereof, wherein:
X is N;
W is:
  (i) —(CR$_3$R$_3$)$_{2-5}$—;
  (ii) —(CR$_3$R$_3$)$_x$—Y—(CR$_3$R$_3$)$_y$—; or
  (iii)  —Y—(CR$_3$R$_3$)$_{2-3}$—Y—,  —CR$_3$R$_3$—Y—(CR$_3$R$_3$)$_2$—Y—, or —Y—(CR$_3$R$_3$)$_2$—Y—CR$_3$R$_3$—;
each Y is independently O, NR$_4$, or S(O)$_p$;
x is zero, 1, 2, 3, or 4;
y is zero, 1, 2, 3, or 4, provided that (x+y) is 1, 2, 3, or 4;
R$_1$ is H, R$_{1a}$, C$_{1-6}$ haloalkyl, C$_{2-6}$ alkenyl substituted with zero to 6 R$_{1a}$, C$_{2-6}$ alkynyl substituted with zero to 4 R$_{1a}$, —(CR$_g$R$_g$)$_r$(3-14 membered carbocyclyl substituted with zero to 3 R$_{1a}$), —(CR$_g$R$_g$)$_r$(aryl substituted with zero to 3 R$_{1a}$), —(CR$_g$R$_g$)$_r$(5-7 membered heterocyclyl substituted with zero to 3 R$_{1a}$), or —(CR$_g$R$_g$)$_r$(mono- or bicyclic heteroaryl substituted with zero to 3 R$_{1a}$);
R$_2$ is H, halo, —CN, —CF$_3$, —OCF$_3$, —NO$_2$, C$_{1-6}$ alkyl substituted with zero to 6 R$_{1a}$, —(CR$_g$R$_g$)$_r$OR$_e$, —(CR$_g$R$_g$)$_r$NR$_c$R$_c$, —(CR$_g$R$_g$)$_r$S(O)$_p$R$_b$, —(CR$_g$R$_g$)$_r$(3-14 membered carbocyclyl substituted with zero to 3 R$_{1a}$), —(CR$_g$R$_g$)$_r$(aryl substituted with zero to 3 R$_{1a}$), —(CR$_g$R$_g$)$_r$(5-7 membered heterocyclyl substituted with zero to 3 R$_{1a}$), or —(CR$_g$R$_g$)$_r$(monocyclic heteroaryl substituted with zero to 3 R$_{1a}$);
each R$_3$ is independently H, halo, —CN, —OH, —OCF$_3$, C$_{1-6}$ alkyl, C$_{1-6}$ haloalkyl, C$_{2-6}$ alkenyl, C$_{2-6}$ alkynyl, —(CR$_g$R$_g$)$_r$C(O)R$_b$, —(CR$_g$R$_g$)$_r$C(O)OR$_b$, —(CR$_g$R$_g$)$_r$C(O)NR$_c$R$_c$, —(CR$_g$R$_g$)$_r$OR$_e$, —(CR$_g$R$_g$)$_r$OC(O)R$_b$, —(CR$_g$R$_g$)$_r$OC(O)NR$_c$R$_c$, —(CR$_g$R$_g$)$_r$OC(O)OR$_d$, —(CR$_g$R$_g$)$_r$NR$_c$R$_c$, —(CR$_g$R$_g$)$_r$NR$_b$C(O)R$_d$, —(CR$_g$R$_g$)$_r$NR$_b$C(O)OR$_d$, —(CR$_g$R$_g$)$_r$NR$_b$C(O)NR$_c$R$_c$, —(CR$_g$R$_g$)$_r$NR$_b$S(O)$_p$R$_d$, —(CR$_g$R$_g$)$_r$S(O)$_p$R$_b$, —(CR$_g$R$_g$)$_r$S(O)$_p$NR$_c$R$_c$, —(CR$_g$R$_g$)$_r$(3-14 membered carbocyclyl substituted with zero to 3 R$_{1a}$), —(CR$_g$R$_g$)$_r$(aryl substituted with zero to 3 R$_{1a}$), —(CR$_g$R$_g$)$_r$(5-7 membered heterocyclyl substituted with zero to 3 R$_{1a}$), or —(CR$_g$R$_g$)$_r$(mono- or bicyclic heteroaryl substituted with zero to 3 R$_{1a}$); or two R$_3$ along with the carbon atom to which they are attached form C=O, C=NOR$_b$, a spirocarbocyclyl group, or a spiroheterocyclyl group;
each R$_4$ is independently H, C$_{1-6}$ alkyl substituted with zero to 6 R$_{1a}$, C$_{3-7}$ cycloalkyl substituted with zero to 6 R$_{1a}$, —C(O)R$_b$, —C(O)NR$_e$R$_e$, —C(O)OR$_b$, —S(O)$_2$R$_b$, —S(O)$_2$NR$_c$R$_c$, —S(O)$_2$OR$_b$, —(CR$_g$R$_g$)$_r$(3-14 membered carbocyclyl substituted with zero to 3 R$_{1a}$), —(CR$_g$R$_g$)$_r$(aryl substituted with zero to 3 R$_{1a}$), —(CR$_g$R$_g$)$_r$(5-7 membered heterocyclyl substituted with zero to 3 R$_{1a}$), or —(CR$_g$R$_g$)$_r$(monocyclic heteroaryl substituted with zero to 3 R$_{1a}$);
R$_5$ is —(CR$_g$R$_g$)$_r$(3-14 membered carbocyclyl substituted with zero to 3 R$_{1a}$), —(CR$_g$R$_g$)$_r$(aryl substituted with zero to 3 R$_{1a}$), —(CR$_g$R$_g$)$_r$(5-10 membered heterocyclyl substituted with zero to 3 R$_{1a}$), or —(CR$_g$R$_g$)$_r$(mono- or bicyclic heteroaryl substituted with zero to 3 R$_{1a}$);
R$_6$ is H, C$_{1-6}$ alkyl, or C$_{1-6}$ haloalkyl;
R$_6$ is H, C$_{1-6}$ alkyl, or C$_{1-6}$ haloalkyl;
or R$_5$ and R$_6$ together with the carbon atom to which they are attached form a 5- to 6-membered spirocarbocyclyl ring or a spiroheterocyclyl ring, each substituted with zero to 6 R$_{5a}$;
each R$_{5a}$ is independently selected from H, halo, —CN, —OH, C$_{1-3}$ alkyl, C$_{1-3}$ fluoroalkyl, and C$_{1-3}$ alkoxy; or two R$_{5a}$ attached to neighboring carbon atoms of the spirocarbocyclic or the spiroheterocyclic ring, form a benzo ring along with the carbon atoms to which they are attached, said benzo substituted with zero to 4 R$_f$; or two R$_{5a}$ attached to the same carbon atom of the spirocarbocyclic ring or spiroheterocyclic ring, form =O;
R$_8$ is H, halo, —CN, C$_{1-6}$ haloalkyl, or C$_{1-3}$ alkoxy;
each R$_{1a}$ is independently F, Cl, —CN, C$_{1-6}$ alkyl substituted with zero to 6 R$_a$, C$_{3-6}$ cycloalkyl substituted with zero to 6 R$_a$, C$_{1-6}$ alkoxy substituted with zero to 6 R$_a$, C$_{1-3}$ haloalkoxy, heterocycloalkyl substituted with zero to 6 R$_a$, aryl substituted with zero to 6 R$_a$, mono- or bicyclic heteroaryl substituted with zero to 6 R$_a$, —OCH$_2$(aryl substituted with zero to 6 R$_a$), —C(O)R$_b$, —C(O)OR$_b$, —C(O)NR$_c$R$_c$, —OC(O)R$_b$, —OC(O)NR$_c$R$_c$, —OC(O)OR$_d$, —NR$_c$R$_c$, —NR$_b$C(O)R$_d$, —NR$_b$C(O)OR$_d$, —NRbS(O)$_p$R$_d$, —NR$_b$C(O)NR$_c$R$_c$, —NR$_b$S(O)$_p$NR$_c$R$_c$, —S(O)$_p$R$_b$, —S(O)$_p$NR$_c$R$_c$, or —C(O)NR$_b$(CH$_2$)$_{1-3}$NR$_c$R$_c$;
each R$_a$ is independently halo, —CN, —OH, —NO$_2$, —NH$_2$, C$_{1-3}$ alkyl, C$_{1-3}$ fluoroalkyl, C$_{2-4}$ alkenyl, C$_{2-4}$ alkynyl, C$_{1-3}$ alkoxy, C$_{1-3}$ fluoroalkoxy, —C(O)OH, —CH$_2$C(O)OH, —C(O)(C$_{1-3}$ alkyl), —C(O)O(C$_{1-4}$ alkyl), —OC(O)(C$_{1-3}$ alkyl), —NH(C$_{1-3}$ alkyl), —N(C$_{1-3}$ alkyl)$_2$, —C(O)NH(C$_{1-3}$ alkyl), —OC(O)NH(C$_{1-3}$ alkyl), —NHC(O)NH($C_{1-3}$ alkyl), —C(=NH)(NH$_2$), $C_{3-7}$ carbocyclyl, aryl, 5-7 membered heterocyclyl, mono- or bicyclic heteroaryl, —O(aryl), —O(benzyl), —O(heterocyclyl), —S($C_{1-3}$ alkyl), —S(aryl), —S(heterocyclyl), —S(O)(aryl), —S(O)(heterocyclyl), S(O)$_2$(aryl), —S(O)$_2$(heterocyclyl), —NHS(O)$_2$(aryl), —NHS(O)$_2$(heterocyclyl), —NHS(O)$_2$NH(aryl), —NHS(O)$_2$NH(heterocyclyl), —NH(aryl) —NH(heterocyclyl), —NHC(O)(aryl), —NHC(O)($C_{1-3}$ alkyl), —NHC(O)(heterocyclyl), —OC(O)(aryl), —OC(O)(heterocyclyl), —NHC(O)NH(aryl), —NHC(O)NH(heterocyclyl), —OC(O)O($C_{1-3}$ alkyl), —OC(O)O(aryl), —OC(O)O(heterocyclyl), —OC(O)NH(aryl), —OC(O)NH(heterocyclyl), —NHC(O)O(aryl), —NHC(O)O(heterocyclyl), —NHC(O)O($C_{1-3}$ alkyl), —C(O)NH(aryl), —C(O)NH(heterocyclyl), —C(O)O(aryl), —C(O)O(heterocyclyl), —N($C_{1-3}$ alkyl)S(O)$_2$(aryl), —N($C_{1-3}$ alkyl)S(O)$_2$(heterocyclyl), —N($C_{1-3}$ alkyl)S(O)$_2$NH(aryl), —N($C_{1-3}$ alkyl)S(O)$_2$NH(heterocyclyl), —N($C_{1-3}$ alkyl)(aryl), —N($C_{1-3}$ alkyl)(heterocyclyl), —N($C_{1-3}$ alkyl)C(O)(aryl), —N($C_{1-3}$ alkyl)C(O)(heterocyclyl), —N($C_{1-3}$ alkyl)C(O)NH(aryl), —(CH$_2$)$_{0-3}$C(O)NH(heterocyclyl), —OC(O)N($C_{1-3}$ alkyl)(aryl), —OC(O)N($C_{1-3}$ alkyl)(heterocyclyl), —N($C_{1-3}$ alkyl)C(O)O(aryl), alkyl)C(O)O(heterocyclyl), —C(O)N($C_{1-3}$ alkyl)(aryl), —C(O)N($C_{1-3}$ alkyl)(heterocyclyl), —NHS(O)$_2$N($C_{1-3}$ alkyl)(aryl), —NHS(O)$_2$N($C_{1-3}$ alkyl)(heterocyclyl), —NHP(O)$_2$N($C_{1-3}$ alkyl)(aryl), —NHC(O)N($C_{1-3}$ alkyl)(aryl), —NHC(O)N($C_{1-3}$ alkyl)(heterocyclyl), —N($C_{1-3}$ alkyl)S(O)$_2$N($C_{1-3}$ alkyl)(aryl), alkyl)S(O)$_2$N($C_{1-3}$ alkyl)(heterocyclyl), —N($C_{1-3}$ alkyl)C(O)N($C_{1-3}$ alkyl)(aryl), —N($C_{1-3}$ alkyl)C(O)N($C_{1-3}$ alkyl)(heterocyclyl), or —Si($C_{1-3}$ alkyl)$_3$;

each $R_b$ is independently H, $C_{1-6}$ alkyl substituted with zero to 6 $R_f$, $C_{3-7}$ cycloalkyl substituted with zero to 6 $R_f$, heterocycloalkyl substituted with zero to 6 $R_f$, aryl substituted with zero to 3 $R_f$, or mono- or bicyclic heteroaryl substituted with zero to 3 $R_f$;

each $R_c$ is independently H, $C_{1-6}$ alkyl substituted with zero to 6 $R_f$, $C_{3-7}$ cycloalkyl substituted with zero to 6 $R_f$, heterocycloalkyl substituted with zero to 6 $R_f$, aryl substituted with zero to 3 $R_f$, or mono- or bicyclic heteroaryl substituted with zero to 3 $R_f$; or when attached to the same nitrogen, two $R_c$ along with the nitrogen atom to which they are attached form 4-8 membered heterocyclic ring optionally substituted with $R_g$;

each $R_d$ is independently H, $C_{1-6}$ alkyl substituted with zero to 6 $R_f$, $C_{3-7}$ cycloalkyl substituted with zero to 6 $R_f$, heterocycloalkyl substituted with zero to 6 $R_f$, aryl substituted with zero to 3 $R_f$, or mono- or bicyclic heteroaryl substituted with zero to 3 $R_f$;

each $R_e$ is independently H, $C_{1-6}$ alkyl substituted with zero to 6 $R_f$, $C_{1-3}$ haloalkyl, $C_{3-7}$ cycloalkyl substituted with zero to 6 $R_f$, heterocycloalkyl substituted with zero to 6 $R_f$, aryl substituted with zero to 3 $R_f$, or mono- or bicyclic heteroaryl substituted with zero to 3 $R_f$;

each $R_f$ is independently H, halo, —OH, —CN, $C_{1-6}$ alkyl substituted with zero to 6 $R_a$, $C_{1-3}$ alkoxy, $C_{3-7}$ cycloalkyl substituted with zero to 6 $R_a$, heterocycloalkyl substituted with zero to 6 $R_a$, aryl substituted with zero to 3 $R_a$, or mono- or bicyclic heteroaryl substituted with zero to 3 $R_a$;

each $R_g$ is independently H, F, —OH, —CN, $C_{1-3}$ alkyl, —CF$_3$, or phenyl;

each p is independently zero, 1, or 2; and each r is independently zero, 1, 2, 3, or 4.

One embodiment provides a compound of Formula (I) or a salt thereof, wherein W is —(CR$_3$R$_3$)$_2$—; and X, R$_1$, R$_2$, R$_3$, R$_5$, R$_6$, and R$_8$ are defined in the first aspect. Compounds of this embodiment have the structure of compounds of Formula (II-a).

One embodiment provides a compound of Formula (I) or a salt thereof, wherein W is —Y—CR$_3$R$_3$—; and X, Y, R$_1$, R$_2$, R$_3$, R$_5$, R$_6$, and R$_8$ are defined in the first aspect. Compounds of this embodiment have the structure of compounds of Formula (II-b).

One embodiment provides a compound of Formula (I) or a salt thereof, wherein W is —CR$_3$R$_3$-Y—; and X, Y, R$_1$, R$_2$, R$_3$, R$_5$, R$_6$, and R$_8$ are defined in the first aspect. Compounds of this embodiment have the structure of compounds of Formula (II-c).

One embodiment provides a compound of Formula (I) or a salt thereof, wherein W is —Y—CR$_3$R$_3$— or —CR$_3$R$_3$—Y—; and X, Y, R$_1$, R$_2$, R$_3$, R$_5$, R$_6$, and R$_8$ are defined in the first aspect. Compounds of this embodiment have the structure of compounds of Formula (II-b) and Formula (II-c).

One embodiment provides a compound of Formula (I) or a salt thereof, wherein W is —(CR$_3$R$_3$)$_3$—; and X, R$_1$, R$_2$, R$_3$, R$_5$, R$_6$, and R$_8$ are defined in the first aspect. Compounds of this embodiment have the structure of compounds of Formula (III-a).

One embodiment provides a compound of Formula (I) or a salt thereof, wherein W is —Y—(CR$_3$R$_3$)$_2$—; and X, Y, R$_1$, R$_2$, R$_3$, R$_5$, R$_6$, and R$_8$ are defined in the first aspect. Compounds of this embodiment have the structure of compounds of Formula (III-b).

One embodiment provides a compound of Formula (I) or a salt thereof, wherein W is —(CR$_3$R$_3$)—Y—(CR$_3$R$_3$)—; and X, Y, R$_1$, R$_2$, R$_3$, R$_5$, R$_6$, and R$_8$ are defined in the first aspect. Compounds of this embodiment have the structure of compounds of Formula (III-c).

One embodiment provides a compound of Formula (I) or a salt thereof, wherein W is —(CR$_3$R$_3$)$_2$—Y—; and X, Y, R$_1$, R$_2$, R$_3$, R$_5$, R$_6$, and R$_8$ are defined in the first aspect. Compounds of this embodiment have the structure of compounds of Formula (III-d).

One embodiment provides a compound of Formula (I) or a salt thereof, wherein W is —Y—(CR$_3$R$_3$)$_2$—, —(CR$_3$R$_3$)—Y—(CR$_3$R$_3$)—, or —(CR$_3$R$_3$)$_2$—Y—; and X, Y, R$_1$, R$_2$, R$_3$, R$_5$, R$_6$, and R$_8$ are defined in the first aspect. Compounds of this embodiment have the structure of compounds of Formula (III-b), Formula (III-c), and Formula (III-d).

One embodiment provides a compound of Formula (I) or a salt thereof, wherein W is —(CR$_3$R$_3$)$_4$—; and X, Y, R$_1$, R$_2$, R$_3$, R$_5$, R$_6$, and R$_8$ are defined in the first aspect. Compounds of this embodiment have the structure of compounds of Formula (IV-a).

One embodiment provides a compound of Formula (I) or a salt thereof, wherein W is —Y—(CR$_3$R$_3$)$_3$—; and X, Y, R$_1$, R$_2$, R$_3$, R$_5$, R$_6$, and R$_8$ are defined in the first aspect. Compounds of this embodiment have the structure of compounds of Formula (IV-b).

One embodiment provides a compound of Formula (I) or a salt thereof, wherein W is —CR$_3$R$_3$—Y—(CR$_3$R$_3$)$_2$—; and X, Y, R$_1$, R$_2$, R$_3$, R$_5$, R$_6$, and R$_8$ are defined in the first aspect. Compounds of this embodiment have the structure of compounds of Formula (IV-c).

One embodiment provides a compound of Formula (I) or a salt thereof, wherein W is —(CR$_3$R$_3$)$_2$—Y—CR$_3$R$_3$—; and X, Y, R$_1$, R$_2$, R$_3$, R$_5$, R$_6$, and R$_8$ are defined in the first aspect. Compounds of this embodiment have the structure of compounds of Formula (IV-d).

One embodiment provides a compound of Formula (I) or a salt thereof, wherein W is —(CR$_3$R$_3$)$_3$—Y—; and X, Y, $R_1$, $R_2$, $R_3$, $R_5$, $R_6$, and $R_8$ are defined in the first aspect. Compounds of this embodiment have the structure of compounds of Formula (IV-e).

One embodiment provides a compound of Formula (I) or a salt thereof, wherein W is —Y—(CR$_3$R$_3$)$_3$—, —CR$_3$R$_3$—Y—(CR$_3$R$_3$)$_2$—, —(CR$_3$R$_3$)$_2$—Y—CR$_3$R$_3$—, or —(CR$_3$R$_3$)$_3$—Y—; and X, Y, $R_1$, $R_2$, $R_3$, $R_5$, $R_6$, and $R_8$ are defined in the first aspect. Compounds of this embodiment have the structure of compounds of Formula (IV-b), Formula (IV-c), Formula (IV-d), and Formula (IV-e).

One embodiment provides a compound of Formula (I) or a salt thereof, wherein W is —Y—(CR$_3$R$_3$)$_2$—Y—; and X, Y, $R_1$, $R_2$, $R_3$, $R_5$, $R_6$, and $R_8$ are defined in the first aspect. Compounds of this embodiment have the structure of compounds of Formula (IV-f).

One embodiment provides a compound of Formula (I) or a salt thereof, wherein W is —(CR$_3$R$_3$)$_5$—; and X, Y, $R_1$, $R_2$, $R_3$, $R_5$, $R_6$, and $R_8$ are defined in the first aspect. Compounds of this embodiment have the structure of compounds of Formula (V-a).

One embodiment provides a compound of Formula (I) or a salt thereof, wherein W is —Y—(CR$_3$R$_3$)$_4$—; and X, Y, $R_1$, $R_2$, $R_3$, $R_5$, $R_6$, and $R_8$ are defined in the first aspect. Compounds of this embodiment have the structure of compounds of Formula (V-b).

One embodiment provides a compound of Formula (I) or a salt thereof, wherein W is —CR$_3$R$_3$—Y—(CR$_3$R$_3$)$_3$—; and X, Y, $R_1$, $R_2$, $R_3$, $R_5$, $R_6$, and $R_8$ are defined in the first aspect. Compounds of this embodiment have the structure of compounds of Formula (V-c).

One embodiment provides a compound of Formula (I) or a salt thereof, wherein W is —(CR$_3$R$_3$)$_2$—Y—(CR$_3$R$_3$)$_2$—; and X, Y, $R_1$, $R_2$, $R_3$, $R_5$, $R_6$, and $R_8$ are defined in the first aspect. Compounds of this embodiment have the structure of compounds of Formula (V-d).

One embodiment provides a compound of Formula (I) or a salt thereof, wherein W is —(CR$_3$R$_3$)$_3$—Y—CR$_3$R$_3$—; and X, Y, $R_1$, $R_2$, $R_3$, $R_5$, $R_6$, and $R_8$ are defined in the first aspect. Compounds of this embodiment have the structure of compounds of Formula (V-e).

One embodiment provides a compound of Formula (I) or a salt thereof, wherein W is —(CR$_3$R$_3$)$_4$—Y—; and X, Y, $R_1$, $R_2$, $R_3$, $R_5$, $R_6$, and $R_8$ are defined in the first aspect. Compounds of this embodiment have the structure of compounds of Formula (V-f).

One embodiment provides a compound of Formula (I) or a salt thereof, wherein W is —Y—(CR$_3$R$_3$)$_4$—, —CR$_3$R$_3$—Y—(CR$_3$R$_3$)$_3$—, —(CR$_3$R$_3$)$_2$—Y—(CR$_3$R$_3$)$_2$—, —(CR$_3$R$_3$)$_3$—Y—CR$_3$R$_3$—, or —(CR$_3$R$_3$)$_4$—Y—; and X, Y, $R_1$, $R_2$, $R_3$, $R_5$, $R_6$, and $R_8$ are defined in the first aspect. Compounds of this embodiment have the structure of compounds of Formula (V-b), Formula (V-c), Formula (V-d), Formula (V-e), and Formula (V-f).

One embodiment provides a compound of Formula (I) or a salt thereof, wherein W is —Y—(CR$_3$R$_3$)$_3$—Y—; and X, Y, $R_1$, $R_2$, $R_3$, $R_5$, $R_6$, and $R_8$ are defined in the first aspect. Compounds of this embodiment have the structure of compounds of Formula (V-g).

One embodiment provides a compound of Formula (I) or a salt thereof, wherein W is —CR$_3$R$_3$—Y—(CR$_3$R$_3$)$_2$—Y—; and X, Y, $R_1$, $R_2$, $R_3$, $R_5$, $R_6$, and $R_8$ are defined in the first aspect. Compounds of this embodiment have the structure of compounds of Formula (V-h).

One embodiment provides a compound of Formula (I) or a salt thereof, wherein W is —Y—(CR$_3$R$_3$)$_2$—Y—CR$_3$R$_3$—; and X, Y, $R_1$, $R_2$, $R_3$, $R_5$, $R_6$, and $R_8$ are defined in the first aspect. Compounds of this embodiment have the structure of compounds of Formula (V-i).

One embodiment provides a compound of Formula (I) or a salt thereof, wherein W is —(CR$_3$R$_3$)$_{2-5}$—; and X, Y, $R_1$, $R_2$, $R_3$, $R_5$, $R_6$, and $R_8$ are defined in the first aspect. Compounds of this embodiment have the structures of Formula (II-a), Formula (III-a), Formula (IV-a), and Formula (V-a).

One embodiment provides a compound of Formula (I) or a salt thereof, wherein W is —(CR$_3$R$_3$)$_x$—Y—(CR$_3$R$_3$)$_y$—; and X, Y, $R_1$, $R_2$, $R_3$, $R_5$, $R_6$, and $R_8$ are defined in the first aspect. Compounds of this embodiment have the structures of Formula (II-b), Formula (II-c), Formula (III-b), Formula (III-c), Formula (III-d), Formula (IV-b), Formula (IV-c), Formula (IV-d), Formula (IV-e), Formula (V-b), Formula (V-c), Formula (V-d), Formula (V-e), and Formula (V-f).

One embodiment provides a compound of Formula (I) or a salt thereof, wherein W is —Y—(CR$_3$R$_3$)$_{2-3}$—Y—, —CR$_3$R$_3$—Y—(CR$_3$R$_3$)$_2$—Y—, or —Y—(CR$_3$R$_3$)$_2$—Y—CR$_3$R$_3$—; and X, Y, $R_1$, $R_2$, $R_3$, $R_5$, $R_6$, and $R_8$ are defined in the first aspect. Compounds of this embodiment have the structure of Formula (IV-f), Formula (V-g), Formula (V-h), and Formula (V-i).

One embodiment provides a compound of Formula (I) or a salt thereof, wherein W is —(CR$_3$R$_3$)$_2$—, —Y—CR$_3$R$_3$—, or —CR$_3$R$_3$—Y—; and X, Y, $R_1$, $R_2$, $R_3$, $R_5$, $R_6$, and $R_8$ are defined in the first aspect. Included in this embodiment are the compounds of Formula (II-a), Formula (II-b), and Formula (II-c).

One embodiment provides a compound of Formula (I) or a salt thereof, wherein W is —(CR$_3$R$_3$)$_3$—, —Y—(CR$_3$R$_3$)$_2$—, —CR$_3$R$_3$—Y—CR$_3$R$_3$—, or —(CR$_3$R$_3$)$_2$—Y—; and X, Y, $R_1$, $R_2$, $R_3$, $R_5$, $R_6$, and $R_8$ are defined in the first aspect. Included in this embodiment are the compounds of Formula (III-a), Formula (III-b), Formula (III-c), and Formula (III-d).

One embodiment provides a compound of Formula (I) or a salt thereof, wherein W is —(CR$_3$R$_3$)$_4$—, —Y—(CR$_3$R$_3$)$_3$—, —CR$_3$R$_3$—Y—(CR$_3$R$_3$)$_2$—, —(CR$_3$R$_3$)$_2$—Y—CR$_3$R$_3$—, —(CR$_3$R$_3$)$_3$—Y—, or —Y—(CR$_3$R$_3$)$_2$—Y—; and X, Y, $R_1$, $R_2$, $R_3$, $R_5$, $R_6$, and $R_8$ are defined in the first aspect. Included in this embodiment are the compounds of Formula (IV-a), Formula (IV-b), Formula (IV-c), Formula (IV-d), Formula (IV-e), and Formula (IV-f).

One embodiment provides a compound of Formula (I) or a salt thereof, wherein W is —(CR$_3$R$_3$)$_5$—, —Y—(CR$_3$R$_3$)$_4$—, —CR$_3$R$_3$—Y—(CR$_3$R$_3$)$_3$—, —(CR$_3$R$_3$)$_2$—Y—(CR$_3$R$_3$)$_2$—, —(CR$_3$R$_3$)$_3$—Y—CR$_3$R$_3$—, —(CR$_3$R$_3$)$_4$—Y—, —Y—(CR$_3$R$_3$)$_3$—Y—, —CR$_3$R$_3$—Y—(CR$_3$R$_3$)$_2$—Y—, or —Y—(CR$_3$R$_3$)$_2$—Y—CR$_3$R$_3$—; and X, Y, $R_1$, $R_2$, $R_3$, $R_5$, $R_6$, and $R_8$ are defined in the first aspect. Included in this embodiment are the compounds of Formula (V-a), Formula (V-b), Formula (V-c), Formula (V-d), Formula (V-e), Formula (V-f), Formula (V-g), Formula (V-h), and Formula (V-i).

One embodiment provides a compound of Formula (I) or a salt thereof, wherein W is —(CR$_3$R$_3$)$_x$—Y—(CR$_3$R$_3$)$_y$—; Y is O; and X, $R_1$, $R_2$, $R_3$, $R_5$, $R_6$, $R_8$, x, and y are defined in the first aspect. Compounds of this embodiment have the structures of Formula (II-b), Formula (II-c), Formula (III-b), Formula (III-c), Formula (III-d), Formula (IV-b), Formula (IV-c), Formula (IV-d), Formula (IV-e), Formula (V-b), Formula (V-c), Formula (V-d), Formula (V-e), and Formula (V-f).

One embodiment provides a compound of Formula (I) or a salt thereof, wherein W is —(CR$_3$R$_3$)$_x$—Y—(CR$_3$R$_3$)$_y$—; Y is NR$_4$; and X, $R_1$, $R_2$, $R_3$, $R_4$, $R_5$, $R_6$, $R_8$, x, and y are defined in the first aspect. Compounds of this embodiment have the structures of Formula (II-b), Formula (II-c), Formula (III-b), Formula (III-c), Formula (III-d), Formula (IV-b), Formula (IV-c), Formula (IV-d), Formula (IV-e), Formula (V-b), Formula (V-c), Formula (V-d), Formula (V-e), and Formula (V-f).

One embodiment provides a compound of Formula (I) or a salt thereof, wherein W is $-(CR_3R_3)_x-Y-(CR_3R_3)_y-$; Y is $S(O)_p$; and X, $R_1$, $R_2$, $R_3$, $R_5$, $R_6$, $R_8$, p, x, and y are defined in the first aspect. Compounds of this embodiment have the structures of Formula (II-b), Formula (II-c), Formula (III-b), Formula (III-c), Formula (III-d), Formula (IV-b), Formula (IV-c), Formula (IV-d), Formula (IV-e), Formula (V-b), Formula (V-c), Formula (V-d), Formula (V-e), and Formula (V-f).

One embodiment provides a compound of Formula (I) or a salt thereof, wherein W is $-Y-(CR_3R_3)_{2-3}-Y-$, $-CR_3R_3-Y-(CR_3R_3)_2-Y-$, or $-Y-(CR_3R_3)_2-CR_3R_3-$; each Y is O; and X, $R_1$, $R_2$, $R_3$, $R_5$, $R_6$, and $R_8$ are defined in the first aspect. Compounds of this embodiment have the structure of Formula (IV-f), Formula (V-g), Formula (V-h), and Formula (V-i).

One embodiment provides a compound of Formula (I) or a salt thereof, wherein W is $-Y-(CR_3R_3)_{2-3}-Y-$, $-CR_3R_3-Y-(CR_3R_3)_2-Y-$, or $-Y-(CR_3R_3)_2-CR_3R_3-$; each Y is $NR_4$; and X, $R_1$, $R_2$, $R_3$, $R_4$, $R_5$, $R_6$, and $R_8$ are defined in the first aspect. Compounds of this embodiment have the structure of Formula (IV-f), Formula (V-g), Formula (V-h), and Formula (V-i).

One embodiment provides a compound of Formula (I) or a salt thereof, wherein W is $-Y-(CR_3R_3)_{2-3}-Y-$, $-CR_3R_3-Y-(CR_3R_3)_2-Y-$, or $-Y-(CR_3R_3)_2-CR_3R_3-$; each Y is independently O or $NR_4$; and X, $R_1$, $R_2$, $R_3$, $R_4$, $R_5$, $R_6$, and $R_8$ are defined in the first aspect. Compounds of this embodiment have the structure of Formula (IV-f), Formula (V-g), Formula (V-h), and Formula (V-i).

One embodiment provides a compound of Formula (I) or a salt thereof, wherein W is $-Y-(CR_3R_3)_{2-3}-Y-$, $-CR_3R_3-Y-(CR_3R_3)_2-Y-$, or $-Y-(CR_3R_3)_2-CR_3R_3-$; each Y is independently $S(O)_p$; and X, $R_1$, $R_2$, $R_3$, $R_5$, $R_6$, $R_8$, and p are defined in the first aspect. Compounds of this embodiment have the structure of Formula (IV-f), Formula (V-g), Formula (V-h), and Formula (V-i).

One embodiment provides a compound of Formula (I) or a salt thereof, wherein $R_1$ is H, $R_{1a}$, $C_{1-6}$ haloalkyl, $C_{2-6}$ alkenyl substituted with zero to 6 $R_{1a}$, or $C_{2-6}$ alkynyl substituted with zero to 4 $R_{1a}$; and X, W, $R_{1a}$, $R_2$, $R_3$, $R_5$, $R_6$, and $R_8$ are defined in the first aspect.

One embodiment provides a compound of Formula (I) or a salt thereof, wherein $R_1$ is $R_{1a}$; and X, W, $R_{1a}$, $R_2$, $R_3$, $R_5$, $R_6$, and $R_8$ are defined in the first aspect.

One embodiment provides a compound of Formula (I) or a salt thereof, wherein $R_1$ is: F, Cl, Br, or $-CN$; and X, W, $R_{1a}$, $R_2$, $R_3$, $R_5$, $R_6$, and $R_8$ are defined in the first aspect.

One embodiment provides a compound of Formula (I) or a salt thereof, wherein $R_1$ is $C_{1-6}$ haloalkyl, $C_{2-6}$ alkenyl substituted with zero to 6 $R_{1a}$, or $C_{2-6}$ alkynyl substituted with zero to 4 $R_{1a}$; and X, W, $R_{1a}$, $R_2$, $R_3$, $R_5$, $R_6$, and $R_8$ are defined in the first aspect.

One embodiment provides a compound of Formula (I) or a salt thereof, wherein $R_1$ is $-(CR_gR_g)_r$(3-14 membered carbocyclyl substituted with zero to 3 $R_{1a}$), $-(CR_gR_g)_r$(aryl substituted with zero to 3 $R_{1a}$), $-(CR_gR_g)_r$(5-7 membered heterocyclyl substituted with zero to 3 $R_{1a}$), or $-(CR_gR_g)_r$(mono- or bicyclic heteroaryl substituted with zero to 3 $R_{1a}$); and X, W, $R_{1a}$, $R_2$, $R_3$, $R_5$, $R_8$, $R_g$, and r are defined in the first aspect. Included in this embodiment are compounds in which r is 1. Also included in this embodiment are compounds in which $R_1$ is $-CH_2$(3-14 membered carbocyclyl substituted with zero to 3 $R_{1a}$), $-CH_2$(aryl substituted with zero to 3 $R_{1a}$), $-CH_2$(5-7 membered heterocyclyl substituted with zero to 3 $R_{1a}$), or $-CH_2$(mono- or bicyclic heteroaryl substituted with zero to 3 $R_{1a}$).

One embodiment provides a compound of Formula (I) or a salt thereof, wherein $R_1$ is 3-14 membered carbocyclyl substituted with zero to 3 $R_{1a}$, aryl substituted with zero to 3 $R_{1a}$, 5-7 membered heterocyclyl substituted with zero to 3 $R_{1a}$, or mono- or bicyclic heteroaryl substituted with zero to 3 $R_{1a}$; and X, W, $R_{1a}$, $R_2$, $R_3$, $R_5$, $R_6$, and $R_8$ are defined in the first aspect.

One embodiment provides a compound of Formula (I) or a salt thereof, wherein $R_1$ is $-(CR_gR_g)_r$(aryl substituted with zero to 3 $R_{1a}$) or $-(CR_gR_g)_r$(mono- or bicyclic heteroaryl substituted with zero to 3 $R_{1a}$); and X, W, $R_{1a}$, $R_2$, $R_3$, $R_5$, $R_8$, $R_g$, and r are defined in the first aspect. Included in this embodiment are compounds in which r is 1. Also included in this embodiment are compounds in which $R_1$ is $-CH_2$(aryl substituted with zero to 3 $R_{1a}$) or $-CH_2$(mono- or bicyclic heteroaryl substituted with zero to 3 $R_{1a}$).

One embodiment provides a compound of Formula (I) or a salt thereof, wherein $R_1$ is phenyl, pyridinyl, or pyrimidinyl, each substituted 1 to 2 substituents independently selected from Cl, $-CH_3$, $-C(CH_3)_2OH$, $-C(CH_2CH_3)_2OH$, $-C(CH_3)(CH_2CH_3)OH$, $-CH(CH_3)OCH_2CH_3$, $-OCH_3$, $-OCH_2CH_3$, $-OCH_2CH_2CH_3$, $-OCH(CH_3)_2$, $-OCH_2C(CH_3)_3$, $-OCH_2CH(CH_3)_2$, $-OCH_2CH_2OCH_3$, $-OCH_2C(CH_3)_2OH$, $-OCH_2$(methoxyphenyl), $-S(O)_2CH_3$, $-S(O)_2NH_2$, $-S(O)_2NH(CH_3)$, $-C(O)NH_2$, $-C(O)$(morpholinyl), $-C(O)$(methoxyazetidinyl), $-C(O)NH$(cyclopropyl), hydroxycyclopropyl, morpholinyl, and carboxymethyl piperazinyl; and X, W, $R_2$, $R_3$, $R_5$, $R_6$, and $R_8$ are defined in the first aspect.

One embodiment provides a compound of Formula (I) or a salt thereof, wherein $R_1$ is phenyl substituted with 1 to 2 substituents independently selected from Cl, $-CH_3$, $-C(CH_3)_2OH$, $-C(CH_2CH_3)_2OH$, $-C(CH_3)(CH_2CH_3)OH$, $-CH(CH_3)OCH_2CH_3$, $-OCH_3$, $-OCH_2CH_3$, $-OCH_2CH_2CH_3$, $-OCH(CH_3)_2$, $-OCH_2C(CH_3)_3$, $-OCH_2CH(CH_3)_2$, $-OCH_2CH_2OCH_3$, $-OCH_2C(CH_3)_2OH$, $-OCH_2$(methoxyphenyl), $-S(O)_2CH_3$, $-S(O)_2NH_2$, $-S(O)_2NH(CH_3)$, $-C(O)NH_2$, $-C(O)$(morpholinyl), $-C(O)$(methoxyazetidinyl), $-C(O)NH$(cyclopropyl), hydroxycyclopropyl, morpholinyl, and carboxymethyl piperazinyl; and X, W, $R_2$, $R_3$, $R_5$, $R_6$, and $R_8$ are defined in the first aspect. Included in this embodiment are compounds in which $R_1$ is phenyl substituted with 1 to 2 substituents independently selected from Cl, $-C(CH_3)_2OH$, $-C(CH_2CH_3)_2OH$, $-C(CH_3)(CH_2CH_3)OH$, $-CH(CH_3)OCH_2CH_3$, $-OCH_2CH_3$, $-OCH_2CH_2CH_3$, $-OCH(CH_3)_2$, $-OCH_2C(CH_3)_3$, $-OCH_2CH(CH_3)_2$, $-OCH_2CH_2OCH_3$, $-OCH_2C(CH_3)_2OH$, $-OCH_2$(methoxyphenyl), $-S(O)_2CH_3$, $-S(O)_2NH_2$, $-S(O)_2NH(CH_3)$, $-C(O)NH_2$, $-C(O)$(morpholinyl), $-C(O)$(methoxyazetidinyl), $-C(O)NH$(cyclopropyl), hydroxycyclopropyl, and morpholinyl.

One embodiment provides a compound of Formula (I) or a salt thereof, wherein $R_1$ is pyridinyl or pyrimidinyl, each substituted 1 to 2 substituents independently selected from Cl, $-CH_3$, $-C(CH_3)_2OH$, $-C(CH_2CH_3)_2OH$, $-C(CH_3)(CH_2CH_3)OH$, $-CH(CH_3)OCH_2CH_3$, $-OCH_3$, $-OCH_2CH_3$, $-OCH_2CH_2CH_3$, $-OCH(CH_3)_2$, $-OCH_2C(CH_3)_3$, $-OCH_2CH(CH_3)_2$, $-OCH_2CH_2OCH_3$, $-OCH_2C(CH_3)_2OH$, $-OCH_2$(methoxyphenyl), $-S(O)_2CH_3$, $-S(O)_2NH_2$, $-S(O)_2NH(CH_3)$, $-C(O)NH_2$, $-C(O)$(morpholinyl), —C(O)(methoxyazetidinyl), —C(O)NH(cyclopropyl), hydroxycyclopropyl, morpholinyl, and carboxymethyl piperazinyl; and X, W, $R_2$, $R_3$, $R_5$, $R_6$, and $R_8$ are defined in the first aspect. Included in this embodiment are compounds in which $R_1$ is pyridinyl or pyrimidinyl, each substituted a substituent selected from —$CH_3$, —$OCH_3$, —C(O)NH(cyclopropyl), and carboxymethyl piperazinyl.

One embodiment provides a compound of Formula (I) or a salt thereof, wherein $R_2$ is H, halo, —CN, —$CH_3$, —$CF_3$, —$OCF_3$, —$NO_2$, or $C_{1-6}$ alkyl substituted with zero to 6 $R_{1a}$; and X, W, $R_{1a}$, $R_1$, $R_3$, $R_5$, $R_6$, and $R_8$ are defined in the first aspect. Included in this embodiment are compounds in which $R_2$ is H, halo, —CN, —$CH_3$, —$CF_3$, or —$OCF_3$. Also included in this embodiment are compounds in which $R_2$ is H or F.

One embodiment provides a compound of Formula (I) or a salt thereof, wherein $R_2$ is —$(CR_gR_g)_rOR_e$, —$(CR_gR_g)_rNR_cR_c$, —$(CR_gR_g)_rS(O)_pR_b$, —$(CR_gR_g)_r$(3-14 membered carbocyclyl substituted with zero to 3 $R_{1a}$), —$(CR_gR_g)_r$(aryl substituted with zero to 3 $R_{1a}$), —$(CR_gR_g)_r$(5-7 membered heterocyclyl substituted with zero to 3 $R_{1a}$), or —$(CR_gR_g)_r$(monocyclic heteroaryl substituted with zero to 3 $R_{1a}$); and X, W, $R_1$, $R_3$, $R_5$, $R_6$, $R_8$, $R_{1a}$, $R_b$, $R_c$, $R_e$, $R_g$, p, and r are defined in the first aspect. Included in this embodiment are compounds in which r is 1. Also included in this embodiment are compounds in which $R_1$ is —$CH_2$(3-14 membered carbocyclyl substituted with zero to 3 $R_{1a}$), —$CH_2$(aryl substituted with zero to 3 $R_{1a}$), —$CH_2$(5-7 membered heterocyclyl substituted with zero to 3 $R_{1a}$), or —$CH_2$(mono- or bicyclic heteroaryl substituted with zero to 3 $R_{1a}$).

One embodiment provides a compound of Formula (I) or a salt thereof, wherein each $R_3$ is independently H, halo, —CN, —OH, —$OCF_3$, $C_{1-6}$ alkyl, $C_{1-6}$ haloalkyl, $C_{2-6}$ alkenyl, $C_{2-6}$ alkynyl, —$(CR_gR_g)_rC(O)R_b$, —$(CR_gR_g)_rC(O)OR_b$, —$(CR_gR_g)_rC(O)NR_cR_c$, —$(CR_gR_g)_rOR_e$, —$(CR_gR_g)_rOC(O)R_b$, —$(CR_gR_g)_rOC(O)NR_cR_c$, —$(CR_gR_g)_rOC(O)OR_d$, —$(CR_gR_g)_rNR_cR_c$, —$(CR_gR_g)_rNR_bC(O)R_d$, —$(CR_gR_g)_rNR_bC(O)OR_d$, —$(CR_gR_g)_rNR_bC(O)NR_cR_c$, —$(CR_gR_g)_rNR_bS(O)_pR_d$, —$(CR_gR_g)_rS(O)_pR_b$, —$(CR_gR_g)_rS(O)_pNR_cR_c$, —$(CR_gR_g)_r$(3-14 membered carbocyclyl substituted with zero to 3 $R_{1a}$), —$(CR_gR_g)_r$(aryl substituted with zero to 3 $R_{1a}$), —$(CR_gR_g)_r$(5-7 membered heterocyclyl substituted with zero to 3 $R_{1a}$), or —$(CR_gR_g)_r$(mono- or bicyclic heteroaryl substituted with zero to 3 $R_{1a}$); and X, W, $R_1$, $R_2$, $R_5$, $R_6$, $R_8$, $R_{1a}$, $R_b$, $R_c$, $R_d$, $R_e$, $R_g$, p, and r are defined in the first aspect.

One embodiment provides a compound of Formula (I) or a salt thereof, wherein each $R_3$ is independently H, halo, —CN, —OH, —$OCF_3$, $C_{1-6}$ alkyl, $C_{1-6}$ haloalkyl, $C_{2-6}$ alkenyl, or $C_{2-6}$ alkynyl; and X, W, $R_1$, $R_2$, $R_5$, $R_6$, and $R_8$ are defined in the first aspect. Included in this embodiment are compounds in which $R_3$ is H, —OH, —CN, —$OCF_3$, $C_{1-3}$ alkyl, or $C_{1-3}$ fluoroalkyl. Also included in this embodiment are compounds in which $R_3$ is H, —OH, —CN, —$OCF_3$, —$CH_3$, and —$CF_3$.

One embodiment provides a compound of Formula (I) or a salt thereof, wherein each $R_3$ is independently H, —$(CR_gR_g)_rC(O)R_b$, —$(CR_gR_g)_rC(O)OR_b$, —$(CR_gR_g)_rC(O)NR_cR_c$, —$(CR_gR_g)_rOR_e$, —$(CR_gR_g)_rOC(O)R_b$, —$(CR_gR_g)_rOC(O)NR_cR_c$, —$(CR_gR_g)_rOC(O)OR_d$, —$(CR_gR_g)_rNR_cR_c$, —$(CR_gR_g)_rNR_bC(O)R_d$, —$(CR_gR_g)_rNR_bC(O)OR_d$, —$(CR_gR_g)_rNR_bC(O)NR_cR_c$, —$(CR_gR_g)_rNR_bS(O)_pR_d$, —$(CR_gR_g)_rS(O)_pR_b$, or —$(CR_gR_g)_rS(O)_pNR_cR_c$; and X, W, $R_1$, $R_2$, $R_5$, $R_6$, $R_8$, $R_b$, $R_c$, $R_d$, $R_e$, $R_g$, p, and r are defined in the first aspect. Included in this embodiment are compounds in which each $R_g$ is H or —$CH_3$.

One embodiment provides a compound of Formula (I) or a salt thereof, wherein each $R_3$ is independently H, —$(CR_gR_g)_r$(3-14 membered carbocyclyl substituted with zero to 3 $R_{1a}$), —$(CR_gR_g)_r$(aryl substituted with zero to 3 $R_{1a}$), —$(CR_gR_g)_r$(5-7 membered heterocyclyl substituted with zero to 3 $R_{1a}$), or —$(CR_gR_g)_r$(mono- or bicyclic heteroaryl substituted with zero to 3 $R_{1a}$); and X, W, $R_1$, $R_2$, $R_5$, $R_6$, $R_8$, $R_{1a}$, $R_g$, and r are defined in the first aspect.

One embodiment provides a compound of Formula (I) or a salt thereof, wherein each $R_3$ is independently H, halo, —CN, —OH, —$OCF_3$, —$CH_3$, —$CF_3$, or —$(CR_gR_g)_r$(monocyclic heteroaryl substituted with zero to 3 $R_{1a}$); and X, W, $R_1$, $R_2$, $R_5$, $R_6$, $R_8$, $R_{1a}$, $R_g$, and r are defined in the first aspect. Included in this embodiment are compounds in which each $R_3$ is independently H, F, —OH, —$CH_3$, or pyridinyl.

One embodiment provides a compound of Formula (I) or a salt thereof, wherein two $R_3$ along with the carbon atom to which they are attached form C=O, C=$NOR_b$, a spirocarbocyclyl group, or a spiroheterocyclyl group; the remaining $R_3$ are H, —OH, or —$CH_3$; and X, W, $R_1$, $R_2$, $R_5$, $R_6$, $R_8$, and $R_b$ are defined in the first aspect.

One embodiment provides a compound of Formula (I) or a salt thereof, wherein each $R_3$ is independently H, —OH, or —$CH_3$; and X, W, $R_1$, $R_2$, $R_5$ $R_6$, and $R_8$ are defined in the first aspect.

One embodiment provides a compound of Formula (I) or a salt thereof, wherein $R_5$ is —$(CR_gR_g)_r$(3-14 membered carbocyclyl substituted with zero to 3 $R_{1a}$) or —$(CR_gR_g)_r$(aryl substituted with zero to 3 $R_{1a}$); and X, W, $R_1$, $R_{1a}$, $R_2$, $R_3$, $R_4$, $R_6$, $R_5$, $R_g$, and r are defined in the first aspect. Included in this embodiment are compounds in which $R_5$ is —$(CR_gR_g)_r$(aryl substituted with zero to 3 $R_{1a}$). Also included in this embodiment are compounds in which each $R_g$ is H or —OH.

One embodiment provides a compound of Formula (I) or a salt thereof, wherein $R_5$ is —$(CR_gR_g)_r$(phenyl substituted with zero to 3 $R_{1a}$); and X, W, $R_1$, $R_{1a}$, $R_2$, $R_3$, $R_4$, $R_6$, $R_8$, $R_g$, and r are defined in the first aspect. Included in this embodiment are compounds in which $R_5$ is —$(CH_2)_r$(phenyl substituted with zero to 3 $R_{1a}$). Also included in this embodiment are compounds in which $R_5$ is phenyl substituted with zero to 3 $R_{1a}$.

One embodiment provides a compound of Formula (I) or a salt thereof, wherein $R_5$ is phenyl substituted with 1 to 2 substituents independently selected from halo, $C_{1-3}$ alkyl, $C_{1-2}$ fluoroalkyl, $C_{1-2}$ alkoxy, and $C_{1-2}$ fluoroalkoxy; and X, W, $R_1$, $R_2$, $R_3$, $R_4$, $R_6$, and $R_8$ are defined in the first aspect. Included in this embodiment are compounds in which $R_5$ is phenyl substituted with 1 to 2 substituents independently selected from F, Cl, —$CH_3$, —$CH_2CH_3$, —$CF_3$, —$OCH_3$, —$OCHF_2$, and —$OCF_3$.

One embodiment provides a compound of Formula (I) or a salt thereof, wherein $R_5$ is dimethyl phenyl, difluoromethoxyphenyl, trifluoromethoxyphenyl, ethylphenyl, chloro, trifluorophenyl, chloro, methoxyphenyl, chloro, difluoromethylphenyl, fluoro, methoxyphenyl, fluoro, methylphenyl, or fluoro, trifluoromethylphenyl; and W, X, $R_1$, $R_2$, $R_3$, $R_6$, and $R_8$ are defined in the first aspect. Included in this embodiment are compounds in which $R_5$ is:

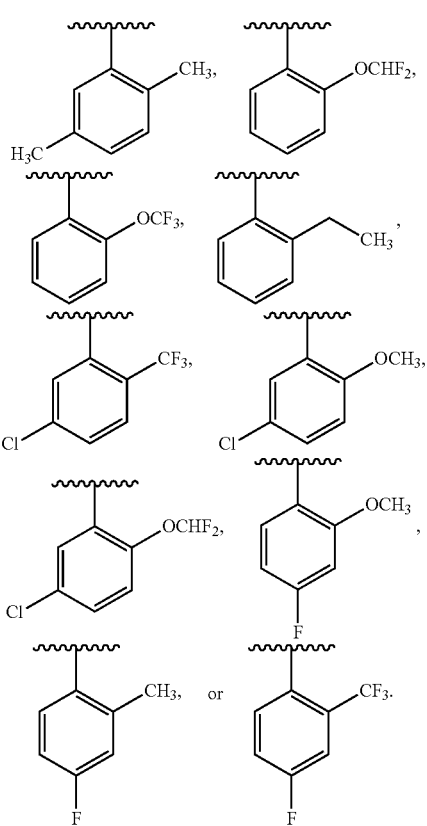

One embodiment provides a compound of Formula (I) or a salt thereof, wherein $R_5$ is $—(CR_gR_g)_r$(5-10 membered heterocyclyl substituted with zero to 3 $R_{1a}$) or $—(CR_gR_g)_r$(mono- or bicyclic heteroaryl substituted with zero to 3 $R_{1a}$); and X, W, $R_1$, $R_{1a}$, $R_2$, $R_3$, $R_4$, $R_6$, $R_8$, $R_g$, and r are defined in the first aspect. Included in this embodiment are compounds in which $R_5$ is $—(CR_gR_g)_r$(mono- or bicyclic heteroaryl substituted with zero to 3 $R_{1a}$). Also included in this embodiment are compounds in which each $R_g$ is H.

One embodiment provides a compound of Formula (I) or a salt thereof, wherein $R_6$ is H or $C_{1-6}$ alkyl; and X, W, $R_1$, $R_2$, $R_3$, $R_5$, and $R_8$ are defined in the first aspect. Included in this embodiment are compounds in which $R_6$ is H or $C_{1-3}$ alkyl. Also included in this embodiment are compounds in which $R_6$ is H or $—CH_3$.

One embodiment provides a compound of Formula (I) or a salt thereof, wherein $R_6$ is H or $C_{1-6}$ haloalkyl; and X, W, $R_1$, $R_2$, $R_3$, $R_5$, and $R_8$ are defined in the first aspect. Included in this embodiment are compounds in which $R_6$ is H or $C_{1-3}$ fluoroalkyl. Also included in this embodiment are compounds in which $R_6$ is H or $—CF_3$.

One embodiment provides a compound of Formula (I) or a salt thereof, wherein $R_6$ is H or $—CH_3$; and X, W, $R_1$, $R_2$, $R_3$, $R_5$, and $R_8$ are defined in the first aspect.

One embodiment provides a compound of Formula (I) or a salt thereof, wherein $R_6$ is H; and X, W, $R_1$, $R_2$, $R_3$, $R_5$, and $R_8$ are defined in the first aspect.

One embodiment provides a compound of Formula (I) or a salt thereof, wherein $R_6$ is $—CH_3$; and X, W, $R_1$, $R_2$, $R_3$, $R_5$, and $R_8$ are defined in the first aspect.

One embodiment provides a compound of Formula (I) or a salt thereof, wherein $R_5$ and $R_6$ together with the carbon atom to which they are attached form a 5- to 6-membered spirocarbocyclic ring or spiroheterocyclic ring, each substituted with zero to 6 $R_{5a}$; and X, W, Y, $R_1$, $R_2$, $R_3$, $R_{5a}$, and $R_8$ are defined in the first aspect. Included in this embodiment are compounds having the structure of Formula (I-a), Formula (I-b), and Formula (I-c), Formula (I-d), Formula (I-e), Formula (I-f), Formula (I-g), Formula (I-h), Formula (I-i), Formula (I-j), and Formula (I-k).

One embodiment provides a compound of Formula (I) or a salt thereof, wherein $R_5$ and $R_6$ together with the carbon atom to which they are attached form a 5- to 6-membered spirocarbocyclic ring substituted with zero to 6 $R_{5a}$; and X, W, $R_1$, $R_2$, $R_3$, $R_{5a}$ and $R_8$ are defined in the first aspect. Included in this embodiment are compounds having the structure of Formula (I-a), Formula (I-b), Formula (I-d), Formula (I-f), and Formula (I-i).

One embodiment provides a compound of Formula (I) or a salt thereof, wherein $R_5$ and $R_6$ together with the carbon atom to which they are attached form a 5- to 6-membered spirocarbocyclic ring substituted with zero to 6 $R_{5a}$, in which two $R_{5a}$ attached to neighboring carbon atoms of the spirocarbocyclic ring form a benzo ring along with the carbon atoms to which they are attached, and said benzo is substituted with zero to 4 $R_f$; and X, W, $R_1$, $R_2$, $R_3$, $R_{5a}$, $R_8$ and $R_f$ are defined in the first aspect. Included in this embodiment are compounds having the structure of Formula (I-d) and Formula (I-i).

One embodiment provides a compound of Formula (I) or a salt thereof, wherein $R_5$ and $R_6$ together with the carbon atom to which they are attached form a 5- to 6-membered spiroheterocyclic ring substituted with zero to 6 $R_{5a}$; and X, W, Y, $R_1$, $R_2$, $R_3$, $R_{5a}$, and $R_8$ are defined in the first aspect. Included in this embodiment are compounds in which the spiroheterocyclic ring includes a heteroatom selected from oxygen or nitrogen. Also included in this embodiment are compounds in which the spiroheterocyclic ring includes an oxygen heteroatom. Included in this embodiment are compounds having the structure of Formula (I-c), Formula (I-e), Formula (I-g), Formula (I-h), Formula (I-j), and Formula (I-k).

One embodiment provides a compound of Formula (I) or a salt thereof, wherein $R_5$ and $R_6$ together with the carbon atom to which they are attached form a 5- to 6-membered spiroheterocyclic ring substituted with zero to 6 $R_{5a}$, in which two $R_{5a}$ attached to neighboring carbon atoms of the spiroheterocyclic ring form a benzo ring along with the carbon atoms to which they are attached, and said benzo is substituted with zero to 4 $R_f$; and X, W, Y, $R_1$, $R_2$, $R_3$, $R_{5a}$, $R_8$, and $R_f$ are defined in the first aspect. Included in this embodiment are compounds in which the spiroheterocyclic ring includes a heteroatom selected from oxygen or nitrogen. Also included in this embodiment are compounds in which the spiroheterocyclic ring includes an oxygen heteroatom. Included in this embodiment are compounds having the structure of Formula (I-e), Formula (I-j), and Formula (I-k).

One embodiment provides a compound of Formula (I) or a salt thereof, wherein $R_8$ is H, halo, or $—CN$; and X, W, $R_1$, $R_2$, $R_3$, $R_5$, and $R_6$ are defined in the first aspect. Included in this embodiment are compounds in which $R_8$ is H, F, Cl, or $—CN$. Also included in this embodiment are compounds in which $R_8$ is H, F, or $—CN$.

One embodiment provides a compound of Formula (I) or a salt thereof, wherein $R_8$ is H, $C_{1-6}$ haloalkyl, or $C_{1-3}$ alkoxy; and X, W, $R_1$, $R_2$, $R_3$, $R_5$, and $R_6$ are defined in the first aspect. Included in this embodiment are compounds in which $R_8$ is H, $C_{1-3}$ haloalkyl, or $C_{1-3}$ alkoxy. Also included in this embodiment are compounds in which $R_8$ is $C_{1-6}$ haloalkyl, or $C_{1-3}$ alkoxy.

One embodiment provides a compound of Formula (I) or a salt thereof, wherein $R_8$ is H, $C_{1-6}$ fluoroalkyl, or $C_{1-3}$ alkoxy; and X, W, $R_1$, $R_2$, $R_3$, $R_5$, and $R_6$ are defined in the first aspect. Included in this embodiment are compounds in which $R_8$ is H, $C_{1-3}$ fluoroalkyl, or $C_{1-3}$ alkoxy. Also included in this embodiment are compounds in which $R_8$ is $C_{1-6}$ fluoroalkyl, or $C_{1-3}$ alkoxy.

One embodiment provides a compound of Formula (I) or a salt thereof, wherein $R_8$ is H, F, Cl, —CN, $C_{1-2}$ fluoroalkyl, or $C_{1-3}$ alkoxy; and X, W, $R_1$, $R_2$, $R_3$, $R_5$, and $R_6$ are defined in the first aspect. Included in this embodiment are compounds in which $R_8$ is H, F, —CN, —$CF_3$, or —$OCH_3$. Also included in this embodiment are compounds in which $R_8$ is H, F, or —$CF_3$.

One embodiment provides a compound of Formula (I-a) or a salt thereof, wherein X, W, $R_1$, $R_2$, $R_3$, $R_{5a}$, and $R_8$ are defined in the first aspect.

One embodiment provides a compound of Formula (I-b) or a salt thereof, wherein X, W, $R_1$, $R_2$, $R_3$, $R_{5a}$, and $R_8$ are defined in the first aspect.

One embodiment provides a compound of Formula (I-c) or a salt thereof, wherein X, W, Y, $R_1$, $R_2$, $R_3$, $R_{5a}$ and $R_8$, are defined in the first aspect.

One embodiment provides a compound of Formula (I-d) or a salt thereof, wherein X, W, $R_1$, $R_2$, $R_3$, $R_{5a}$, $R_8$, and $R_f$ are defined in the first aspect.

One embodiment provides a compound of Formula (I-e) or a salt thereof, wherein X, W, Y, $R_1$, $R_2$, $R_3$, $R_{5a}$, $R_8$, and $R_f$ are defined in the first aspect.

One embodiment provides a compound of Formula (I-f) or a salt thereof, wherein X, W, $R_1$, $R_2$, $R_3$, $R_{5a}$, and $R_8$ are defined in the first aspect.

One embodiment provides a compound of Formula (I-g) or a salt thereof, wherein X, W, Y, $R_1$, $R_2$, $R_3$, $R_{5a}$, and $R_8$ are defined in the first aspect.

One embodiment provides a compound of Formula (I-h) or a salt thereof, wherein X, W, Y, $R_1$, $R_2$, $R_3$, $R_{5a}$, and $R_8$ are defined in the first aspect.

One embodiment provides a compound of Formula (I-i) or a salt thereof, wherein X, W, $R_1$, $R_2$, $R_3$, $R_{5a}$, $R_8$, and $R_f$ are defined in the first aspect.

One embodiment provides a compound of Formula (I-j) or a salt thereof, wherein X, W, Y, $R_1$, $R_2$, $R_3$, $R_{5a}$, $R_8$, and $R_f$ are defined in the first aspect.

One embodiment provides a compound of Formula (I-k) or a salt thereof, wherein X, W, Y, $R_1$, $R_2$, $R_3$, $R_{5a}$, $R_8$, and $R_f$ are defined in the first aspect.

One embodiment provides a compound of Formula (I) or a salt thereof, wherein $R_5$ and $R_6$ together with the carbon atom to which they are attached form a 5- to 6-membered spirocarbocyclic ring substituted with zero to 6 $R_{5a}$, in which two $R_{5a}$ attached to the same carbon atom of the spirocarbocyclic ring or the spiroheterocyclic ring form =O; and X, W, $R_1$, $R_2$, $R_3$, $R_{5a}$ and $R_8$ are defined in the first aspect. Included in this embodiment are compounds of Formula (I-b), Formula (I-c), Formula (I-d), Formula (I-e), Formula (I-f), and Formula (I-g).

One embodiment provides a compound of Formula (I) or a salt thereof, wherein W is —$(CR_3R_3)_2$—; $R_1$ is —$(CR_gR_g)_r$(monocyclic heteroaryl substituted with zero to 3 $R_{1a}$); and X, $R_{1a}$, $R_2$, $R_3$, $R_5$, $R_6$, $R_8$, $R_g$, and r are defined in the first aspect. Included in this embodiment are compounds in which $R_1$ is pyrazolyl, imidazolyl, pyridinyl, pyridazinyl, pyrimidinyl, or pyrazinyl, each substituted with zero to 3 $R_{1a}$). Also included in this embodiment are compounds in which W is —$CH_2CH_2$—; $R_1$ is methoxy-pyridinyl; $R_2$ is H; each $R_3$ is H; and $R_5$ is dimethyl phenyl, difluoromethoxy phenyl, or trifluoromethoxyphenyl.

One embodiment provides a compound of Formula (I) or a salt thereof, wherein W is —$(CR_3R_3)_2$—Y—; Y is $NR_4$; $R_1$ is —$(CR_gR_g)_r$(monocyclic heteroaryl substituted with zero to 3 $R_{1a}$); and X, $R_{1a}$, $R_2$, $R_3$, $R_4$, $R_5$, $R_6$, $R_8$, $R_g$, and r are defined in the first aspect.

Included in this embodiment are compounds in which $R_1$ is pyrazolyl, imidazolyl, pyridinyl, pyridazinyl, pyrimidinyl, or pyrazinyl, each substituted with zero to 3 $R_{1a}$). Also included in this embodiment are compounds in which W is —$CH_2CH_2NH$—; $R_1$ is methoxypyridinyl or hydroxypropyl pyrimidinyl; $R_2$ is H; $R_3$ is H; $R_4$ is H; $R_5$ is difluoromethoxy phenyl or trifluoromethoxyphenyl; and $R_6$ is H or —$CH_3$.

One embodiment provides a compound of Formula (I) or a salt thereof, wherein W is —$(CR_3R_3)_2$—Y—; Y is O; $R_1$ is —$(CR_gR_g)_r$(monocyclic heteroaryl substituted with zero to 3 $R_{1a}$); and X, $R_{1a}$, $R_2$, $R_3$, $R_5$, $R_6$, $R_8$, $R_g$, and r are defined in the first aspect. Included in this embodiment are compounds in which $R_1$ is pyrazolyl, imidazolyl, pyridinyl, pyridazinyl, pyrimidinyl, or pyrazinyl, each substituted with zero to 3 $R_{1a}$). Also included in this embodiment are compounds in which W is —$CH_2CH_2O$—; $R_1$ is pyridinyl or pyrimidinyl, each substituted with —$CH_3$, —$OCH_3$, or —$C(CH_3)_2OH$; $R_2$ is H; $R_3$ is H; and $R_5$ is $R_5$ is dimethyl phenyl or difluoromethoxy phenyl.

One embodiment provides a compound of Formula (I) or a salt thereof, wherein: W is —$CH_2CH_2$—, —$CH_2CH_2O$—, —$CH(OH)CH_2O$—, —$C(CH_3)(OH)CH_2O$—, —$C(OH)$(pyridinyl)$CH_2O$—, —$CH_2CH_2NH$—, —$CHFCH_2NH$—, or —$CH(OH)CH_2NH$—; X is N; $R_1$ is phenyl, pyridinyl, or pyrimidinyl, each substituted 1 to 2 substituents independently selected from Cl, —$CH_3$, —$C(CH_3)_2OH$, —$C(CH_2CH_3)_2OH$, —$C(CH_3)(CH_2CH_3)OH$, —$CH(CH_3)OCH_2CH_3$, —$OCH_3$, —$OCH_2CH_3$, —$OCH_2CH_2CH_3$, —$OCH(CH_3)_2$, —$OCH_2C(CH_3)_3$, —$OCH_2CH(CH_3)_2$, —$OCH_2CH_2OCH_3$, —$OCH_2C(CH_3)_2OH$, —$OCH_2$(methoxyphenyl), —$S(O)_2CH_3$, —$S(O)_2NH_2$, —$S(O)_2NH(CH_3)$, —$C(O)NH_2$, —$C(O)$(morpholinyl), —$C(O)$(methoxyazetidinyl), —$C(O)NH$(cyclopropyl), hydroxycyclopropyl, morpholinyl, and carboxymethyl piperazinyl; $R_2$ is H; $R_5$ is phenyl substituted with 1 to 2 substituents independently selected from F, Cl, —$CH_3$, —$CH_2CH_3$, —$CF_3$, —$OCH_3$, —$OCHF_2$, and —$OCF_3$; $R_6$ is H or —$CH_3$; and $R_8$ is H.

One embodiment provides a compound of Formula (I) or a salt thereof, wherein said compound is: (+/−)-9-(2-(difluoromethoxy)phenyl)-2-(6-methoxypyridin-3-yl)-6,7,8,9-tetrahydropyrido[4',3':4,5]imidazo[1,2-b]pyridazine (1); (+/−)-2-(4-(9-(2-(difluoromethoxy)phenyl)-6,7,8,9-tetrahydropyrido[4',3':4,5]imidazo[1,2-b]pyridazin-2-yl)phenyl)propan-2-ol (2); (+/−)-2-(5-(9-(2-(difluoromethoxy)phenyl)-6,7,8,9-tetrahydropyrido[4',3':4,5]imidazo[1,2-b]pyridazin-2-yl)pyrimidin-2-yl)propan-2-ol (3); (+/−)-cis and trans-9-(2-(difluoromethoxy)phenyl)-2-(4-(2-hydroxypropan-2-yl)phenyl)-6,7,8,9-tetrahydropyrido[4',3':4,5]imidazo[1,2-b]pyridazin-6-ol (4 and 5); cis-(6R,9R)-9-(2-(difluoromethoxy)phenyl)-2-(4-(2-hydroxypropan-2-yl)phenyl)-6,7,8,9-tetrahydropyrido[4',3':4,5]imidazo[1,2-b]pyridazin-6-ol (6); cis-(6S,9S)-9-(2-(difluoromethoxy)phenyl)-2-(4-(2-hydroxypropan-2-yl)phenyl)-6,7,8,9-tetrahydropyrido[4',3':4,5]imidazo[1,2-b]pyridazin-6-ol (7); (+/−)-cis-2-(4-6S,9S)-9-(2-(difluoromethoxy)phenyl)-6-fluoro-6,7,8,9-tetrahydropyrido[4',3':4,5]imidazo[1,2-b]pyridazin-2-yl)phenyl)propan-2-ol (8); (+/−)-trans-2-(4-(9-(2-(difluoromethoxy)phenyl)-6-fluoro-6,7,8,9-tetrahydropyrido[4',3':4,5]imidazo[1,2-b]pyridazin-2-yl)

phenyl)propan-2-ol (9); (+/−)-cis-2-(5-(9-(2-(difluoromethoxy)phenyl)-6-fluoro-6,7,8,9-tetrahydropyrido [4',3':4,5]imidazo[1,2-b]pyridazin-2-yl)pyrimidin-2-yl)propan-2-ol (10); (+/−)-cis-9-(2-(difluoromethoxy)phenyl)-6-fluoro-2-(6-methoxypyridin-3-yl)-6,7,8,9-tetrahydropyrido [4',3':4,5]imidazo[1,2-b]pyridazine (11); cis-(1S,4S)-2-(4-(9-(2-(difluoromethoxy)phenyl)-6-fluoro-6,7,8,9-tetrahydropyrido[4',3':4,5]imidazo[1,2-b]pyridazin-2-yl)phenyl) propan-2-ol (12); cis-(1R,4R)-2-(4-(9-(2-(difluoromethoxy)phenyl)-6-fluoro-6,7,8,9-tetrahydropyrido[4',3':4,5]imidazo[1,2-b]pyridazin-2-yl)phenyl)propan-2-ol (13); trans-(6R,9S)-9-(2-(difluoromethoxy)phenyl)-2-(4-(2-hydroxypropan-2-yl)phenyl)-6,7,8,9-tetrahydropyrido[4',3':4,5]imidazo[1,2-b]pyridazin-6-ol (14); trans-(6S,9R)-9-(2-(difluoromethoxy)phenyl)-2-(4-(2-hydroxypropan-2-yl)phenyl)-6,7,8,9-tetrahydropyrido [4',3':4,5]imidazo[1,2-b]pyridazin-6-ol (15); cis-(6R,9S)-9-(2-(difluoromethoxy)phenyl)-2-(6-methoxypyridin-3-yl)-6,7,8,9-tetrahydropyrido[4',3':4,5]imidazo[1,2-b]pyridazin-6-ol (16); 9-(2-(difluoromethoxy)phenyl)-2-(2-(2-hydroxypropan-2-yl)pyrimidin-5-yl)-6,7,8,9-tetrahydropyrido[4',3':4,5]imidazo[1,2-b]pyridazin-6-ol (17); (4-(9-(2-(difluoromethoxy)phenyl)-6-hydroxy-6,7,8,9-tetrahydropyrido[4',3':4,5]imidazo[1,2-b]pyridazin-2-yl)phenyl)(3-methoxyazetidin-1-yl)methanone (18); (4-(9-(2-(difluoromethoxy)phenyl)-6-hydroxy-6,7,8,9-tetrahydropyrido[4',3':4,5]imidazo[1,2-b]pyridazin-2-yl)phenyl)(morpholino)methanone (19); N-cyclopropyl-4-(9-(2-(difluoromethoxy)phenyl)-6-hydroxy-6,7,8,9-tetrahydropyrido[4',3':4,5]imidazo[1,2-b]pyridazin-2-yl)benzamide (20); N-cyclopropyl-5-(9-(2-(difluoromethoxy)phenyl)-6-hydroxy-6,7,8,9-tetrahydropyrido[4',3':4,5]imidazo[1,2-b]pyridazin-2-yl)picolinamide (21); 2-(4-(5-(9-(2-(difluoromethoxy)phenyl)-6-hydroxy-6,7,8,9-tetrahydropyrido [4',3':4,5]imidazo[1,2-b]pyridazin-2-yl)pyrimidin-2-yl)piperazin-1-yl)acetic acid (22); (+/−)-trans-9-(4-fluoro-2-methoxyphenyl)-2-(4-(2-hydroxypropan-2-yl)phenyl)-6,7,8,9-tetrahydropyrido[4',3':4,5]imidazo[1,2-b]pyridazin-6-ol (23); (+/−)-trans-9-(2-ethylphenyl)-2-(4-(2-hydroxypropan-2-yl)phenyl)-6,7,8,9-tetrahydropyrido [4',3':4,5]imidazo[1,2-b]pyridazin-6-ol (24); (+/−)-cis-9-(2-ethylphenyl)-2-(4-(2-hydroxypropan-2-yl)phenyl)-6,7,8,9-tetrahydropyrido[4',3':4,5]imidazo[1,2-b]pyridazin-6-ol (25); 2-(4-(2-hydroxypropan-2-yl)phenyl)-9-(2-(trifluoromethoxy)phenyl)-6,7,8,9-tetrahydropyrido [4',3':4,5]imidazo[1,2-b]pyridazin-6-ol (26); (+/−)-cis-9-(2-(difluoromethoxy)phenyl)-2-(4-isobutoxyphenyl)-6,7,8,9-tetrahydropyrido[4',3':4,5]imidazo[1,2-b]pyridazin-6-ol (27); (+/−)-trans-9-(5-chloro-2-(difluoromethoxy)phenyl)-2-(4-(2-hydroxypropan-2-yl)phenyl)-6,7,8,9-tetrahydropyrido[4',3':4,5]imidazo[1,2-b]pyridazin-6-ol (28); (+/−)-cis-9-(2-(difluoromethoxy)phenyl)-2-(4-(2-hydroxy-2-methylpropoxy)phenyl)-6,7,8,9-tetrahydropyrido[4',3':4,5]imidazo[1,2-b]pyridazin-6-ol (29); (+/−)-cis-9-(2-(difluoromethoxy)phenyl)-2-(4-(2-hydroxy-2-methylpropoxy)-3-methoxyphenyl)-6,7,8,9-tetrahydropyrido[4',3':4,5]imidazo[1,2-b]pyridazin-6-ol (30); (+/−)-cis-9-(2-(difluoromethoxy)phenyl)-2-(4-ethoxyphenyl)-6,7,8,9-tetrahydropyrido[4',3':4,5]imidazo [1,2-b]pyridazin-6-ol (31); (+/−)-cis-9-(2-(difluoromethoxy)phenyl)-2-(4-isopropoxyphenyl)-6,7,8,9-tetrahydropyrido[4',3':4,5]imidazo[1,2-b]pyridazin-6-ol (32); (+/−)-cis-9-(2-(difluoromethoxy)phenyl)-2-(4-propoxyphenyl)-6,7,8,9-tetrahydropyrido [4',3':4,5]imidazo[1,2-b]pyridazin-6-ol (33); (+/−)-cis-9-(2-(difluoromethoxy)phenyl)-2-(4-(2-methoxyethoxy)phenyl)-6,7,8,9-tetrahydropyrido[4',3':4,5]imidazo[1,2-b]pyridazin-6-ol (34); (+/−)-cis-9-(2-(difluoromethoxy)phenyl)-2-(4-(1-ethoxyethyl)phenyl)-6,7,8,9-tetrahydropyrido[4',3':4,5]imidazo[1,2-b]pyridazin-6-ol (35); (+/−)-cis-9-(2-(difluoromethoxy)phenyl)-2-(4-(1-hydroxycyclopropyl)phenyl)-6,7,8,9-tetrahydropyrido [4',3':4,5]imidazo[1,2-b]pyridazin-6-ol (36); (+/−)-cis-9-(2-(difluoromethoxy)phenyl)-2-(4-((2-methoxybenzyl)oxy)phenyl)-6,7,8,9-tetrahydropyrido[4',3':4,5]imidazo[1,2-b]pyridazin-6-ol (37); (+/−)-trans-9-(4-fluoro-2-methylphenyl)-2-(4-(2-hydroxypropan-2-yl)phenyl)-6,7,8,9-tetrahydropyrido[4',3':4,5]imidazo[1,2-b]pyridazin-6-ol (38); (+/−)-cis-9-(4-fluoro-2-(trifluoromethyl)phenyl)-2-(4-(2-hydroxypropan-2-yl)phenyl)-6,7,8,9-tetrahydropyrido[4',3':4,5]imidazo[1,2-b]pyridazin-6-ol (39); (+/−)-cis-4-(9-(2-(difluoromethoxy)phenyl)-6-hydroxy-6,7,8,9-tetrahydropyrido[4',3':4,5]imidazo[1,2-b]pyridazin-2-yl)-N-methylbenzenesulfonamide (40); (+/−)-cis-9-(2-(difluoromethoxy) phenyl)-2-(4-(methylsulfonyl)phenyl)-6,7,8,9-tetrahydropyrido[4',3':4,5]imidazo[1,2-b]pyridazin-6-ol (41); (+/−)-cis-9-(2-(difluoromethoxy)phenyl)-2-(4-(neopentyloxy) phenyl)-6,7,8,9-tetrahydropyrido[4',3':4,5]imidazo[1,2-b]pyridazin-6-ol (42); (+/−)-cis-9-(4-fluoro-2-methylphenyl)-2-(4-(2-hydroxypropan-2-yl)phenyl)-6,7,8,9-tetrahydropyrido [4',3':4,5]imidazo[1,2-b]pyridazin-6-ol (43); (+/−)-trans-9-(4-fluoro-2-methylphenyl)-2-(4-(2-hydroxypropan-2-yl)phenyl)-6,7,8,9-tetrahydropyrido[4',3':4,5]imidazo[1,2-b]pyridazin-6-ol (44); (+/−)-cis-9-(2-(difluoromethoxy)phenyl)-2-(4-morpholinophenyl)-6,7,8,9-tetrahydropyrido[4',3':4,5]imidazo[1,2-b]pyridazin-6-ol (45); (+/−)-cis-4-(9-(2-(difluoromethoxy)phenyl)-6-hydroxy-6,7,8,9-tetrahydropyrido[4',3':4,5]imidazo[1,2-b]pyridazin-2-yl)benzenesulfonamide (46); (+/−)-cis-(2-chloro-4-(9-(2-(difluoromethoxy) phenyl)-6-hydroxy-6,7,8,9-tetrahydropyrido[4',3':4,5]imidazo[1,2-b]pyridazin-2-yl)phenyl)(morpholino)methanone (47); (+/−)-cis-2-chloro-4-(9-(2-(difluoromethoxy) phenyl)-6-hydroxy-6,7,8,9-tetrahydropyrido[4',3':4,5]imidazo[1,2-b]pyridazin-2-yl)benzamide (48); (+/−)-cis-9-(2-(difluoromethoxy)phenyl)-2-(4-(3-hydroxypentan-3-yl)phenyl)-6,7,8,9-tetrahydropyrido[4',3':4,5]imidazo[1,2-b]pyridazin-6-ol (49); (+/−)-cis-9-(2-(difluoromethoxy)phenyl)-2-(4-(2-hydroxybutan-2-yl)phenyl)-6,7,8,9-tetrahydropyrido[4',3':4,5]imidazo[1,2-b]pyridazin-6-ol (50); (+/−)-trans-9-(2-(difluoromethoxy)phenyl)-2-(6-methoxypyridin-3-yl)-6,7,8,9-tetrahydropyrido[4',3':4,5]imidazo[1,2-b]pyridazin-6-ol (51); (+/−)-trans-9-(2-(difluoromethoxy)phenyl)-2-(4-(2-hydroxy-2-methylpropoxy)phenyl)-6,7,8,9-tetrahydropyrido[4',3':4,5]imidazo[1,2-b]pyridazin-6-ol (52); (+/−)-trans-9-(2,5-dimethylphenyl)-2-(4-(2-hydroxypropan-2-yl)phenyl)-6,7,8,9-tetrahydropyrido[4',3':4,5]imidazo[1,2-b]pyridazin-6-ol (53); (+/−)-cis-9-(5-chloro-2-(difluoromethoxy)phenyl)-2-(4-(2-hydroxypropan-2-yl)phenyl)-6,7,8,9-tetrahydropyrido[4',3':4,5]imidazo[1,2-b]pyridazin-6-ol (54); (+/−)-trans-9-(5-chloro-2-(trifluoromethyl)phenyl)-2-(4-(2-hydroxypropan-2-yl)phenyl)-6,7,8,9-tetrahydropyrido [4',3':4,5]imidazo[1,2-b]pyridazin-6-ol (55); (+/−)-trans-9-(5-chloro-2-methoxyphenyl)-2-(4-(2-hydroxypropan-2-yl)phenyl)-6,7,8,9-tetrahydropyrido[1,2-b]pyridazin-6-ol (56); rac-(6S,9S)-9-(2-(difluoromethoxy)phenyl)-2-(4-(2-hydroxypropan-2-yl)phenyl)-7,9-dihydro-6H-pyrano[4',3':4,5]imidazo[1,2-b]pyridazin-6-ol (57); cis-9-(2-(difluoromethoxy)phenyl)-2-(4-(2-hydroxypropan-2-yl)phenyl)-6,9-dihydro-7H-pyrano[4',3':4,5]imidazo[1,2-b]pyridazin-6-ol (58); 9-(2-(difluoromethoxy)phenyl)-2-(4-(2-hydroxypropan-2-yl)phenyl)-6-methyl-6,9-dihydro-7H-pyrano[4',3':4,5]imidazo[1,2-b]pyridazin-6-ol (59); 9-(2-(difluoromethoxy)phenyl)-2-(4-(2-hydroxypropan-2-yl)

phenyl)-6-(pyridin-4-yl)-6,9-dihydro-7H-pyrano[4',3':4,5]imidazo[1,2-b]pyridazin-6-ol (60); cis-9-(2-(difluoromethoxy)phenyl)-2-(2-(2-hydroxypropan-2-yl)pyrimidin-5-yl)-6,9-dihydro-7H-pyrano[4',3':4,5]imidazo[1,2-b]pyridazin-6-ol (61); 2-(4-(9-(2-(difluoromethoxy)phenyl)-7,9-dihydro-6H-pyrano[4',3':4,5]imidazo[1,2-b]pyridazin-2-yl)phenyl)propan-2-ol (62); 2-(5-(9-(2-(difluoromethoxy)phenyl)-7,9-dihydro-6H-pyrano [4',3':4,5]imidazo[1,2-b]pyridazin-2-yl)pyrimidin-2-y0propan-2-ol (63); or 9-(2-(difluoromethoxy)phenyl)-2-(1-methyl-1H-pyrazol-4-yl)-7,9-dihydro-6H-pyrano[4',3':4,5]imidazo[1,2-b]pyridazine (64).

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I); and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen", as used herein, refer to F, Cl, Br, and I.

The term "cyano" refers to the group —CN.
The term "amino" refers to the group —NH$_2$.
The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "haloalkyl" as used herein is intended to include both branched and straight-chain saturated aliphatic hydrocarbon groups substituted with one or more halogen atoms. For example, "$C_{1-4}$ haloalkyl" is intended to include $C_1$, $C_2$, $C_3$, and $C_4$ alkyl groups substituted with one or more halogen atoms. Representative examples of haloalkyl groups include, but are not limited to, —CF$_3$, —CCl$_3$, —CFCl$_2$, and —CH$_2$CF$_3$.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "cyanoalkyl" includes both branched and straight-chain saturated alkyl groups substituted with one or more cyano groups. For example, "cyanoalkyl" includes —CH$_2$CN, —CH$_2$CH$_2$CN, and $C_{1-4}$ cyanoalkyl.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and $C_{1-4}$ hydroxyalkyl.

The term "alkenyl" refers to a straight or branched chain hydrocarbon radical containing from 2 to 12 carbon atoms and at least one carbon-carbon double bond. Exemplary such groups include ethenyl or allyl. For example, "$C_{2-6}$ alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "$C_{2-6}$ alkynyl" denotes straight and branched chain alkynyl groups with two to six carbon atoms.

The term "cycloalkyl", as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "cycloalkenyl", as used herein, refers to a nonaromatic cyclic hydrocarbon ring having one double bond. For example, $C_{5-6}$ cycloalkenyl denotes cyclopentenyl and cyclohexenyl.

The term "cycloalkynyl", as used herein, refers to a nonaromatic cyclic hydrocarbon ring having one triple bond. For example, $C_{5-6}$ cycloalkynyl denotes cyclopentynyl and cyclohexynyl.

The term "alkoxy", as used herein, refers to an alkyl group attached to the parent molecular moiety through an oxygen atom, for example, methoxy group (—OCH$_3$). For example, "$C_{1-3}$ alkoxy" denotes alkoxy groups with one to three carbon atoms.

The terms "haloalkoxy" and "—O(haloalkyl)" represent a haloalkyl group as defined above attached through an oxygen linkage (—O—). For example, "$C_{1-4}$ haloalkoxy" is intended to include $C_1$, $C_2$, $C_3$, and $C_4$ haloalkoxy groups.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "carbocyclo" or "carbocyclyl" may be used interchangeably and refer to cyclic groups having at least one saturated or partially saturated non-aromatic ring wherein all atoms of all rings are carbon. The carbocyclyl ring may be unsubstituted or may contain one or more substituents as valence allows. Thus, the term includes nonaromatic rings such as, for example, cycloalkyl, cycloalkenyl, and cycloalkynyl rings. Exemplary bicyclic carbocyclyl groups include, indanyl, indenyl, dihydronaphthalenyl, tetrahydronaphthenyl, hexahydronaphthalenyl, octahydronaphthalenyl, decahydronaphthalenyl, bicycloheptanyl, bicyclooctanyl, and bicyclononanyl.

The term "aryl" as used herein, refers to a group of atoms derived from a molecule containing aromatic ring(s) by removing one hydrogen that is bonded to the aromatic ring(s). Heteroaryl groups that have two or more rings must include only aromatic rings. Representative examples of aryl groups include, but are not limited to, phenyl and naphthyl. The aryl ring may be unsubstituted or may contain one or more substituents as valence allows.

The term "benzyl", as used herein, refers to a methyl group in which one of the hydrogen atoms is replaced by a phenyl group. The phenyl ring may be unsubstituted or may contain one or more substituents as valence allows.

The term "heteroatom" refers to oxygen (O), sulfur (S), and nitrogen (N).

The term "heterocyclo" or "heterocyclyl" may be used interchangeably and refer to cyclic groups having at least saturated or partially saturated non-aromatic ring and wherein one or more of the rings have at least one heteroatom (O, S or N), said heteroatom containing ring preferably having 1 to 3 heteroatoms independently selected from O, S, and/or N. The ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The heterocyclo group may be attached at any available nitrogen or carbon atom. The heterocyclo ring may be unsubstituted or may contain one or more substituents as valence allows.

Exemplary monocyclic heterocyclyl groups include pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, dihydroisoindolyl, and tetrahydroquinolinyl The term "heteroaryl" refers to substituted and unsubstituted aromatic 5- or 6-membered monocyclic groups and 9- or 10-membered bicyclic groups that have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group are aromatic and may contain only carbon atoms. The nitrogen and sulfur atoms may optionally be oxidized and the nitrogen atoms may optionally be quaternized. Bicyclic heteroaryl groups must include only aromatic rings. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, and pyrrolopyridyl.

The term "spirocarbocyclo" or "spirocarbocyclyl" refers to a carbocyclyl group attached to the molecular moiety by a carbon atom in the carbocyclyl ring that is shared with the molecular moiety.

The term "spiroheterocyclo" or "spiroheterocyclyl" refers to a heterocyclyl group attached to the molecular moiety by a carbon atom in the heterocyclyl ring that is shared with the molecular moiety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example, when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) Wermuth, C. G. et al., *The Practice of Medicinal Chemistry,* Chapter 31, Academic Press (1996);

b) Bundgaard, H. ed., *Design of Prodrugs,* Elsevier (1985);

c) Bundgaard, H., Chapter 5: "Design and Application of Prodrugs", *A Textbook of Drug Design and Development,* pp. 113-191, Krogsgaard-Larsen, P. et al., eds., Harwood Academic Publishers (1991); and d) Testa, B. et al., *Hydrolysis in Drug and Prodrug Metabolism,* Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to TNFα, or effective to treat or prevent autoimmune and/or inflammatory disease states, such as multiple sclerosis and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example, heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutical compositions can be presented in a pack or dispenser device which can contain one or more unit dosage forms including the compound of Formula (I). The pack can, for example, comprise metal or plastic foil, such as a blister pack. The pack or dispenser device can be accompanied by instructions for administration.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactos, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The pharmaceutical compositions may contain other therapeutic agents and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Utility

The compounds of the invention modulate the activity of TNFα. Accordingly, compounds of Formula (I) have utility in treating conditions associated with the modulation of TNFα.

The compounds in accordance with the present invention are beneficial in the treatment and/or prevention of various human ailments. The compounds in accordance with the present invention can be beneficial either as a standalone therapy or in combination with other therapies that therapeutically could provide greater benefit. The ailments for which the compounds in the present invention could be of benefit include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus, psoriasis, psoriatic arthropathy, vasculitis, polymyositis, scleroderma, multiple sclerosis, systemic sclerosis, ankylosing spondylitis, rheumatoid arthritis, psoriatic arthritis, non-specific inflammatory arthritis, juvenile inflammatory arthritis, juvenile idiopathic arthritis (including oligoarticular and polyarticular forms thereof), anemia of chronic disease, Still's disease (juvenile and/or adult onset), Behcet's disease and Sjögren's syndrome. Autoimmune endocrine disorders include thyroiditis. Organ-specific autoimmune disorders include Addison's disease, hemolytic or pernicious anemia, acute kidney injury, diabetic nephropathy, obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis, minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease, respiratory distress syndrome, sepsis, fever, muscular dystrophy (including Duchenne muscular dystrophy), and organ transplant rejection (including kidney allograft rejection).

Neurological and neurodegenerative disorders include Alzheimer's disease, Parkinson's disease, Huntington's disease, ischemia, stroke, amyotrophic lateral sclerosis, spinal cord injury, head trauma, seizures, and epilepsy.

Cardiovascular disorders include thrombosis, cardiac hypertrophy, hypertension, irregular contractility of the heart (e.g., during heart failure), and myocardial infarction.

Metabolic disorders include diabetes (including insulin-dependent diabetes mellitus and juvenile diabetes), dyslipidemia, and metabolic syndrome.

Ocular disorders include retinopathy (including diabetic retinopathy, proliferative retinopathy, non-proliferative retinopathy and retinopathy of prematurity), macular edema (including diabetic macular edema), age-related macular degeneration, vascularization (including corneal vascularization and neovascularization), retinal vein occlusion and various forms of uveitis, and keratitis.

Oncological disorders, which may be acute or chronic, include proliferative disorders, especially cancer, and cancer-associated complications (including skeletal complications, cachexia and anemia). Particular categories of cancer include hematological malignancy (including leukemia and lymphoma) and non-hematological malignancy (including solid tumor cancer, sarcoma, meningioma, glioblastoma multiform, neuroblastoma, melanoma, gastric carcinoma, and renal cell carcinoma). Chronic leukemia may be myeloid or lymphoid.

One embodiment provides a method of treating a disorder selected from autoimmune and inflammatory disorders; neurological and neurodegenerative disorders; pain and nociceptive disorders; cardiovascular disorders; metabolic disorders; ocular disorders; and oncological disorders, comprising administering to a mammalian patient in need of treatment, a compound according to claim 1 or a pharmaceutically acceptable salt thereof. Preferably, the patient is human. For example, a therapeutically effective amount for treating a disorder may be administered in the method of the present embodiment.

One embodiment provides a method of treating a disease or disorder associated with the activity of TNFα, comprising administering to a mammalian patient in need of treatment, a compound according to claim 1 or a pharmaceutically acceptable salt thereof. Preferably, the patient is human. For example, a therapeutically effective amount for treating a disorder may be administered in the method of the present embodiment.

One embodiment provides the compounds of Formula (I) for use in therapy. In the present embodiment, the use in therapy may include the administration of a therapeutically-effective amount of a compound of Formula (I).

The present invention also provides the use of the compounds of Formula (I) for the manufacture of a medicament for the treatment or prophylaxis of an allergic disorder and/or autoimmune and/or inflammatory disease. In the present embodiment, the use for the manufacture of a medicament may include the administration of a therapeutically-effective amount of a compound of Formula (I) for the treatment of prophylaxis of an allergic disorder and/or autoimmune and/or inflammatory disease.

The present invention also provides the use of the compounds of Formula (I) for the manufacture of a medicament for treatment of cancer. The present embodiment may include the use for the manufacture of a medicament includes the administration of a therapeutically-effective amount of a compound of Formula (I) for the treatment of prophylaxis of an allergic disorder and/or autoimmune and/or inflammatory disease.

The present invention provides the use of compounds of Formula (I) as pharmacological tools in the search for new pharmacological agents or in the development of new biological assays. In one embodiment, the compounds of Formula (I) are useful as radioligands or can be coupled to a fluorophore and utilized in assays to identify pharmacologically active compounds.

In one embodiment, the compounds of Formula (I) inhibit TNFα functional activity with $IC_{50}$ values of less than 10 µM, for example, from 0.001 to less than 10 µM, as measured by the TNF induced HEK-Blue assay. Preferably, the compounds of Formula (I) inhibit TNFα functional activity with $IC_{50}$ values of less than 1 µM, for example, from 0.001 to less than 1 µM. Other preferred compounds inhibit TNFα functional activity with $IC_{50}$ values of 100 nM and less, for example, from 1 to 100 nM.

Examples of compounds of Formula (I) as specified in the "Examples" section below, have been tested in one or more of the assays described below.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis,* Third Edition, Wiley and Sons (1999)).

Scheme 1 illustrates a general synthesis of imidazo[1,2-b]pyridazines of the general structure 8. Reaction of phthalimide (1) with methyl vinyl ketone in the presence of a base such as sodium ethoxide in a suitable solvent such as ethanol at elevated temperatures affords the coupled product 2. Bromination of 2 to afford 3 can be achieved using a suitable brominating reagent such as N-bromosuccinimide (NBS) in a suitable solvent such as DMF at ambient temperature. Condensing bromide 3 with 6-chloropyridazin-3-amine (4) in a suitable solvent such as ethanol at elevated temperature provides the imidazo[1,2-b]pyridazine 5. Removal of the phthalimide protecting group can be achieved by reaction with hydrazine in a suitable solvent such as ethanol at elevated temperatures to afford the amine 6. Cyclization of the amine 6 in the presence of an excess amount of the aldehyde or a ketone $R_5$—C(O)—$R_6$ and an acid catalyst such as pyridinium para-toluenesulfonate (PPTs) in a suitable solvent such as acetonitrile containing a dehydrating reagent such as anhydrous sodium sulfate affords 7. The resulting compounds 7 can then react with different boronic acids or boronic acid esters ($R_1$—B(OR)$_2$) under standard Suzuki coupling conditions, using a palladium catalyst such as Pd(dppf)Cl$_2$, to synthesize compounds 8, where $R_1$ represents various aryl and heteroaryl groups.

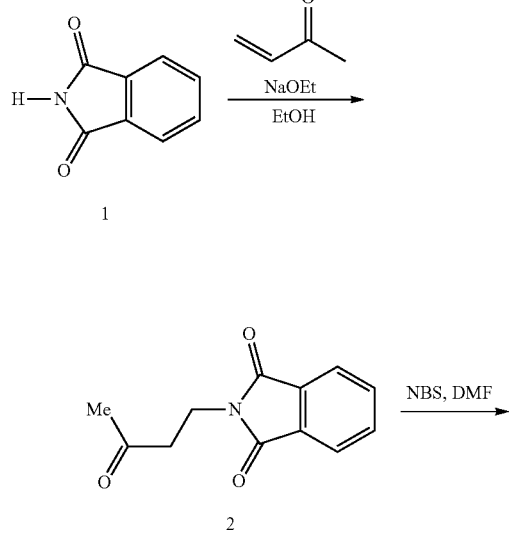

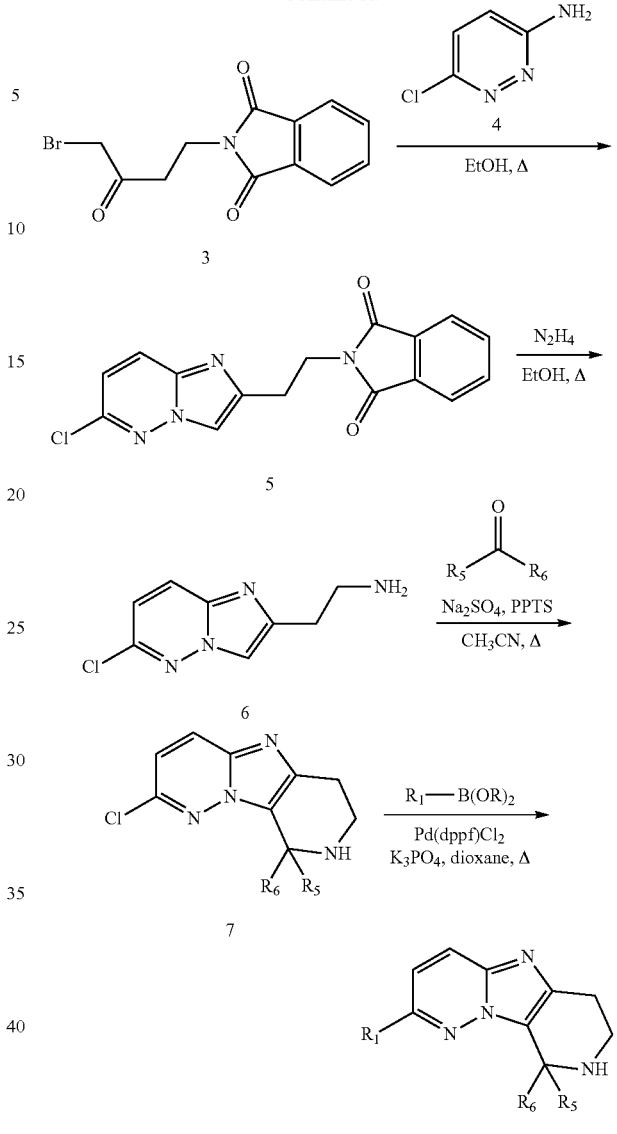

Scheme 2 illustrates a general synthesis of imidazo[1,2-b]pyridazines of the general structure 16. Starting with 6-chloropyridazin-3-amine (4) and reacting with ethyl 3-bromo-2-oxopropanoate in a suitable solvent such as ethanol at elevated temperature affords the cyclized product 9. Reduction of the ester in 9 to afford the aldehyde 10 can be achieved using a suitable reducing reagent such as diisobutylaluminum hydride (DIBAL-H) in a suitable solvent such as dichloromethane (DCM) at −78° C. Aldehyde 10 can be reacted with nitromethane in the presence of a suitable base such as triethylamine to afford the alcohol 12. The resulting alcohol 11 can then be protected with a reagent such as tert-butyldiphenylsilyl chloride (TBDPSCl) in the presence of a suitable base such as imidazole in a solvent such as dichloromethane to afford the protected alcohol 12. Reduction of 12 using a reducing reagent such as iron in the presence of an acid such as acetic acid in solvents such as ethyl acetate/aqueous THF under heating conditions affords the amine product 13. Coupling of the amine 13 with ketones of the type $R_5$—C(O)—$R_6$ and in situ cyclization can be performed in the presence of an acid catalyst such as PPTs in a solvent such as acetonitrile under heating conditions to afford the tricyclic compounds 14. Subsequent deprotection of 14 using tetrabutylammonium fluoride (TBAF) in a suitable solvent such as THF affords the alcohol 15 which can then be coupled to boronic acids or boronic acid esters ($R_1$—$B(OR)_2$) under standard Suzuki coupling conditions, using a palladium catalyst such as $PdCl_2(dppf)$, to synthesize compounds 16 where $R_1$ represents various aryl and heteroaryl groups.

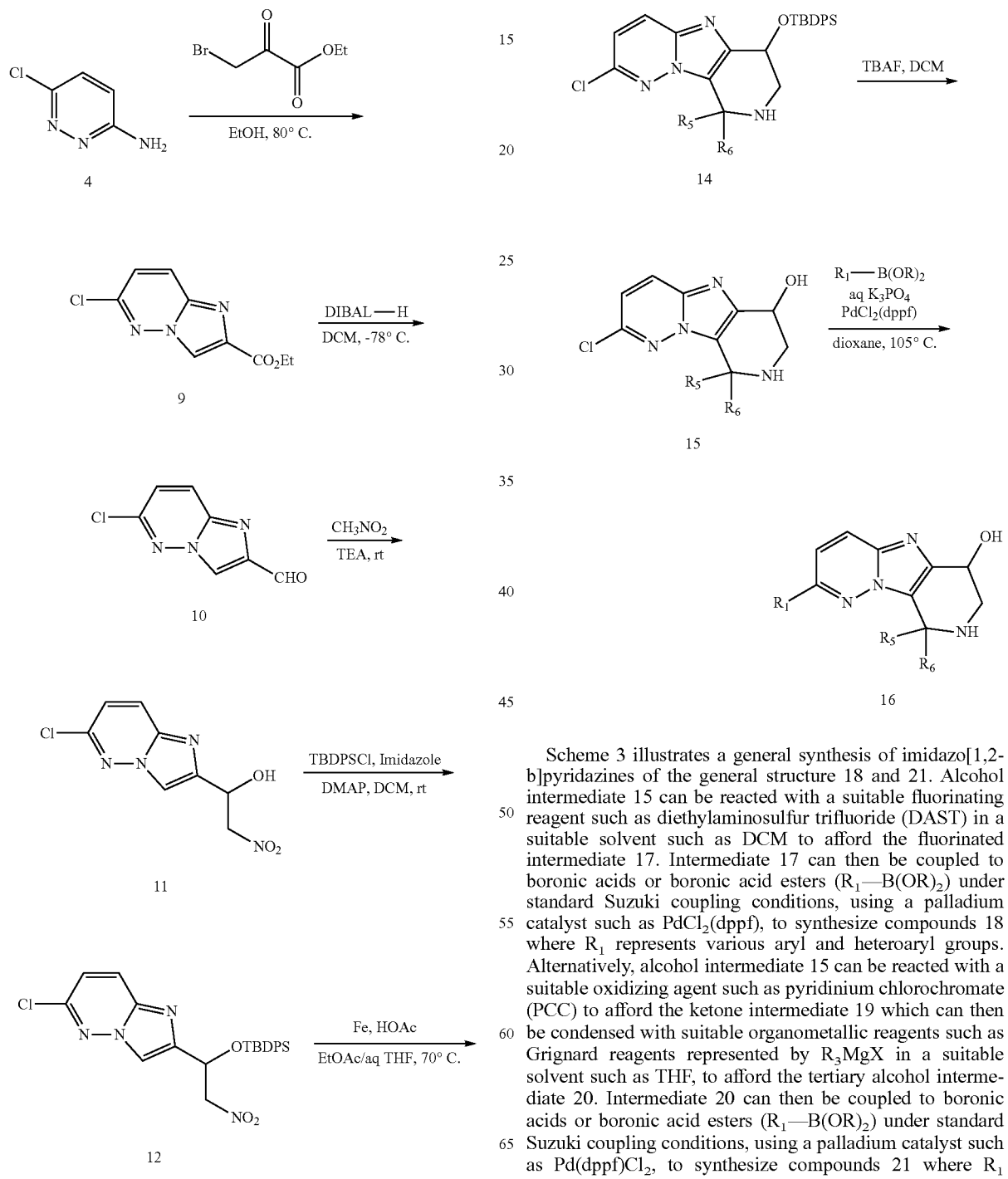

Scheme 3 illustrates a general synthesis of imidazo[1,2-b]pyridazines of the general structure 18 and 21. Alcohol intermediate 15 can be reacted with a suitable fluorinating reagent such as diethylaminosulfur trifluoride (DAST) in a suitable solvent such as DCM to afford the fluorinated intermediate 17. Intermediate 17 can then be coupled to boronic acids or boronic acid esters ($R_1$—$B(OR)_2$) under standard Suzuki coupling conditions, using a palladium catalyst such as $PdCl_2(dppf)$, to synthesize compounds 18 where $R_1$ represents various aryl and heteroaryl groups. Alternatively, alcohol intermediate 15 can be reacted with a suitable oxidizing agent such as pyridinium chlorochromate (PCC) to afford the ketone intermediate 19 which can then be condensed with suitable organometallic reagents such as Grignard reagents represented by $R_3MgX$ in a suitable solvent such as THF, to afford the tertiary alcohol intermediate 20. Intermediate 20 can then be coupled to boronic acids or boronic acid esters ($R_1$—$B(OR)_2$) under standard Suzuki coupling conditions, using a palladium catalyst such as $Pd(dppf)Cl_2$, to synthesize compounds 21 where $R_1$ represents various aryl and heteroaryl groups.

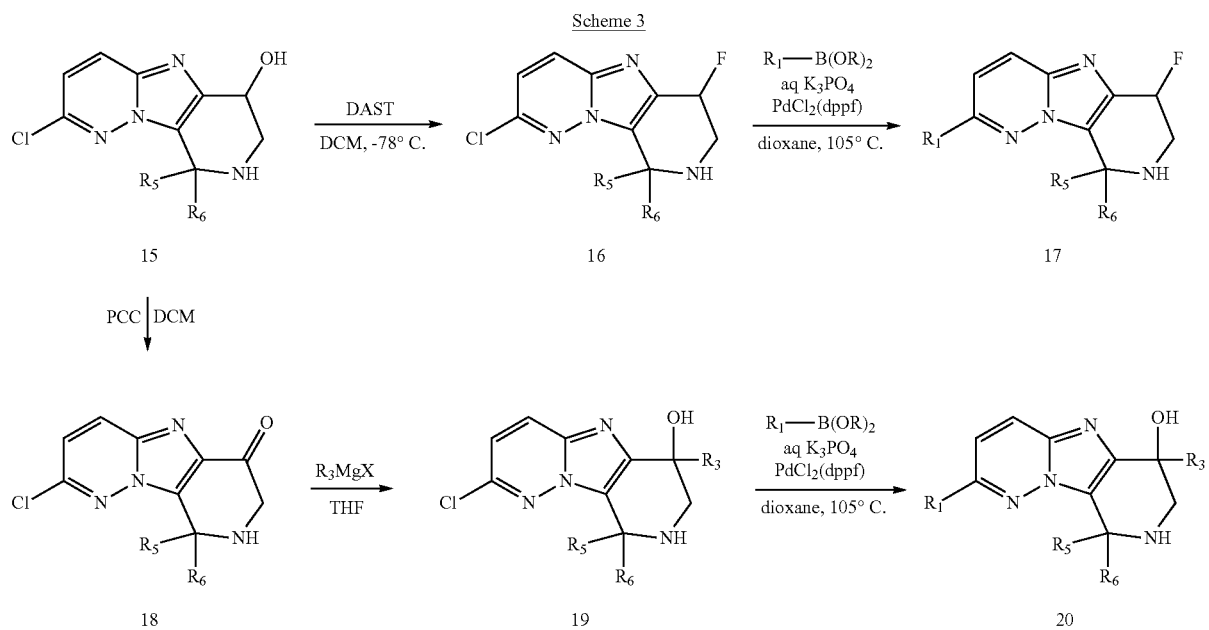

Scheme 4 illustrates a general synthesis of imidazo[1,2-b]pyridazines of the general structure 24 and 25. Reaction of 4 with ethyl 4-bromo-3-oxobutanoate in a suitable solvent such as toluene at elevated temperatures affords the imidazo[1,2-b] pyridazine 22. Reduction of 22 to afford alcohol 23 can be achieved using a suitable reducing reagent such as sodium borohydride in a suitable solvent such as methanol at ambient temperature. Reaction of the alcohol 23 with an excess of the aldehyde or a ketone [$R_5$—C(O)—$R_6$] in the presence of an acid catalyst such as trifluoroacetic acid (TFA) in a suitable solvent such as methanol under elevated temperatures affords the cyclized products 24. When $R_1$ is a chloro group, the resulting compounds 24 can then react with different boronic acids or boronic acid esters ($R_1'$—B(OR)$_2$) under standard Suzuki coupling conditions, using a palladium catalyst such as PdCl$_2$(dppf), to synthesize compounds 25, where $R_1'$ represents various aryl and heteroaryl groups.

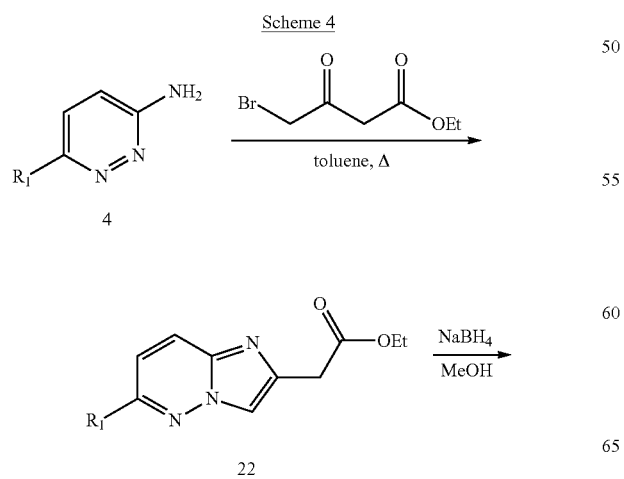

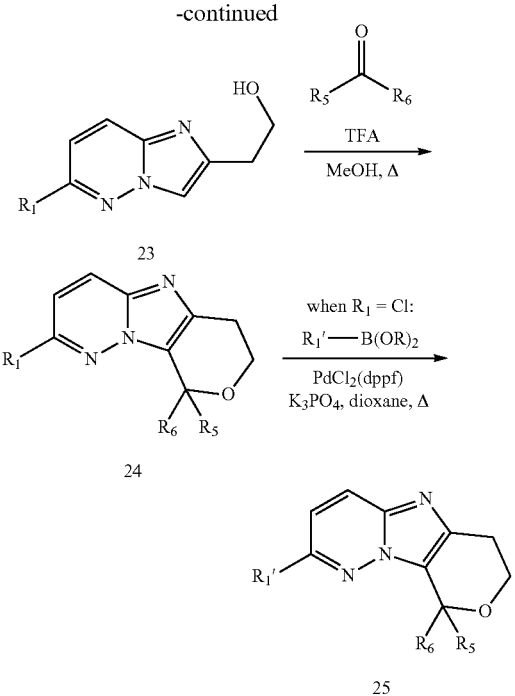

Scheme 5 illustrates a general synthesis of imidazo[1,2-b]pyridazines of the general structure 32 and 35. Treatment of methyl 6-chloroimidazo[1,2-b]pyridazine-2-carboxylate (26) with lithium magnesium 2,2,6,6-tetramethylpiperidin-1-ide dichloride results in regioselective magnesiation (Clososki, G. C. et al., *Angew. Chem. Int. Ed.*, 46:7681 (2007)). Subsequent in situ coupling with aldehyde or ketone [$R_5$—C(O)—$R_6$] can provide compound 27. The ester group in 27 can be reduced to give aldehyde 28 using conditions such as diisobutylaluminum hydride in dichloromethane. Aldehyde 28 can react with an ylide that can be generated by treating methyltriphenylphosphonium bromide with a base such as potassium bis(trimethylsilyl)amide (KHMDS) in a solvent such THF to provide alkene 29. Dihydroxylation of 29 can be achieved using conditions such as osmium tetroxide and N-methylmorpholine-N-oxide in solvents such as acetone and water. Treatment of the resulting diol 30 with an acid such as p-toluenesulfonic acid in a solvent such as toluene at elevated temperature can provide tricyclic compound 31. The resulting compound 31 can react with different boronic acids or boronic acid esters ($R_1$—$B(OR)_2$) under standard Suzuki coupling conditions, using a palladium catalyst such as $PdCl_2(dppf)$, to synthesize compounds 32, where $R_1$ represents various aryl and heteroaryl groups. Alcohol 31 can also be oxidized to ketone 33 under conditions such as Dess-Martin periodinane in dichloromethane. Treatment of 33 with a Grignard reagent ($R_3MgCl$) or organo lithium reagent (RLi) yields tertiary alcohol 34, which can be converted to compound 35 under Suzuki coupling conditions similar to synthesis of 32.

Abbreviations

AcOH acetic acid
aq aqueous
BOP benzotriazol-1-yloxytris-(dimethylamino)-phosphonium hexafluorophosphate
DAST diethylaminosulfur trifluoride
DCM dichloromethane
DIBAL-H diisobutylaluminum hydride
DIEA N,N-diisopropylethylamine
DMAP N,N-dimethylaminopyridine
DMF dimethylformamide
DMSO dimethyl sulfoxide
EtOAc ethyl acetate
$Et_2O$ diethyl ether
h hour(s)
HPLC High Pressure Liquid Chromatography
LC/MS Liquid Chromatography-Mass Spectroscopy Scheme 5

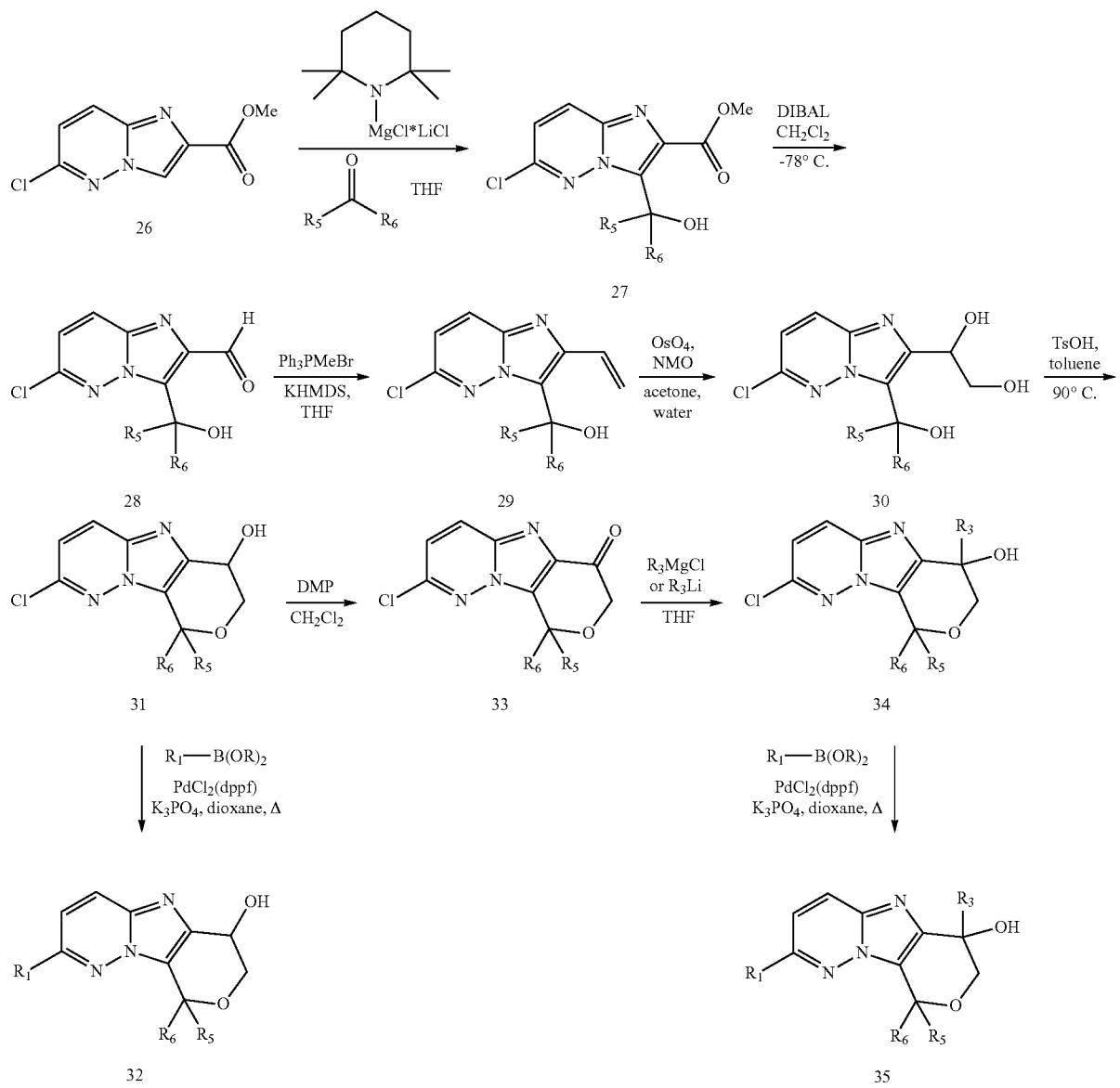

MeOH methanol
min minute(s)
mmol millimole(s)
NBS N-bromosuccinimide
NMO N-methylmorpholine-N-oxide
NMR nuclear magnetic resonance spectroscopy
PCC pyridinium chlorochromate
$PdCl_2$(dppf) [1,1'-bis(diphenylphosphino)ferrocene]dichloropalladium(II),
$Pd(Ph_3P)_4$ tetrakis(triphenylphosphine)palladium
PPTs pyridiniumpara-toluenesulfonate
TBAF tetrabutylammonium fluoride
TBDPSCl tert-butyldiphenylsilyl chloride
TFA trifluoroacetic acid
THF tetrahydrofuran

EXAMPLES

The following Examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc.) and are abbreviated as Int. 1, Int. 2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well-known bioisosteric replacements known in the art, for example, replacement of a carboxylic acid group with a tetrazole or a phosphate moiety.

HPLC Conditions

Condition A: Column: YMC COMBISCREEN® ODS-A 4.6×50 mm (4 min.); Linear gradient of 0 to 100% Solvent B over 4 min with 1 min hold at 100% B; UV visualization at 220 nm; Solvent A=10% MeOH, 90% $H_2O$, 0.2% $H_3PO_4$; Solvent B=90% MeOH, 10% $H_2O$, 0.2% $H_3PO_4$; Flow: 4 mL/min.

Condition B: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Condition C: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

Condition D: Column: XBridge Phenyl, 4.6×150 mm, 3.5μ; Mobile Phase A: 5:95 acetonitrile:water with 0.05% TFA; Mobile Phase B: 95:5 acetonitrile:water with 0.05% TFA; Gradient: 10-100% B over 25 minutes, then a 5-minute hold at 100% B; Flow: 1 mL/min.

Condition E: Column: ZORBAX® CN, 4.6×150 mm, 5μ; Mobile Phase A: 5:95 acetonitrile:water with 10 mM ammonium acetate; Mobile Phase B: 95:5 acetonitrile:water with 10 mM ammonium acetate; Gradient: 10-100% B over 25 minutes, then a 5-minute hold at 100% B; Flow: 1 mL/min.

Condition F: Column: SunFire C18, 4.6×150 mm, 3.5μ; Mobile Phase A: 5:95 acetonitrile:water with 0.05% TFA; Mobile Phase B: 95:5 acetonitrile:water with 0.05% TFA; Gradient: 10-100% B over 25 minutes, then a 5-minute hold at 100% B; Flow: 1 mL/min.

Condition G: Column: Ascentis Express C18 (4.6×50) mm, 2.7 μm; Mobile Phase A: 5:95 acetonitrile:water with 10 mM ammonium acetate; Mobile Phase B: 95:5 acetonitrile: water with 10 mM ammonium acetate; Temperature: 45° C.; Gradient: 0-100% B over 4 minutes; Flow: 4.00 mL/min.

Condition H: Column: Ascentis Express C18 (2.1×50) mm, 2.7 μm; Mobile Phase A: 5:95 acetonitrile:water with 10 mM ammonium acetate; Mobile Phase B: 95:5 acetonitrile:water with 10 mM ammonium acetate; Gradient: 0-100% B over 3.4 minutes; Flow: 1.11 mL/min.

Condition I: Waters Acquity UPLC BEH C18 (2.1×50) mm, 1.7-μm particles; Mobile Phase A: 5:95 acetonitrile: water with 0.05% TFA; Mobile Phase B: 95:5 acetonitrile: water with 0.05% TFA; Temperature: 50° C.; Gradient: 2-98% B over 1 minutes, then a 0.5-minute hold at 98% B; Flow: 0.80 mL/min.

Condition J: Column: XBridge Phenyl, 3.0×150 mm, 3.5μ; Mobile Phase A: 5:95 acetonitrile:water with 0.05% TFA; Mobile Phase B: 95:5 acetonitrile:water with 0.05% TFA; Gradient: 10-100% B over 12 minutes, then a 3-minute hold at 100% B; Flow: 1 mL/min.

Condition K: Column: PHENOMENEX® Kinetex, C18 (2.1×50) mm, 2.6μ; Mobile Phase A: 10:90 acetonitrile: water with 0.1% TFA; Mobile Phase B: 90:10 acetonitrile: water with 0.1% TFA; Gradient: 0-100% B over 1.5 minutes, then a 0.5-minute hold at 100% B; Flow: 1 mL/min.

Condition L: Column: SunFire C18, 3.0×150 mm, 3.5μ; Mobile Phase A: 5:95 acetonitrile:water with 0.05% TFA; Mobile Phase B: 95:5 acetonitrile:water with 0.05% TFA; Gradient: 10-100% B over 12 minutes, then a 3-minute hold at 100% B; Flow: 1 mL/min.

Condition M: Column: Waters Acquity UPLC BEH C18, 2.1×50 mm, 1.7-μm particles; Mobile Phase A: water; Mobile Phase B: acetonitrile; Temperature: 50° C.; Gradient: 2-98% B over 1 minute, then a 0.75-minute hold at 98% B; Flow: 0.8 mL/min.

Condition N: Column: YMC Pro C18 S5 ODS 4.6×50 mm; Linear gradient of 0 to 100% Solvent B over 4 min with 1 min hold at 100% B; UV visualization at 220 nm; Solvent A=10% MeOH, 90% $H_2O$, 0.2% $H_3PO_4$; Solvent B=90% MeOH, 10% $H_2O$, 0.2% $H_3PO_4$; Flow: 4 mL/min.

Condition O: Waters Acquity UPLC BEH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Tempera-

Example 1

(+/−)-9-(2-(Difluoromethoxy)phenyl)-2-(6-methoxy-pyridin-3-yl)-6,7,8,9-tetrahydropyrido[4',3':4,5]imidazo[1,2-b]pyridazine

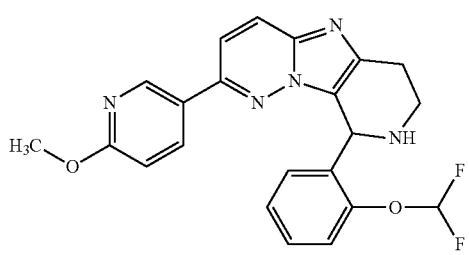
(1)

Intermediate 1A: 2-(3—Oxobutyl)isoindoline-1,3-dione

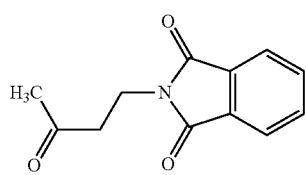
(1A)

To a slurry of isoindoline-1,3-dione (5.00 g, 34.0 mmol) and but-3-en-2-one (2.38 g, 34 mmol) in ethyl acetate (40 mL) was added sodium ethoxide (0.116 g, 1.699 mmol) in ethanol (10 mL) at room temperature. The reaction mixture was stirred at room temperature for 2 h and heated at 80° C. in an oil bath overnight. The reaction mixture was concentrated to dryness, taken up in DCM (300 mL) and washed with aqueous 1 N NaOH (50 mL×6). The organics were dried over $Na_2SO_4$, filtered and concentrated to afford 2-(3-oxobutyl)isoindoline-1,3-dione (2.15 g, 9.90 mmol, 29% yield) as a tan solid. LC/MS (M+H): 218.2; LC retention time: 1.857 min (analytical HPLC Method N); $^1$H NMR (400 MHz, $CDCl_3$): δ ppm 7.85 (dd, J=5.4, 3.0 Hz, 2H), 7.77-7.70 (m, 2H), 4.07-3.89 (m, 2H), 2.98-2.77 (m, 2H), 2.19 (s, 3H).

Intermediate 1B: 2-(4-Bromo-3-oxobutyl)isoindoline-1,3-dione

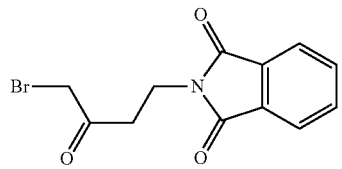
(1B)

To a cold slurry of 2-(3-oxobutyl)isoindoline-1,3-dione (2.12 g, 9.76 mmol) in MeOH (25 mL) at 0° C. was added bromine (1.006 mL, 19.52 mmol). The reaction mixture was allowed to slowly warm to room temperature overnight. The reaction mixture was initially quenched with 10 M aq $H_2SO_4$ (15 mL). Once the intermediate methyl ether was no longer visible by LCMS, the reaction mixture was diluted with additional water (20 mL). The solid was collected, rinsed with water and air dried on the filter to afford 2-(4-bromo-3-oxobutyl)isoindoline-1,3-dione (2.13 g, 7.19 mmol, 73.7% yield) as a white solid. LC/MS (weak M+H): 295.9; LC retention time: 2.148 min (analytical HPLC Method N); $^1$H NMR (400 MHz, $CDCl_3$): δ ppm 7.86 (dd, J=5.5, 3.1 Hz, 2H), 7.73 (dd, J=5.5, 3.1 Hz, 2H), 4.02 (t, J=7.2 Hz, 2H), 3.93 (s, 2H), 3.13 (t, J=7.2 Hz, 2H).

Intermediate 1C: 2-(2-(6-Chloroimidazo[1,2-b]pyridazin-2-yl)ethyl)isoindoline-1,3-dione

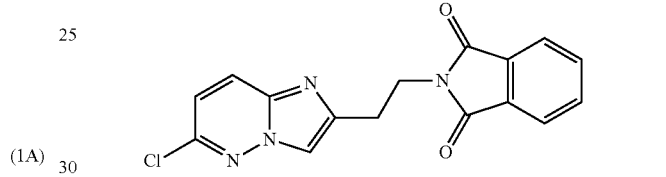
(1C)

A slurry of 2-(4-bromo-3-oxobutyl)isoindoline-1,3-dione (1.0 g, 3.38 mmol) and 6-chloropyridazin-3-amine (0.437 g, 0.43 mmol) in ethanol (5 mL) in a reaction vial was heated at 75° C. behind blast shield. After 3 h, the reaction mixture was cooled to room temperature and the solid was collected by filtration, rinsed with ethanol to afford white solid, which was slurried with aqueous $NaHCO_3$ for 1 h. The solid was collected and rinsed with water and dried under vacuum to afford 2-(2-(6-chloroimidazo[1,2-b] pyridazin-2-yl)ethyl) isoindoline-1,3-dione (0.962 g, 2.94 mmol, 87% yield). LC retention time 2.55 min. (analytical HPLC Method A). LC/MS (M+H): 327.

Intermediate 1D: 2-(6-Chloroimidazo[1,2-b]pyridazin-2-yl)ethan-1-amine

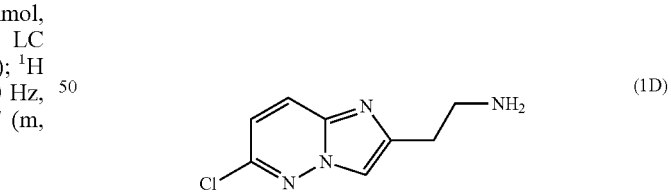
(1D)

To slurry of 2-(2-(6-chloroimidazo[1,2-b]pyridazin-2-yl) ethyl)isoindoline-1,3-dione (960 mg, 2.94 mmol) in ethanol (10 mL) was added hydrazine hydrate (735 mg, 14.7 mmol) and the resulting mixture was stirred at room temperature for 2 h over which time the solution became clear initially, followed by the formation of a white precipitate. The resulting slurry was filtered and the filter cake was washed with additional ethanol. The filtrate containing the product was concentrated to afford a light tan oil, which was triturated with DCM and filtered again washing the filter cake with additional DCM. The filtrate was concentrated to afford near white solid as pure product as 2-(6-chloroimidazo [1,2-b]pyridazin-2-yl)ethan-1-amine (356 mg, 1.810 mmol, 62% yield). LC retention time 0.39 min (analytical HPLC Method A). LC/MS (M+H): 197.

Intermediate 1E: (+/−)-2-Chloro-9-(2-(difluoromethoxy)phenyl)-6,7,8,9-tetrahydropyrido [4',3':4,5]imidazo[1,2-b]pyridazine

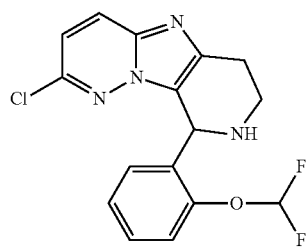

(1E)

To a solution of 2-(6-chloroimidazo[1,2-b]pyridazin-2-yl)ethan-1-amine (100 mg, 0.509 mmol), 2-(difluoromethoxy)benzaldehyde (105 mg, 0.610 mmol) and anhydrous sodium sulfate (361 mg, 2.54 mmol) in acetonitrile (1.0 mL) was added PPTs (958 mg, 3.81 mmol). The resulting mixture was deoxygenated by bubbling nitrogen through the mixture for ~5 min. and then heated at 80° C. in a vial for ~16 h. The reaction mixture was cooled and concentrated under reduced pressure, yielding a clear oil, which was partitioned between EtOAc (60 mL) and aqueous saturated NaHCO$_3$ (20 mL). The layers were separated and the aqueous portion was extracted with EtOAc (40 mL) and the combined organic extracts were washed with brine, dried over anhydrous sodium sulfate, filtered, and concentrated under reduced pressure to afford the crude product as a tan oil. Purification by flash chromatography on silica gel (4 g silica gel cartridge) using EtOAc/hexane mixtures initially followed by a linear gradient of DCM/MeOH afforded a colorless oil as (+/−)-2-chloro-9-(2-(difluoromethoxy)phenyl)-6,7,8,9-tetrahydropyrido-[4',3':4,5]imidazo[1,2-b]pyridazine (78 mg, 0.22 mmol, 44% yield). $^1$H NMR (400 MHz, chloroform-d); δ 7.84 (d, J=9.4 Hz, 1H), 7.36-7.29 (m, 2H), 7.25-7.20 (m, 1H), 7.07 (td, J=7.5, 1.1 Hz, 1H), 6.99-6.94 (m, 1H), 6.82 (dd, J=7.7, 1.6 Hz, 1H), 5.85 (s, 1H), 3.30-2.94 (m, 4H). LC retention time: 1.73 min (analytical HPLC Method A). LC/MS (M+H): 351.

Example 1

A reaction vial was charged with (+/−)-2-chloro-9-(2-(difluoromethoxy)phenyl)-6,7,8,9-tetrahydropyrido[4',3':4,5]imidazo[1,2-b]pyridazine (15 mg, 0.043 mmol), (6-methoxypyridin-3-yl)boronic acid (8.50 mg, 0.056 mmol), 2M aqueous potassium phosphate tribasic (0.064 mL, 0.128 mmol) and dioxane (0.3 mL). The resulting mixture was deoxygenated by bubbling nitrogen through the mixture for ~5 min. Next, PdCl$_2$(dppf) (1.565 mg, 2.138 μmol) was added, the vial was capped, and the mixture was heated at 90° C. for 45 min. After cooling to room temperature, the reaction mixture was concentrated under vacuum and the crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 10-50% B over 19 minutes, then a 5-minute hold at 100% B; Flow: 20 mL/min. Fractions containing the desired product were combined and dried via centrifugal evaporation.

The material was further purified via preparative LC/MS with the following conditions: Column: XBridge C18, 30×150 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-60% B over 20 minutes, then a 2-minute hold at 100% B; Flow: 40 mL/min. Fractions containing the product were combined and dried via centrifugal evaporation to afford 6.8 g (38%) of (+/−)-9-(2-(difluoromethoxy)phenyl)-2-(6-methoxypyridin-3-yl)-6,7,8,9-tetrahydropyrido[4',3':4,5]-imidazo[1,2-b]pyridazine. $^1$H NMR (500 MHz, DMSO-d$_6$): δ 8.50 (s, 1H), 8.09 (d, J=9.4 Hz, 1H), 7.89 (d, J=8.7 Hz, 1H), 7.68 (d, J=9.4 Hz, 1H), 7.44-7.33 (m, 1H), 7.32-7.23 (m, 1H), 7.14-7.06 (m, 1H), 6.90 (d, J=7.4 Hz, 1H), 6.86 (d, J=8.8 Hz, 1H), 5.71 (s, 1H), 3.87 (s, 3H), 3.47 (br. s., 1H), 3.21-3.00 (m, 2H), 2.98-2.76 (m, 2H). LC retention time: 1.12 min (analytical HPLC Method A). LC/MS (M+H): 424.

Example 2

(+/−)-2-(4-(9-(2-(Difluoromethoxy)phenyl)-6,7,8,9-tetrahydropyrido [4',3':4,5]imidazo[1,2-b]pyridazin-2-yl)phenyl)propan-2-ol

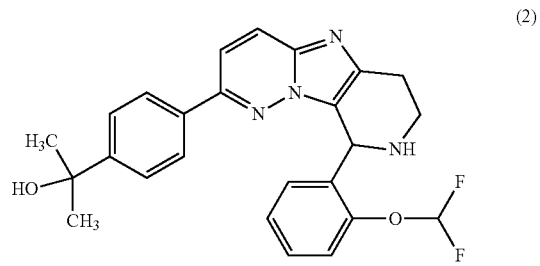 [SMILES: CC(C)(O)c1ccc(-c2ccc3nc4c(n3n2)C(c2ccccc2OC(F)F)NCC4)cc1]

(2)

Example 2 was prepared according to the general method described for Example 1 in last step using (+/−)-2-chloro-9-(2-(difluoromethoxy)phenyl)-6,7,8,9-tetrahydropyrido [4',3':4,5]-imidazo[1,2-b]pyridazine to yield (+/−)-2-(4-(9-(2-(difluoro-methoxy)phenyl)-6,7,8,9-tetrahydropyrido[4',3':4,5]imidazo[1,2-b]pyridazin-2-yl)phenyl)propan-2-ol (18 mg, 0.040 mmol, 77% yield). LC/MS (M+H): 451; LC retention time: 1.00 min (E). $^1$H NMR (400 MHz, DMSO-d$_6$) δ 8.21 (d, J=9.6 Hz, 1H), 7.84 (d, J=9.6 Hz, 1H), 7.64-7.58 (m, 2H), 7.58 (m, 1H), 7.49 (d, J =8.6 Hz, 2H), 7.43 (d, J =8.2 Hz, 1H), 7.36 (t, J =73.2 Hz, 1H), 7.28-7.21 (m, 1H), 7.18 (m, 1H), 6.41 (s, 1H), 3.73-3.51 (m, 2H), 3.29 (dt, J =17.0, 5.9 Hz, 1H), 3.16 (dt, J=17.0, 5.9 Hz, 1H), 1.41 (s, 6H).

Example 3

(+/−)-2-(5-(9-(2-(Difluoromethoxy)phenyl)-6,7,8,9-tetrahydropyrido[4',3':4,5]imidazo[1,2-b]pyridazin-2-yl)pyrimidin-2-yl)propan-2-ol

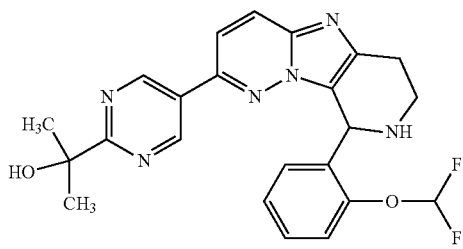

(3)

Example 3 was prepared according to the general method described for Example 1 in last step using (+/−)-2-chloro-9-(2-(difluoromethoxy)phenyl)-6,7,8,9-tetrahydropyrido [4',3':4,5]-imidazo[1,2-b]pyridazine to yield (+/−)-2-(5-(9-(2-(difluoro-methoxy)phenyl)-6,7,8,9-tetrahydropyrido[4',3':4,5]imidazo[1,2-b]pyridazin-2-yl)pyrimidin-2-yl)propan-2-ol (13 mg, 0.029 mmol, 56% yield). LC/MS (M+H): 453; LC retention time: 1.29 min (E); $^1$H NMR (500 MHz, DMSO-$d_6$): δ 8.96 (s, 2H), 8.16 (d, J=9.4 Hz, 1H), 7.78 (d, J=9.4 Hz, 1H), 7.41-7.19 (m, 3H), 7.16-7.01 (m, 1H), 6.90 (d, J=6.9 Hz, 1H), 5.70 (s, 1H), 3.19-2.98 (m, 2H), 2.97-2.79 (m, 2H), 1.90 (s, 1H), 1.47 (s, 6H).

Examples 4 and 5

(+/−)-Cis and trans-9-(2-(difluoromethoxy)phenyl)-2-(4-(2-hydroxypropan-2-yl)phenyl)-6,7,8,9-tetrahydropyrido[4',3':4,5]imidazo[1,2-b]pyridazin-6-ol

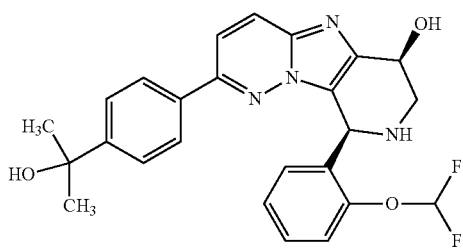

(4)

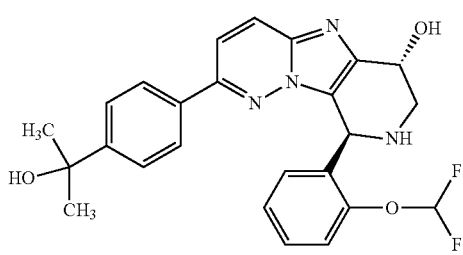

(5)

Intermediate 4A: Ethyl 6-chloroimidazo[1,2-b]pyridazine-2-carboxylate

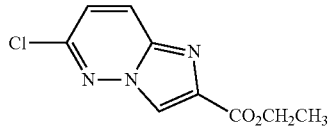

(4A)

To slurry of 6-chloropyridazin-3-amine (10.00 g, 77 mmol) in ethanol (30 mL) at 0° C. was added ethyl 3-bromo-2-oxopropanoate (20.07 g, 93 mmol) in ethanol (5 mL) via pipette. After complete addition, the cooling bath was removed and the reaction mixture was allowed to stir at room temperature for 15 min., then heated at 80° C. for 30 min. to give a clear solution. After heating for 2 h, the mixture was cooled to room temperature and the resulting precipitated solid was collected and rinsed with cold ethanol to afford beige solid. The solid was suspended in aqueous saturated NaHCO$_3$ and was stirred for 30 min. before collecting the solid by vacuum filtration. The filter cake was rinsed with water, dried on filter, and further dried under vacuum to afford a tan solid as ethyl 6-chloroimidazo[1,2-b]pyridazine-2-carboxylate (8.8 g, 39.0 mmol, 51% yield). $^1$H NMR (400 MHz, chloroform-$d_3$): δ 8.46 (s, 1H), 8.13 (d, J=9.5 Hz, 1H), 7.23 (d, J=9.5 Hz, 1H), 4.49 (q, J=7.2 Hz, 2H), 1.46 (t, J=7.1 Hz, 3H). LC retention time 2.29 min (analytical HPLC Method A). LC/MS (M+H): 226/228 (~3:1).

Intermediate 4B: 6-Chloroimidazo[1,2-b]pyridazine-2-carbaldehyde

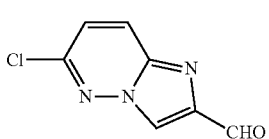

(4B)

To a clear solution of ethyl 6-chloroimidazo[1,2-b]pyridazine-2-carboxylate (2.95 g, 13.07 mmol) in dichloromethane (40 mL) at −78° C. under nitrogen was added a 1 M solution of DIBAL-H in toluene (19.61 mL, 19.61 mmol) dropwise over ~20 min. The resulting mixture was stirred at this temperature for 2 h. The reaction was quenched by a slow dropwise addition of 10 mL of ethanol followed by continued stirring at −78° C. for 45 min. The cooling bath was replaced with a 0° C. ice bath and the mixture was stirred for an additional 1 h followed by dilution with 150 mL of EtOAc. The mixture was then poured into cold aqueous saturated NaHCO$_3$ (60 mL) with stirring at 0° C. followed by warming to room temperature. CELITE® (10 g) was added and the mixture was filtered through CELITE® and the filter cake was rinsed thoroughly with several portions of warm EtOAc. The resulting filtrate was dried over anhydrous sodium sulfate and was concentrated to afford a tan solid as 6-chloroimidazo[1,2-b]pyridazine-2-carbaldehyde (2.16 g, 11.9 mmol, 91% yield). $^1$H NMR (400 MHz, chloroform-$d_3$): δ 10.22-10.10 (m, 1H), 8.45 (s, 1H), 8.01 (dd, J=9.6, 0.6 Hz, 1H), 7.20 (d, J=9.5 Hz, 1H). LC retention time 1.11 min (analytical HPLC Method A). LC/MS (M+H): 182.

Intermediate 4C: (+/−)-1-(6-Chloroimidazo[1,2-b]pyridazin-2-yl)-2-nitroethan-1-ol

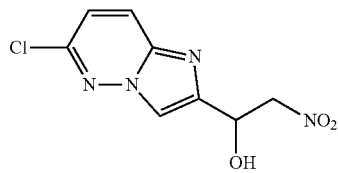
(4C)

To a slurry of 6-chloroimidazo[1,2-b]pyridazine-2-carbaldehyde (2.85 g, 15.7 mmol) in nitromethane (25 mL) was added TEA (3.72 mL, 26.7 mmol) at room temperature. The resulting mixture was allowed to stir at room temperature for 3 h and then was concentrated to afford a tan solid as (+/−)-1-(6-chloroimidazo[1,2-b]pyridazin-2-yl)-2-nitroethanol (3.80 g, 15.66 mmol, 100% yield). $^1$H NMR (400 MHz, chloroform-d3): δ 8.01 (s, 1H), 7.86 (d, J=9.4 Hz, 1H), 7.12 (d, J=9.5 Hz, 1H), 5.67 (dd, J=8.5, 3.1 Hz, 1H), 4.96-4.90 (m, 1H), 4.86-4.78 (m, 1H). LC retention time 1.11 min (analytical HPLC Method A). LC/MS (M+H): 243.

Intermediate 4D: (+/−)-2-(1-((tert-Butyldiphenylsilyl)oxy)-2-nitroethyl)-6-chloroimidazo [1,2-b]pyridazine

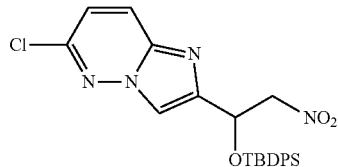
(4D)

To a solution of (+/−)-1-(6-chloroimidazo[1,2-b]pyridazin-2-yl)-2-nitroethanol (3.70 g, 15.25 mmol) and imidazole (2.08 g, 30.5 mmol) in DCM (30 mL) at room temperature was added TBDPS-Cl (4.70 mL, 18.30 mmol), followed by DMAP (0.093 g, 0.763 mmol). The resulting mixture was allowed to stir at room temperature for ~16 h. The mixture concentrated to remove DCM, diluted with EtOAc (300 mL), washed with water, brine, and dried over anhydrous sodium sulfate. The solvents were evaporated under reduced pressure, and the residue was triturated with ether and the solid was collected by filtration, rinsed with ether to afford a tan solid as (+/−)-2-(1-((tert-butyldiphenylsilyl)oxy)-2-nitroethyl)-6-chloroimidazo[1,2-b]pyridazine (4.50 g, 9.36 mmol, 61% yield). $^1$H NMR (400 MHz, chloroform-d$_3$): δ 7.79 (dd, J=9.5, 0.6 Hz, 1H), 7.69-7.64 (m, 2H), 7.52 (s, 1H), 7.51-7.44 (m, 3H), 7.43-7.38 (m, 2H), 7.35-7.29 (m, 1H), 7.25-7.18 (m, 2H), 7.05 (d, J=9.5 Hz, 1H), 5.64 (dd, J=7.4, 4.0 Hz, 1H), 4.99 (dd, J=12.3, 7.5 Hz, 1H), 4.72-4.53 (m, 1H), 1.05 (s, 9H). LC retention time 4.21 min (analytical HPLC Method A). LC/MS (M+H): 481.

Intermediate 4E: (+.−)-2-((tert-butyldiphenylsilyl)oxy)-2-(6-chloroimidazo[1,2-b] pyridazin-2-yl)ethan-1-amine

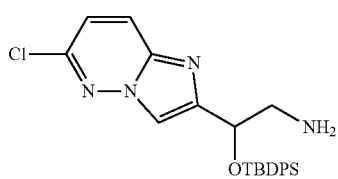
(4E)

To a slurry of (+/−)-2-(1-((tert-butyldiphenylsilyl)oxy)-2-nitroethyl)-6-chloroimidazo[1,2-b]pyridazine (1.68 g, 3.49 mmol) in a mixture of acetic acid (2.00 mL, 34.9 mmol), ethyl acetate (12 mL), THF (2.000 mL) and water (12.00 mL) at room temperature was added iron (powder, <10µ) (1.950 g, 34.9 mmol). The resulting mixture was allowed to stir at room temperature for 15 min. then was heated to 70° C. After 45 min., the mixture was cooled down to room temperature, filtered through CELITE®, rinsed with EtOAc (120 mL) and the resulting filtrate was cooled with ice bath and was treated with solid NaHCO$_3$ (20 eq, 4.10 g). Then, 50 mL of brine was added and the phases were separated and the organic portion was dried over anhydrous sodium sulfate, filtered and concentrated to afford dark tan mixture. The crude product was purified via silica gel chromatography using a 4 g silica gel cartridge and initially eluting with a linear gradient of Hex/EtOAc, then switching to DCM/MeOH to elute the product. Concentration of the fractions containing the product initially gave a foam which solidified under vacuum to afford a solid as (+/−)-2-((tert-butyldiphenylsilyl)oxy)-2-(6-chloroimidazo[1,2-b] pyridazin-2-yl)ethan-1-amine (1.29 g, 2.86 mmol, 82% yield). LC retention time 3.55 min (analytical HPLC Method A). LC/MS (M+H): 451.

Intermediates 4F and 5F: (+/−)-Cis and trans-6-((tert-butyldiphenylsilyl)oxy)-2-chloro-9-(2-(difluoromethoxy)phenyl)-6,7,8,9-tetrahydropyrido[4',3 4,5]imidazo[1,2-b]pyridazine

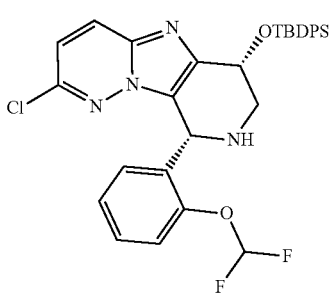
(4F)

-continued

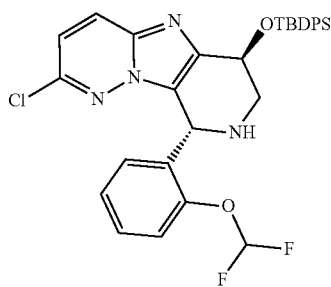

(5F)

To a slurry of (+/−)-2-((tert-butyldiphenylsilyk)oxy)-2-(6-chloroimidazo[1,2-b]pyridazin-2-yl)ethan-1-amine (1.29 g, 2.86 mmol), 2-(difluoromethoxy)benzaldehyde (1.477 g, 8.58 mmol), and anhydrous sodium sulfate (2.03 g, 14.3 mmol) in acetonitrile (6 mL) was added PPTs (5.39 g, 21.4 mmol) and the resulting mixture was deoxygenated by bubbling nitrogen through the mixture for ~5 min, then the resulting mixture was heated at 80° C. for ~16 h. The reaction mixture was cooled and concentrated under reduced pressure yielding a tan solid as the crude product mixture. This material was partitioned between EtOAc (120 mL) and aqueous saturated NaHCO$_3$ (20 mL), separated, and the aqueous portion was extracted with EtOAc (40 mL) and the combined organic extract was washed with brine, dried with sodium sulfate, filtered, and concentrated under reduced pressure to afford tan oil as crude product. This material was purified by flash chromatography using a 4 g silica gel cartridge and a linear gradient of Hex/EtOAc mixtures to afford a ~1:2 diastereomeric mixture of (+/−)-cis and trans-6-((tert-butyldiphenylsilyl)oxy)-2-chloro-9-(2-(difluoromethoxy)phenyl)-6,7,8,9-tetrahydropyrido[4',3':4,5]imidazo[1,2-b]pyridazine (1.12 g, 1.851 mmol, 64.7% yield), respectively. LC retention time 3.56 and 3.72 min (analytical HPLC Method A). LC/MS (M+H): 605.

The pure diastereomers could be resolved by SFC chromatography using the following conditions: Preparative Column: 4-ethylpyridine (5×25 cm, 5 μm, #16664); BPR pressure: 100 bars; Temperature: 40° C.; Flow rate: 250 mL/min; Mobile Phase: CO$_2$/MeOH w 0.1% NH$_4$OH (90/10); Detector Wavelength: 220 nm; Separation Program: stack injection; Injection: 0.5 mL with cycle time: 2.5 min; Sample preparation: 1.05 g/20 mL MeOH, 52.5 mg/mL; Throughput: 630 mg/hr.

Intermediate 4F: $^1$H NMR (400 MHz, methanol-d$_4$): δ 8.06 (d, J=9.5 Hz, 1H), 7.88 (dd, J=7.9, 1.6 Hz, 2H), 7.81 (dd, J=7.9, 1.6 Hz, 2H), 7.57-7.39 (m, 6H), 7.31 (d, J=7.5 Hz, 2H), 7.25 (d, J=9.5 Hz, 1H), 7.23-7.19 (m, 1H), 7.12 (d, J=7.5 Hz, 1H), 7.11-6.70 (m, 1H), 5.71 (s, 1H), 5.09 (t, J=3.5 Hz, 1H), 3.07 (dd, J=13.8, 4.3 Hz, 1H), 2.93 (dd, J=13.7, 3.3 Hz, 1H), 1.14 (s, 9H). LC retention time 3.72 min (analytical HPLC Method A). LC/MS (M+H): 605.

Intermediate 5F: $^1$H NMR (400 MHz, methanol-d$_4$) δ 8.02 (d, J=9.5 Hz, 1H), 7.86-7.76 (m, 4H), 7.50-7.31 (m, 7H), 7.29-7.20 (m, 2H), 7.01 (td, J=7.5, 1.1 Hz, 1H), 7.16-6.73 (m, 1H), 6.55 (dd, J=7.7, 1.6 Hz, 1H), 5.81-5.72 (m, 1H), 5.09 (t, J=3.2 Hz, 1H), 3.07-2.95 (m, 2H), 1.16-1.08 (m, 9H). LC retention time 3.56 min (analytical HPLC Method A). LC/MS (M+H): 605.

Intermediate 4G: (+/−)-Cis-2-chloro-9-(2-(difluoromethoxy)phenyl)-6,7,8,9-tetrahydropyrido[4',3':4,5]imidazo[1,2-b]pyridazin-6-ol

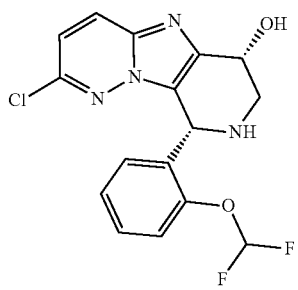

(4G)

To a solution of (+/−)-cis-6-((tert-butyldiphenylsilyl)oxy)-2-chloro-9-(2-(difluoro-methoxy)phenyl)-6,7,8,9-tetrahydropyrido[4',3':4,5]imidazo[1,2-b]pyridazine (269 mg, 0.445 mmol) in DCM (2 mL) at room temperature under nitrogen was added TBAF (1.0 in THF) (0.667 mL, 0.667 mmol) followed by stirring at room temperature for ~15 h. The mixture was then concentrated and taken up in EtOAc (50 mL), washed with water, brine, dried over anhydrous sodium sulfate, filtered and concentrated to afford the crude product which was purified via silica gel chromatography using a 4 g silica gel cartridge and a linear gradient of DCM/MeOH. Fractions containing the major product were concentrated to afford a white solid as (+/−)-2-chloro-9-(2-(difluoromethoxy)phenyl)-6,7,8,9-tetrahydropyrido-[4',3':4,5]imidazo[1,2-b]pyridazin-6-ol (156 mg, 0.425 mmol, 96% yield). $^1$H NMR (400 MHz, chloroform-d$_3$): δ 7.88 (d, J=9.5 Hz, 1H), 7.38-7.32 (m, 2H), 7.25-7.20 (m, 1H), 7.15-7.09 (m, 1H), 7.09-7.05 (m, 1H), 6.99 (d, J=9.5 Hz, 1H), 6.95-6.53 (m, 1H), 5.79 (s, 1H), 4.99 (br. s., 1H), 3.36-3.26 (m, 2H). LC retention time 1.48 min (analytical HPLC Method A). LC/MS (M+H): 367.

Example 4

A reaction vial was charged with (+/−)-cis-6-((tert-butyl-diphenylsilyl)oxy)-2-chloro-9-(2-(difluoro-methoxy)phenyl)-6,7,8,9-tetrahydropyrido[4',3':4,5]imidazo[1,2-b] pyridazine (10 mg, 0.027 mmol), (4-(2-hydroxypropan-2-yl)phenyl)boronic acid (6.38 mg, 0.035 mmol), 2M aqueous solution of potassium phosphate tribasic (0.041 mL, 0.082 mmol) and dioxane (0.3 mL). The resulting mixture was deoxygenated by bubbling nitrogen through the mixture for ~5 min, then PdCl$_2$(dppf) (0.998 mg, 1.363 μmol) was added, the vial was capped, and the mixture was heated at 105° C. for 2 h. The reaction mixture was cooled, diluted with MeOH, filtered through a Millipore (0.45 μm) filter and was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min to afford after concentration of fractions containing the product (+/−)-cis-9-(2-(difluoromethoxy) phenyl)-2-(4-(2-hydroxypropan-2-yl)phenyl)-6,7,8,9-tetrahydropyrido[4',3':4,5]imidazo[1,2-b]pyridazin-6-ol. $^1$H NMR (500 MHz, DMSO-d$_6$): δ 8.09 (d, J=9.6 Hz, 1H), 7.69 (d, J=9.6 Hz, 1H), 7.57 (d, J=8.2 Hz, 2H), 7.46 (d, J=8.3 Hz, 2H), 7.41-7.34 (m, 1H), 7.34-7.29 (m, 1H), 7.22 (br. s., 1H), 7.14-7.06 (m, 1H), 7.02 (d, J=7.5 Hz, 1H), 5.61 (s, 1H), 4.71 (br. s., 1H), 3.18-3.04 (m, 1H), 2.99 (dd, J=14.2, 4.8 Hz, 1H), 1.39 (s, 6H). LC retention time 1.41 min (Method E). LC/MS (M+H): 467.

Example 5

Example 5 was prepared from trans-6-((tert-butyldiphenylsilyl)oxy)-2-chloro-9-(2-(difluoromethoxy)phenyl)-6,7,8,9-tetrahydropyrido[4',3':4,5]imidazo[1,2-b]pyridazine according to the general method described in Example 4. ¹H NMR (500 MHz, DMSO-d₆) δ 8.13 (d, J=9.5 Hz, 1H), 7.70 (d, J=9.6 Hz, 1H), 7.62 (d, J=8.1 Hz, 2H), 7.49 (d, J=8.0 Hz, 2H), 7.38-7.32 (m, 1H), 7.29-7.24 (m, 1H), 7.43-7.09 (m, 1H), 7.06 (t, J=7.4 Hz, 1H), 6.75 (d, J=7.4 Hz, 1H), 5.70 (s, 2H), 5.37 (d, J=6.1 Hz, 1H), 5.14 (s, 1H), 4.74 (br. s., 1H), 3.13 (d, J=11.4 Hz, 1H), 2.85 (d, J=9.1 Hz, 1H), 1.41 (s, 6H). LC retention time 1.44 min (Method E). LC/MS (M+H): 467.

Examples 6 and 7

Cis-(6R,9R)-9-(2-(difluoromethoxy)phenyl)-2-(4-(2-hydroxypropan-2-yl)phenyl)-6,7,8,9-tetrahydropyrido[4',3':4,5]imidazo[1,2-b]pyridazin-6-ol, and Cis-(6S,9S)-9-(2-(difluoromethoxy)phenyl)-2-(4-(2-hydroxypropan-2-yl)phenyl)-6,7,8,9-tetrahydropyrido[4',3':4,5]imidazo[1,2-b]pyridazin-6-ol

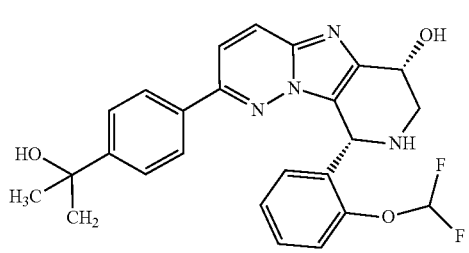

(6)

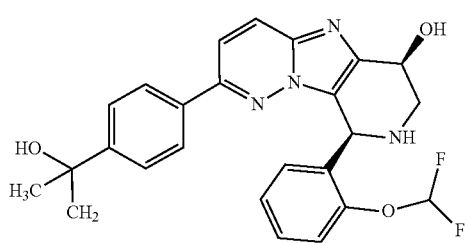

(7)

Racemic cis-9-(2-(difluoromethoxy)phenyl)-2-(4-(2-hydroxypropan-2-yl)phenyl)-6,7,8,9-tetrahydropyrido[4',3':4,5]imidazo[1,2-b]pyridazin-6-ol was resolved into its enantiomers using SFC chromatography under the following conditions: Instrument: Berger Prep SFC MGII; Column: Chiral AD 25×3 cm ID, 5 µm; Flow rate: 85.0 mL/min; Mobile Phase:85/15 CO₂/MeOH w/0.1% diethylamine; Detector Wavelength: 220 nm; Sample Prep and Injection Volume: 2000 µL of 9.1 mg dissolved in 2.5 mL MeOH.

Example 8

(+/−)-Cis-2-(4-((6S,9S)-9-(2-(difluoromethoxy)phenyl)-6-fluoro-6,7,8,9-tetrahydropyrido [4',3':4,5]imidazo[1,2-b]pyridazin-2-yl)phenyl)propan-2-ol

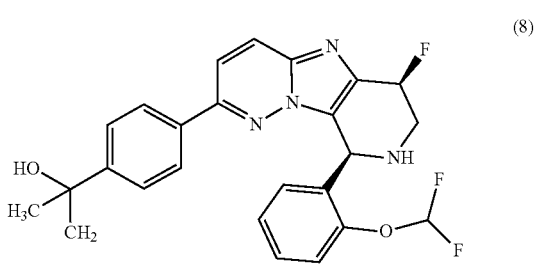 [SMILES: CC(C)(O)c1ccc(-c2ccc3nc4c(n3n2)[C@H](c2ccccc2OC(F)F)NC[C@@H]4F)cc1]

(8)

Intermediate 8A: (+/−)-Cis-2-chloro-9-(2-(difluoromethoxy)phenyl)-6-fluoro-6,7,8,9-tetrahydropyrido[4',3':4,5]imidazo[1,2-b]pyridazine

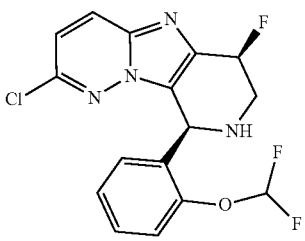

(8A)

To a solution of (+/−)-2-chloro-9-(2-(difluoromethoxy)phenyl)-6,7,8,9-tetrahydropyrido[4',3':4,5]imidazo[1,2-b]pyridazin-6-ol (231 mg, 0.63 mmol, prepared according to the general method for Intermediate 4G) in DCM (5 mL) at −78° C. was added DAST (0.42 mL, 3.15 mmol) via syringe. The resulting mixture was allowed to stir for 2 h at −78° C. The reaction was quenched by slow addition of 20% aqueous sodium carbonate (w/w, 10 mL) at this temperature and stirred for 30 min. followed by warming to room temperature. The resulting mixture was extracted with DCM (15 mL×3) and combined organic extracts were dried over anhydrous sodium sulfate, filtered and concentrated to afford a crude oil which was purified via silica gel chromatography using a 4 g silica gel column and a linear gradient of Hex/EtOAc. The fractions containing the major product were combined and concentrated to afford a white solid (69 mg, 8.14 µmol, 26% yield) as (+/−)-cis-2-(4-((6S,9S)-9-(2-(difluoromethoxy)phenyl)-6-fluoro-6,7,8,9-tetrahydropyrido [4',3':4,5]-imidazo[1,2-b]pyridazin-2-yl)phenyl)propan-2-ol. ¹H NMR (400 MHz, chloroform-d) δ 7.98 (d, J=9.5 Hz, 1H), 7.38-7.32 (m, 1H), 7.30 (s, 1H), 7.09 (d, J=9.5 Hz, 1H), 7.01 (td, J=7.4, 1.3 Hz, 1H), 6.96-6.55 (m, 1H), 6.42 (dd, J=7.6, 1.5 Hz, 1H), 5.93 (d, J=3.8 Hz, 1H), 5.75-5.53 (m, 1H), 3.43 (td, J=14.9, 2.1 Hz, 1H), 3.28-3.08 (m, 1H). LC retention time 1.49 min (analytical HPLC Method A). LC/MS (M+H): 369.

Example 8

Example 8 was prepared from (+/−)-cis-2-chloro-9-(2-(difluoromethoxy)phenyl)-6-fluoro-6,7,8,9-tetrahydropyrido[4',3':4,5]imidazo[1,2-b]pyridazine and (4-(2-hydroxypropan-2-yl)phenyl)boronic acid using the method as described for Example 4.

¹H NMR (500 MHz, DMSO-d₆) δ 8.21 (d, J=9.6 Hz, 1H), 7.80 (d, J=9.7 Hz, 1H), 7.69 (d, J=8.3 Hz, 2H), 7.51 (d, J=8.2 Hz, 2H), 7.45-7.10 (m, 3H), 7.01 (t, J=7.3 Hz, 1H), 6.55 (d, J=7.5 Hz, 1H), 5.83 (d, J=3.8 Hz, 1H), 5.75-5.55 (m, 1H), 3.35-3.00 (m, 2H), 1.40 (s, 6H). LC retention time 1.50 min (Method E). LC/MS (M+H): 469.

The following Examples in Table 1 were prepared similar to Example 8.

TABLE 1

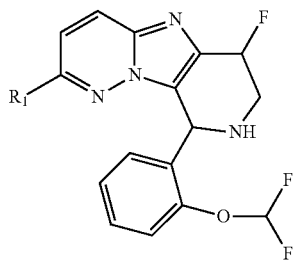

| Ex. No. | Isomer | R¹ | Rt (min) [Method] | m/z [M + H]⁺ |
|---|---|---|---|---|
| 9 | (+/−)-trans | 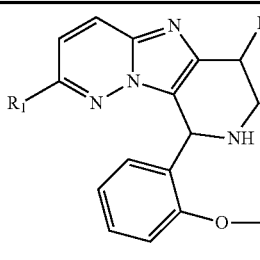 | 1.32 [E] | 469 |
| 10 | (+/−)-cis | (pyrimidin-2-yl with HO-C(CH₃)₂) | 1.32 [E] | 471 |
| 11 | (+/−)-cis | (6-methoxypyridin-3-yl) | 1.65 [E] | 442 |
| 12 | cis-(1S,4S) | (4-(2-hydroxypropan-2-yl)phenyl) | 1.56 [E] | 469 |
| 13 | cis-(1R,4R) | (4-(2-hydroxypropan-2-yl)phenyl) | 1.50 [E] | 469 |

The following Examples in Table 2 were prepared similar to Examples 4 and 5. Enantiomers, where noted, were resolved using the conditions from Examples 6 and 7.

TABLE 2

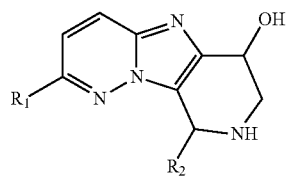

| Ex. No. | Isomer | R¹ | R² | Rt (min) Method | m/z [M + H]⁺ |
|---|---|---|---|---|---|
| 14 | trans-(6R,9S) | (4-(2-hydroxypropan-2-yl)phenyl) | (2-(difluoromethoxy)phenyl) | 1.30 [E] | 467 |

TABLE 2-continued

| Ex. No. | Isomer | R¹ | R² | Rt (min) Method | m/z [M + H]⁺ |
|---|---|---|---|---|---|
| 15 | trans-(6S,9R) | 4-(2-hydroxypropan-2-yl)phenyl | 2-(difluoromethoxy)phenyl | 1.31 [E] | 467 |
| 16 | cis-(6R,9S) | 6-methoxypyridin-3-yl | 2-(difluoromethoxy)phenyl | 1.37 [E] | 440 |
| 17 | ~1:2 diast. mixture | 2-(2-hydroxypropan-2-yl)pyrimidin-5-yl | 2-(difluoromethoxy)phenyl | 1.10/1.13 [E] | 469 |
| 18 | ~1:2 diast. mixture | 4-(3-methoxyazetidine-1-carbonyl)phenyl | 2-(difluoromethoxy)phenyl | 1.28 [E] | 522 |
| 19 | ~1:2 diast. mixture | 4-(morpholine-4-carbonyl)phenyl | 2-(difluoromethoxy)phenyl | 1.12/1.14 [E] | 522 |
| 20 | ~1:2 diast. mixture | 4-(cyclopropylcarbamoyl)phenyl | 2-(difluoromethoxy)phenyl | 0.88/0.90 [E] | 492 |

TABLE 2-continued
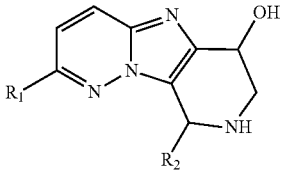
| Ex. No. | Isomer | R¹ | R² | Rt (min) Method | m/z [M + H]⁺ |
|---|---|---|---|---|---|
| 21 | ~1:2 diast. mixture | 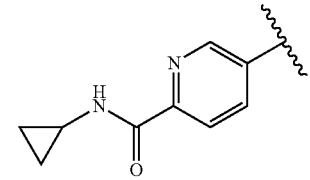 [SMILES: *c1ccc(C(=O)NC2CC2)nc1] | 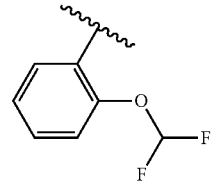 [SMILES: *c1ccccc1OC(F)F] | 0.89/0.92 [E] | 493 |
| 22 | ~1:2 diast. mixture | 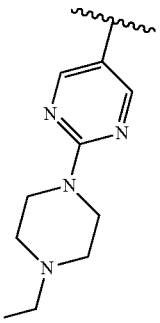 | 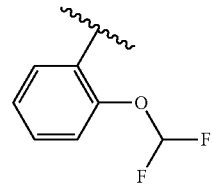 [SMILES: *c1ccccc1OC(F)F] | 0.73/0.77 [E] | 553 |
| 23 | (+/−)-trans | 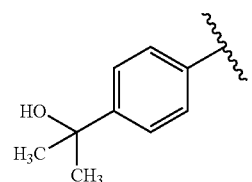 | 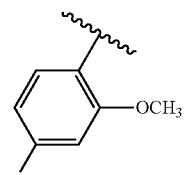 | 1.08 [O] | 449 |
| 24 | (+/−)-trans | 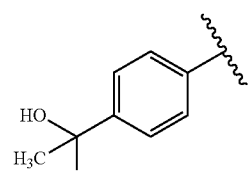 | 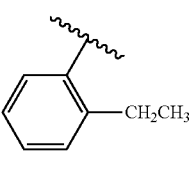 [SMILES: *c1ccccc1CC] | 1.07 [O] | 429 |
| 25 | (+/−)-cis | 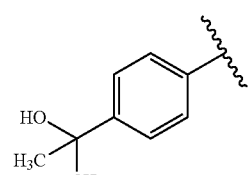 | 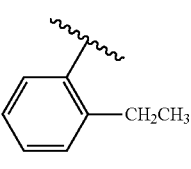 [SMILES: *c1ccccc1CC] | 1.21 [O] | 429 |
| 26 | ~1:2 diast. mixture | 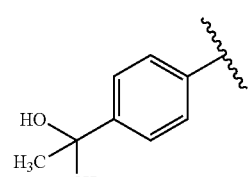 | 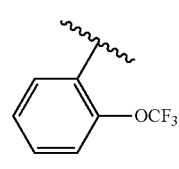 [SMILES: *c1ccccc1OC(F)(F)F] | 1.07/1.09 [O] | 485 |

TABLE 2-continued
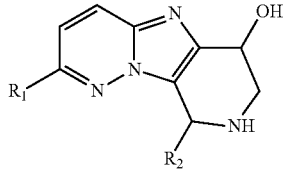
| Ex. No. | Isomer | R¹ | R² | Rt (min) Method | m/z [M + H]⁺ |
|---|---|---|---|---|---|
| 27 | (+/−)-cis | 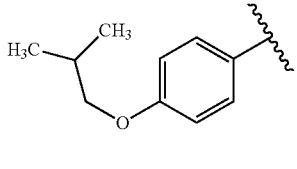 [SMILES: *c1ccc(OCC(C)C)cc1] | 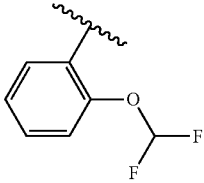 [SMILES: *c1ccccc1OC(F)F] | 1.98 [E] | 481 |
| 28 | (+/−)-trans | 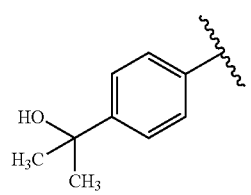 [SMILES: *c1ccc(C(C)(C)O)cc1] | 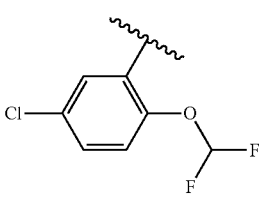 [SMILES: *c1cc(Cl)ccc1OC(F)F] | 1.12 [O] | 502 |
| 29 | (+/−)-cis | 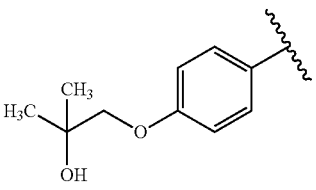 [SMILES: *c1ccc(OCC(C)(C)O)cc1] | 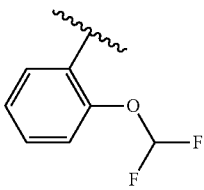 [SMILES: *c1ccccc1OC(F)F] | 1.35 [E] | 497 |
| 30 | (+/−)-cis | 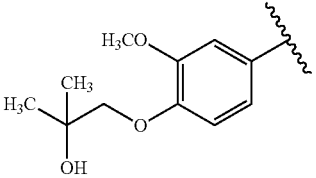 [SMILES: *c1ccc(OCC(C)(C)O)c(OC)c1] | 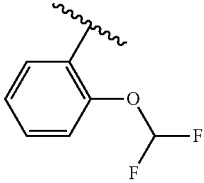 [SMILES: *c1ccccc1OC(F)F] | 1.31 [E] | 527 |
| 31 | (+/−)-cis | 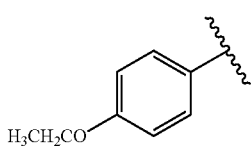 | 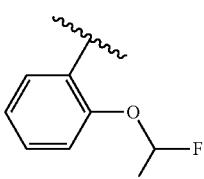 | 1.64 [E] | 453 |
| 32 | (+/−)-cis | 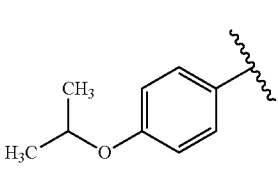 [SMILES: *c1ccc(OC(C)C)cc1] | 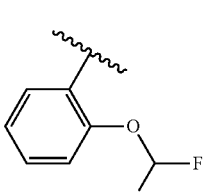 | 1.84 [E] | 467 |
| 33 | (+/−)-cis | 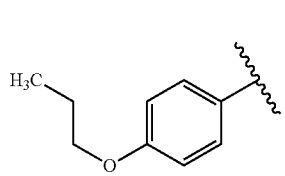 [SMILES: *c1ccc(OCCC)cc1] | 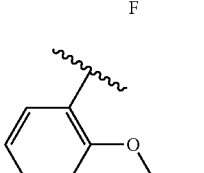 | 1.94 [E] | 467 |

TABLE 2-continued
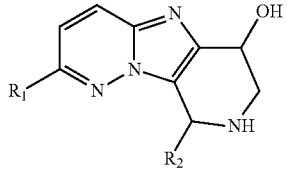
| Ex. No. | Isomer | R¹ | R² | Rt (min) Method | m/z [M + H]⁺ |
|---|---|---|---|---|---|
| 34 | (+/−)-cis | 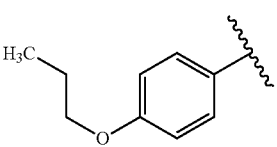 [SMILES: *c1ccc(OCCC)cc1] | 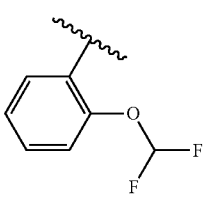 [SMILES: *c1ccccc1OC(F)F] | 1.65 [E] | 483 |
| 35 | (+/−)-cis | 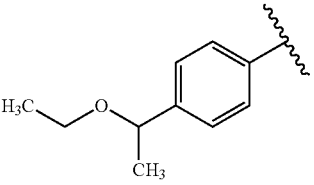 [SMILES: *c1ccc(C(C)OCC)cc1] | 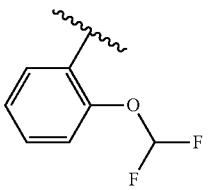 [SMILES: *c1ccccc1OC(F)F] | 1.84 [E] | 481 |
| 36 | (+/−)-cis | 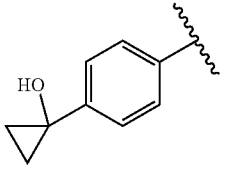 [SMILES: *c1ccc(C2(O)CC2)cc1] | 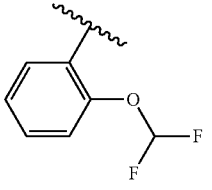 [SMILES: *c1ccccc1OC(F)F] | 1.62 [E] | 465 |
| 37 | (+/−)-cis | 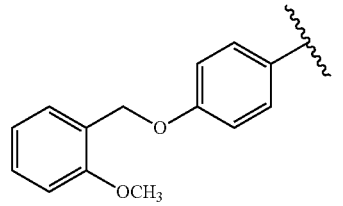 [SMILES: *c1ccc(OCc2ccccc2OC)cc1] | 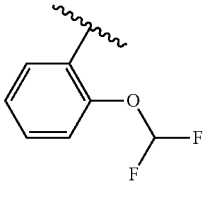 [SMILES: *c1ccccc1OC(F)F] | 2.10 [E] | 545 |
| 38 | (+/−)-trans | 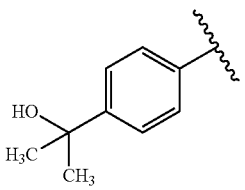 [SMILES: *c1ccc(C(C)(C)O)cc1] | 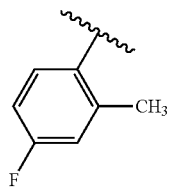 [SMILES: *c1ccc(F)cc1C] | 1.19 [O] | 433 |
| 39 | (+/−)-cis | 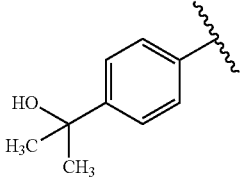 [SMILES: *c1ccc(C(C)(C)O)cc1] | 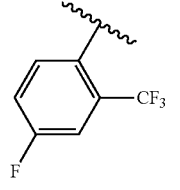 | 1.23 [O] | 487 |

TABLE 2-continued

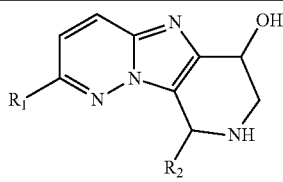

| Ex. No. | Isomer | R¹ | R² | Rt (min) Method | m/z [M + H]⁺ |
|---|---|---|---|---|---|
| 40 | (+/−)-cis | 4-(N-methylsulfamoyl)phenyl | 2-(difluoromethoxy)phenyl | 1.31 [E] | 502 |
| 41 | (+/−)-cis | 4-(methylsulfonyl)phenyl | 2-(difluoromethoxy)phenyl | 1.29 [E] | 487 |
| 42 | (+/−)-cis | 4-(neopentyloxy)phenyl | 2-(difluoromethoxy)phenyl | 2.01 [E] | 495 |
| 43 | (+/−)-cis | 4-(2-hydroxypropan-2-yl)phenyl | 4-fluoro-2-methylphenyl | 1.51 [E] | 494 |
| 44 | (+/−)-trans | 4-(2-hydroxypropan-2-yl)phenyl | 4-fluoro-2-(trifluoromethyl)phenyl | 1.18 [E] | 488 |
| 45 | (+/−)-cis | 4-morpholinophenyl | 2-(difluoromethoxy)phenyl | 1.42 [E] | 495 |
| 46 | (+/−)-cis | 4-sulfamoylphenyl | 2-(difluoromethoxy)phenyl | 1.23 [E] | 488 |

TABLE 2-continued

| Ex. No. | Isomer | R¹ | R² | Rt (min) Method | m/z [M + H]⁺ |
|---|---|---|---|---|---|
| 47 | (+/−)-cis | 3-chloro-4-(morpholine-4-carbonyl)phenyl | 2-(difluoromethoxy)phenyl | 1.71 [E] | 557 |
| 48 | (+/−)-cis | 4-carbamoyl-3-chlorophenyl | 2-(difluoromethoxy)phenyl | 1.51 [E] | 487 |
| 49 | (+/−)-cis | 4-(3-hydroxypentan-3-yl)phenyl | 2-(difluoromethoxy)phenyl | 1.18 [E] | 496 |
| 50 | (+/−)-cis | 4-(2-hydroxybutan-2-yl)phenyl | 2-(difluoromethoxy)phenyl | 1.63 [E] | 482 |
| 51 | (+/−)-trans | 6-methoxypyridin-3-yl | 2-(difluoromethoxy)phenyl | 1.04/1.24 [E] | 440 |
| 52 | (+/−)-trans | 4-(2-hydroxy-2-methylpropoxy)phenyl | 2-(difluoromethoxy)phenyl | 1.45/1.30 [E] | 498 |
| 53 | (+/−)-trans | 4-(2-hydroxypropan-2-yl)phenyl | 2,5-dimethylphenyl | 1.30 [O] | 430 |

TABLE 2-continued

| Ex. No. | Isomer | R¹ | R² | Rt (min) Method | m/z [M + H]⁺ |
|---|---|---|---|---|---|
| 54 | (+/−)-cis | 4-(2-hydroxypropan-2-yl)phenyl | 5-chloro-2-(difluoromethoxy)phenyl | 1.12 [O] | 502 |
| 55 | (+/−)-trans | 4-(2-hydroxypropan-2-yl)phenyl | 5-chloro-2-(trifluoromethyl)phenyl | 1.33 [O] | 504 |
| 56 | (+/−)-trans | 4-(2-hydroxypropan-2-yl)phenyl | 5-chloro-2-methoxyphenyl | 1.29 [O] | 466 |

Example 57

Rac-(6S,9S)-9-(2-(difluoromethoxy)phenyl)-2-(4-(2-hydroxypropan-2-yl)phenyl)-7,9-dihydro-6H-pyrano[4',3':4,5]imidazo[1,2-b]pyridazin-6-ol

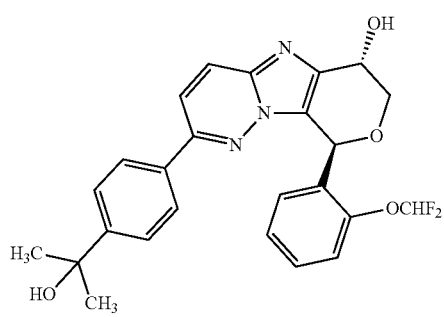

(57)

Intermediate 57A: Methyl 6-chloro-3-((2-(difluoromethoxy)phenyl)(hydroxy)-methy)imidazo[1,2-b]pyridazine-2-carboxylate

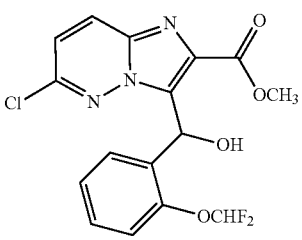

(57A)

A clear light tan solution of ethyl 6-chloroimidazo[1,2-b]pyridazine-2-carboxylate (6.5 g, 28.8 mmol) in tetrahydrofuran (150 mL) was cooled to −78° C. in an acetone/dry ice bath, to form a light tan slurry. A 1 M tetrahydrofuran/toluene solution of lithium magnesium 2,2,6,6-tetramethylpiperidin-1-ide dichloride (36.0 mL, 36.0 mmol) was added dropwise to generate a clear light tan solution. After stirring at −78° C. for 3 h, a solution of 2-(difluoromethoxy)benzaldehyde (5.21 g, 30.2 mmol) in tetrahydrofuran (20 mL) was added via syringe. The resulting mixture was stirred at −78° C. for 5 h. The reaction was quenched with methanol (10 mL) and the mixture was warmed to room temperature. The brown precipitate was filtered and washed with tetrahydrofuran (10 mL). The filtrate was concentrated. The residue was diluted with ethyl acetate (200 mL), washed with water (20 mL), brine (20 mL), dried (magnesium sulfate), filtered and concentrated under reduced pressure. Silica gel chromatography, eluting with 20-60% ethyl acetate in hexanes, gave methyl 6-chloro-3-((2-(difluoromethoxy)phenyl)(hydroxy) methyl)imidazo[1,2-b]pyridazine-2-carboxylate (2.40 g, 22% yield). LC/MS (M+1): 284.1; HPLC retention time: 0.81 min (analytical HPLC Method C); $^1$H NMR (400 MHz, CDCl$_3$) δ 7.96 (d, J=9.7 Hz, 1H), 7.60 (dd, J=7.7, 1.5 Hz, 1H), 7.37-7.26 (m, 1H), 7.25-7.13 (m, 2H), 7.09 (dd, J=8.0, 1.0 Hz, 1H), 6.90 (d, J=11.7 Hz, 1H), 6.74-6.17 (m, 1H), 5.78 (d, J=11.7 Hz, 1H), 4.03 (s, 3H).

Intermediate 57B: 6-Chloro-3-((2-(difluoromethoxy)phenyl)(hydroxy)methyl)imidazo [1,2-b]pyridazine-2-carbaldehyde

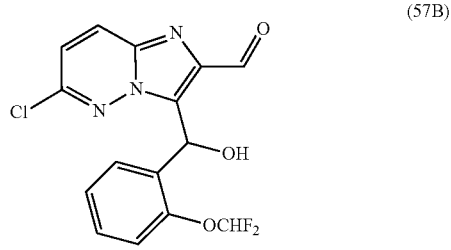 [SMILES: O=Cc1nc2ccc(Cl)nn2c1C(O)c1ccccc1OC(F)F]

(57B)

A 1.0 M dichloromethane solution of diisobutylaluminum hydride (7.04 mL, 7.04 mmol) was added dropwise to a stirred mixture of methyl 6-chloro-3-((2-(difluoromethoxy)phenyl)(hydroxy)methyl)imidazo[1,2-b]pyridazine-2-carboxylate (900 mg, 2.35 mmol) in dichloromethane (30 mL) at −78° C. After stirring for additional 2h at that temperature, the reaction was quenched with sodium sulfate decahydrate (10 g). The mixture was warmed to room temperature and filtered. The filter cake was washed with dichloromethane (30 mL). The filtrate was concentrated under reduced pressure. Silica gel chromatography, eluting with 0-10% methanol in dichloromethane, gave 6-chloro-3-((2-(difluoromethoxy)phenyl)(hydroxy)methyl)imidazo[1,2-b]pyridazine-2-carbaldehyde (410 mg, 49% yield). LC/MS (M+1): 354.0; HPLC retention time: 0.78 min (analytical HPLC Method C); $^1$H NMR (400 MHz, DMSO-d$_6$) δ 10.17 (s, 1H), 8.31 (d, J=9.5 Hz, 1H), 7.89 (dd, J=7.5, 1.5 Hz, 1H), 7.50 (d, J=9.7 Hz, 1H), 7.41-7.24 (m, 2H), 7.17-6.95 (m, 2H), 6.81 (d, J=6.5 Hz, 1H), 6.66 (br. s., 1H).

Intermediate 57C: (6-Chloro-2-vinylimidazo[1,2-b]pyridazin-3-yl)(2-(difluoromethoxy) phenyl)methanol

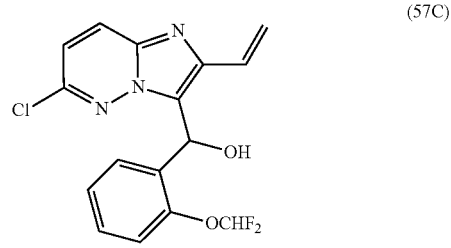 [SMILES: C=Cc1nc2ccc(Cl)nn2c1C(O)c1ccccc1OC(F)F]

(57C)

A 0.5 M toluene solution of KHMDS (6.03 mL, 3.01 mmol) was added dropwise to a stirred mixture of methyltriphenylphosphonium bromide (994 mg, 2.78 mmol) in tetrahydrofuran (20 mL) at room temperature. After stirring for 30 minutes, a solution of 6-chloro-3-((2-(difluoromethoxy)phenyl)(hydroxy)methyl)imidazo[1,2-b]pyridazine-2-carbaldehyde (410 mg, 1.16 mmol) in tetrahydrofuran (5 mL) was added. After stirring for 1 h, the mixture was quenched with saturated ammonium chloride (10 mL), diluted with ethyl acetate (200 mL), washed with water (20 mL), brine (20 mL), dried (magnesium sulfate), filtered and concentrated under reduced pressure. Silica gel chromatography, eluting with 20-70% ethyl acetate in hexanes, gave (6-chloro-2-vinylimidazo[1,2-b]pyridazin-3-yl)(2-(difluoromethoxy)phenyl)methanol (265 mg, 65% yield). LC/MS (M+1): 352.0; HPLC retention time: 0.81 min (analytical HPLC Method C); $^1$H NMR (400 MHz, CD$_3$OD) δ 7.98-7.83 (m, 2H), 7.40-7.14 (m, 3H), 7.08 (d, J=7.8 Hz, 1H), 6.88-6.73 (m, 2H), 6.71-6.26 (m, 1H), 6.10 (dd, J=17.4, 1.7 Hz, 1H), 5.29 (dd, J=11.1, 1.8 Hz, 1H).

Intermediate 57D: 1-(6-Chloro-3-((2-(difluoromethoxy)phenyl)(hydroxy)methyl)imidazo [1,2-b]pyridazin-2-yl)ethane-1,2-diol

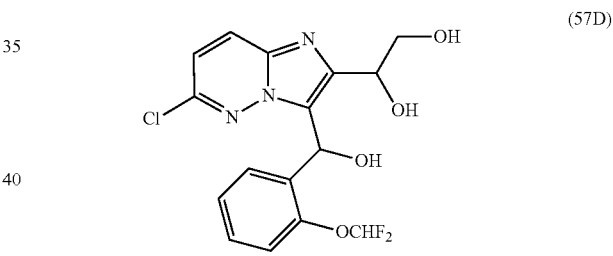

(57D)

A 2.5% 2-propanol solution of osmium tetroxide (0.139 mL, 0.011 mmol) and NMO (195 mg, 1.66 mmol) was added to a mixture of (6-chloro-2-vinylimidazo[1,2-b]pyridazin-3-yl)(2-(difluoromethoxy)phenyl)methanol (195 mg, 0.554 mmol) in acetone (6 mL) and water (1 mL) at room temperature. After stirring for 15 h, the reaction was quenched with saturated ammonium chloride (2 mL), diluted with ethyl acetate (100 mL), washed with water (10 mL), brine (10 mL), dried (magnesium sulfate), filtered and concentrated under reduced pressure. Silica gel chromatography, eluting with 0-10% methanol in dichloromethane, gave 1-(6-chloro-3-((2-(difluoromethoxy)phenyl)(hydroxy)methypimidazo[1,2-b]pyridazin-2-yl)ethane-1,2-diol (97 mg, 45% yield). LC/MS (M+1): 386.1; HPLC retention time: 0.67 min (analytical HPLC Method C); $^1$H NMR (400 MHz, CD$_3$OD) δ 8.05-7.96 (m, 1H), 7.92-7.71 (m, 1H), 7.41-7.23 (m, 3H), 7.22-6.98 (m, 1H), 6.86-6.35 (m, 2H), 4.94 (dd, J=7.5, 4.6 Hz, 1H), 3.83-3.65 (m, 2H).

Intermediates 57E-trans and 57E-cis: Trans-2-chloro-9-(2-(difluoromethoxy)phenyl)-6,9-dihydro-7H-pyrano[4',3':4,5]imidazo[1,2-b]pyridazin-6-ol, and Cis-2-chloro-9-(2-(difluoromethoxy)phenyl)-6,9-dihydro-7H-pyrano[4',3':4,5]imidazo[1,2-b]pyridazin-6-ol

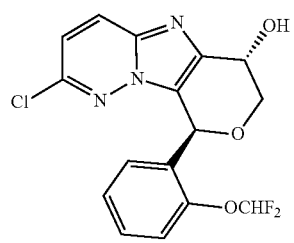
(57E-trans)

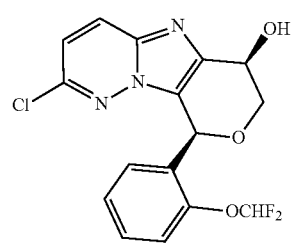
(57E-cis)

A mixture of 1-(6-chloro-3-((2-(difluoromethoxy)phenyl)(hydroxy)methyl) imidazo[1,2-b]pyridazin-2-yl)ethane-1,2-diol (90 mg, 0.233 mmol) and p-toluenesulfonic acid (4.44 mg, 0.023 mmol) in toluene (2 mL) was heated to 90° C. for 3 h. The mixture was cooled to room temperature, diluted with ethyl acetate (60 mL), washed with saturated sodium bicarbonate (10 mL), water (10 mL), brine (10 mL), dried (magnesium sulfate), filtered and concentrated under reduced pressure. Supercritical fluid chromatography (4-ethylpyridine column, 35° C., CO2/MeOH (90/10)) gave cis-2-chloro-9-(2-(difluoromethoxy)phenyl)-6,9-dihydro-7H-pyrano[4',3':4,5]imidazo[1,2-b] pyridazin-6-ol (20 mg, 23% yield). LC/MS (M+1): 368.0; HPLC retention time: 0.78 min (analytical HPLC Method C); $^1$H NMR (400 MHz, CD$_3$OD) δ 8.04 (d, J=9.5 Hz, 1H), 7.44 (td, J=7.8, 1.7 Hz, 1H), 7.33-7.24 (m, 3H), 7.23-7.16 (m, 1H), 7.16-6.72 (m, 1H), 6.40 (s, 1H), 4.92-4.88 (m, 1H), 4.24-4.00 (m, 2H). Trans-2-chloro-9-(2-(difluoromethoxy)phenyl)-6,9-dihydro-7H-pyrano[4',3':4,5]imidazo[1,2-b]pyridazin-6-ol was also obtained (30 mg, 35% yield): LC/MS (M+1): 368.0; HPLC retention time: 0.76 min (analytical HPLC Method C); $^1$H NMR (400 MHz, CD$_3$OD) δ 8.08 (d, J=9.5 Hz, 1H), 7.51-7.38 (m, 1H), 7.33-7.26 (m, 2H), 7.14 (t, J=7.5 Hz, 1H), 7.11-6.67 (m, 2H), 6.51 (s, 1H), 4.94 (t, J=3.9 Hz, 1H), 4.12 (dd, J=12.2, 3.5 Hz, 1H), 3.86 (dd, J=12.2, 4.2 Hz, 1H).

Example 57

A mixture of trans-2-chloro-9-(2-(difluoromethoxy)phenyl)-7,9-dihydro-6H-pyrano[4',3':4,5]imidazo[1,2-b]pyridazin-6-ol (6 mg, 0.016 mmol), (4-(2-hydroxypropan-2-yl)phenyl)boronic acid (3.52 mg, 0.020 mmol), PdCl$_2$(dppf)-CH$_2$Cl$_2$ adduct (2.66 mg, 3.26 μmol) and 2.0 M aqueous potassium phosphate (0.016 mL, 0.033 mmol) in N,N-dimethylformamide (0.8 mL) was degassed with nitrogen in a sealed vial and heated to 90° C. for 2 h. The mixture was cooled to room temperature and purified via preparative LC/MS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-100% B over 20 minutes, then a 5-minute hold at 100% B; Flow: 20 mL/min. Fractions containing the product were combined and dried via centrifugal evaporation to give rac-(6S,9S)-9-(2-(difluoromethoxy)phenyl)-2-(4-(2-hydroxypropan-2-yl)phenyl)-7,9-dihydro-6H-pyrano[4',3':4,5]imidazo[1,2-b]pyridazin-6-ol (2.6 mg, 34% yield). LC/MS (M+1): 468.1; HPLC RT=1.48 min (analytical HPLC Method A). $^1$H NMR (500 MHz, DMSO-d$_6$) δ 8.18 (d, J=9.6 Hz, 1H), 7.76 (d, J=9.7 Hz, 1H), 7.64 (d, J=8.2 Hz, 2H), 7.55-7.42 (m, 3H), 7.42-7.20 (m, 2H), 7.20-7.10 (m, 1H), 6.93 (d, J=7.3 Hz, 1H), 6.44 (s, 1H), 4.87 (d, J=4.6 Hz, 1H), 4.11-3.98 (m, 1H), 3.73 (dd, J=11.9, 5.2 Hz, 1H), 1.41 (s, 6H).

Example 58

Cis-9-(2-(difluoromethoxy)phenyl)-2-(4-(2-hydroxypropan-2-yl)phenyl)-6,9-dihydro-7H-pyrano[4',3':4,5]imidazo[1,2-b]pyridazin-6-ol

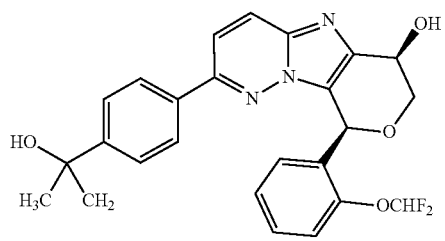
(58)

Example 58 was prepared according to the general procedure described for the preparation of Intermediate 57F. Cis-2-chloro-9-(2-(difluoromethoxy)phenyl)-7,9-dihydro-6H-pyrano[4',3':4,5]imidazo[1,2-b]pyridazin-6-ol (6 mg, 0.016 mmol) was treated with (4-(2-hydroxypropan-2-yl)phenyl)boronic acid (3.52 mg, 0.020 mmol) to provide cis-9-(2-(difluoromethoxy)phenyl)-2-(4-(2-hydroxypropan-2-yl)phenyl)-6,9-dihydro-7H-pyrano[4',3':4,5]imidazo[1,2-b]pyridazin-6-ol (1.8 mg, 24% yield). LC/MS (M+1): 468.1; HPLC RT=1.46 min (analytical HPLC Method A). $^1$H NMR (500 MHz, DMSO-d$_6$) δ 8.15 (d, J=9.5 Hz, 1H), 7.75 (d, J=9.4 Hz, 1H), 7.64 (d, J=8.1 Hz, 2H), 7.52-7.41 (m, 3H), 7.41-7.22 (m, 3H), 7.22-7.14 (m, 1H), 6.34 (s, 1H), 5.70 (d, J=6.1 Hz, 1H), 4.74 (br. s., 1H), 4.04 (br. s., 2H), 1.42 (s, 6H).

Example 59

9-(2-(Difluoromethoxy)phenyl)-2-(4-(2-hydroxypropan-2-yl)phenyl)-6-methyl-6,9-dihydro-7H-pyrano[4',3':4,5]imidazo[1,2-b]pyridazin-6-ol

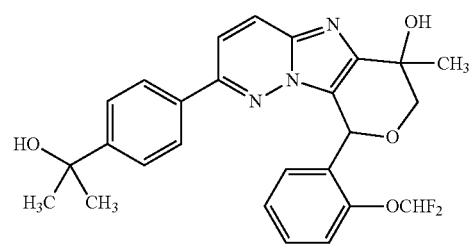
(59)

Intermediate 59A: 2-Chloro-9-(2-(difluoromethoxy) phenyl)-6,9-dihydro-7H-pyrano [4',3':4,5]imidazo[1, 2-b]pyridazin-6-ol

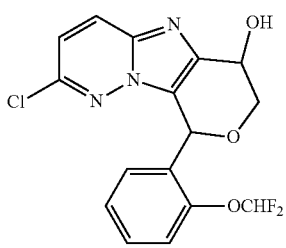

(59A)

A mixture of 1-(6-chloro-3-((2-(difluoromethoxy)phenyl) (hydroxy)methyl) imidazo[1,2-b]pyridazin-2-yl)ethane-1,2-diol (90 mg, 0.233 mmol) and p-toluenesulfonic acid (4.44 mg, 0.023 mmol) in toluene (2 mL) was heated to 90° C. for 3 h. The mixture was cooled to room temperature, diluted with ethyl acetate (60 mL), washed with saturated sodium bicarbonate (10 mL), water (10 mL), brine (10 mL), dried (magnesium sulfate), filtered and concentrated under reduced pressure. Silica gel chromatography, eluting with 0-10% methanol in dichloromethane, gave 2-chloro-9-(2-(difluoromethoxy) phenyl)-6,9-dihydro-7H-pyrano[4',3':4, 5]imidazo[1,2-b]pyridazin-6-ol (60 mg, 70% yield). LC/MS (M+1): 368.0; HPLC retention time: 0.78 min (analytical HPLC Method C); $^1$H NMR (400 MHz, CD$_3$OD) δ 8.04 (d, J=9.5 Hz, 1H), 7.44 (td, J=7.8, 1.7 Hz, 1H), 7.33-7.24 (m, 3H), 7.23-7.16 (m, 1H), 7.16-6.72 (m, 1H), 6.40 (s, 1H), 4.92-4.88 (m, 1H), 4.24-4.00 (m, 2H).

Intermediate 59B: 2-Chloro-9-(2-(difluoromethoxy) phenyl)-7H-pyrano[4',3':4,5]imidazo [1,2-b] pyridazin-6(9H)-one

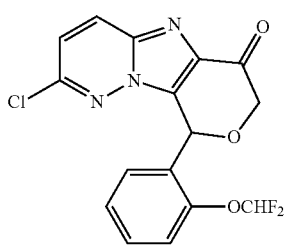

(59B)

Dess-Martin periodinane (69.2 mg, 0.163 mmol) was added to a mixture of 2-chloro-9-(2-(difluoromethoxy)phenyl)-7,9-dihydro-6H-pyrano[4',3':4,5]imidazo[1,2-b] pyridazin-6-ol (40 mg, 0.109 mmol) in dichloromethane (2 mL) at room temperature. After stirring for 2 h, the reaction was quenched with saturated sodium bicarbonate (1 mL). The mixture was diluted with ethyl acetate (100 mL), washed with water (10 mL), brine (10 mL), dried (magnesium sulfate), filtered and concentrated under reduced pressure. Silica gel chromatography, eluting with 20-80% ethyl acetate in hexanes, gave 2-chloro-9-(2-(difluoromethoxy) phenyl)-7H-pyrano[4',3':4,5]imidazo[1,2-b] pyridazin-6 (9H)-one (30 mg, 75% yield). LC/MS (M+1): 366.0; HPLC retention time: 0.83 min (analytical HPLC Method C); $^1$H NMR (400 MHz, CDCl$_3$) δ 8.06-7.95 (m, 1H), 7.49-7.34 (m, 1H), 7.26-7.19 (m, 1H), 7.24-7.07 (m, 2H), 7.01 (dd, J=7.7, 1.5 Hz, 1H), 6.85-6.39 (m, 2H), 4.49-4.26 (m, 2H).

Intermediate 59C: 2-Chloro-9-(2-(difluoromethoxy) phenyl)-6-methyl-6,9-dihydro-7H-pyrano[4',3':4,5] imidazo[1,2-b]pyridazin-6-ol

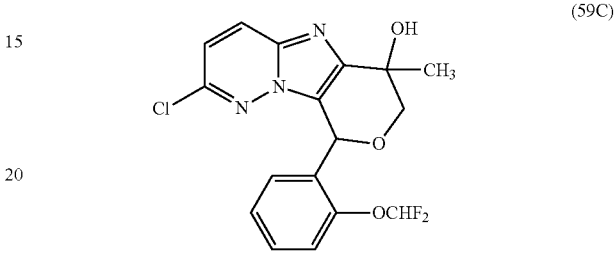

(59C)

A 3.0 M ether solution of methylmagnesium bromide (0.027 mL, 0.082 mmol) was added to a mixture of 2-chloro-9-(2-(difluoromethoxy)phenyl)-7,9-dihydro-6H-pyrano[4', 3':4,5]imidazo[1,2-b]pyridazin-6-one (10 mg, 0.027 mmol) in tetrahydrofuran (1 mL) at 0° C. After stirring at that temperature for 30 minutes, the reaction was quenched with saturated sodium bicarbonate (1 mL). The mixture was diluted with ethyl acetate (100 mL), washed with water (10 mL), brine (10 mL), dried (magnesium sulfate), filtered and concentrated under reduced pressure. Silica gel chromatography, eluting with 0-10% methanol in dichloromethane, gave 2-chloro-9-(2-(difluoromethoxy)phenyl)-6-methyl-6, 9-dihydro-7H-pyrano[4',3':4,5]imidazo[1,2-b]pyridazin-6-ol as a 3:2 mixture of two diastereomers (6 mg, 58% yield). LC/MS (M+1): 382.0; HPLC retention time: 0.80 min (analytical HPLC Method C); $^1$H NMR (400 MHz, CD$_3$OD) δ 8.20-7.93 (m, 1H), 7.57-7.37 (m, 1H), 7.41-7.23 (m, 2H), 7.16 (dd, J=7.6, 6.5 Hz, 1H), 7.05-6.65 (m, 2H), 6.54-6.38 (m, 1H), 4.06-3.73 (m, 2H), 1.67 (d, J=15.5 Hz, 3H).

Example 59

Example 59 was prepared according to the general procedure described for the preparation of Example 57. 2-Chloro-9-(2-(difluoromethoxy)phenyl)-6-methyl-6,9-dihydro-7H-pyrano[4',3':4,5]imidazo[1,2-b]pyridazin-6-ol (6 mg, 0.016 mmol) was treated with (4-(2-hydroxypropan-2-yl)phenyl)boronic acid (3.39 mg, 0.019 mmol) to provide 9-(2-(difluoromethoxy) phenyl)-2-(4-(2-hydroxypropan-2-yl)phenyl)-6-methyl-6,9-dihydro-7H-pyrano[4',3':4,5]imidazo[1,2-b]pyridazin-6-ol as a 3:2 mixture of two diastereomers (4.6 mg, 49% yield). LC/MS (M+1): 482.1; HPLC RT=0.74 min (analytical HPLC Method C); $^1$H NMR (400 MHz, CD$_3$OD) δ 8.46-8.22 (m, 1H), 8.20-8.01 (m, 1H), 7.76-7.64 (m, 2H), 7.64-7.46 (m, 3H), 7.46-7.32 (m, 2H), 7.32-7.14 (m, 2H), 7.12-6.68 (m, 1H), 6.53 (d, J=12.1 Hz, 1H), 4.24-3.86 (m, 2H), 1.86-1.65 (m, 3H), 1.55 (d, J=2.6 Hz, 6H).

Example 60

9-(2-(Difluoromethoxy)phenyl)-2-(4-(2-hydroxypropan-2-yl)phenyl)-6-(pyridin-4-yl)-6,9-dihydro-7H-pyrano[4',3':4,5]imidazo[1,2-b]pyridazin-6-ol

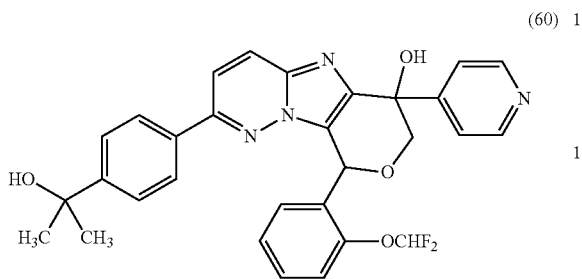

(60)

Intermediate 60A: 2-Chloro-9-(2-(difluoromethoxy)phenyl)-6-(pyridin-4-yl)-6,9-dihydro-7H-pyrano[4',3':4,5]imidazo[1,2-b]pyridazin-6-ol

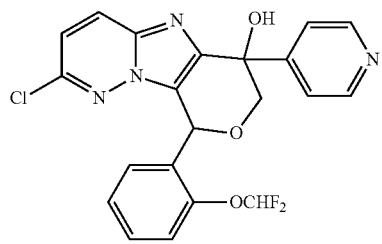

(60A)

A 1.0 M hexanes solution of n-butyllithium (0.051 mL, 0.082 mmol) was added to a mixture of 4-iodopyridine (16.7 mg, 0.082 mmol) in tetrahydrofuran (1 mL) at —78° C. After stirring at —78° C. for 10 minutes, the resulting mixture was added a solution of 2-chloro-9-(2-(difluoromethoxy)phenyl)-7,9-dihydro-6H-pyrano[4',3':4,5]imidazo[1,2-b]pyridazin-6-one (10 mg, 0.027 mmol) in tetrahydrofuran (0.5 mL). The resultant mixture was stirred at —78° C. for 30 minutes, quenched with methanol (0.5 mL), warmed to room temperature and concentrated. Silica gel chromatography, eluting with 0-5% methanol in dichloromethane, gave 2-chloro-9-(2-(difluoromethoxy)phenyl)-6-(pyridin-4-yl)-6,9-dihydro-7H-pyrano[4',3':4,5]imidazo[1,2-b]pyridazin-6-ol as a 4:1 mixture of two diastereomers (6 mg, 49% yield). LC/MS (M+1): 445.1; HPLC retention time: 0.67 min (analytical HPLC Method C); $^1$H NMR (400 MHz, CD$_3$OD) δ 8.61-8.50 (m, 2H), 8.04 (d, J=9.5 Hz, 1H), 7.69-7.64 (m, 2H), 7.56-7.44 (m, 1H), 7.39-7.29 (m, 2H), 7.21 (td, J=7.5, 1.0 Hz, 1H), 7.12-7.04 (m, 1H), 7.00-6.67 (m, 1H), 6.63 (s, 1H), 4.11-4.05 (m, 1H), 4.03-3.89 (m, 1H).

Intermediate 60B: 9-(2-(Difluoromethoxy)phenyl)-2-(4-(2-hydroxypropan-2-yl)phenyl)-6-(pyridin-4-yl)-6,9-dihydro-7H-pyrano[4',3':4,5]imidazo[1,2-b]pyridazin-6-ol

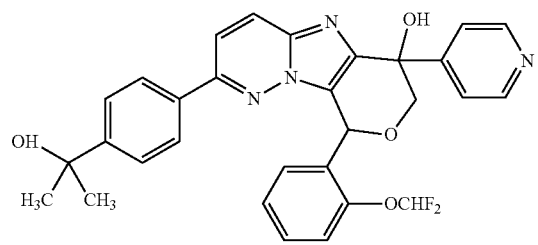

(60B)

Following similar conditions as described for the preparation of Example 57, 2-chloro-9-(2-(difluoromethoxy)phenyl)-6-(pyridin-4-yl)-7,9-dihydro-6H-pyrano[4',3':4,5]imidazo[1,2-b]pyridazin-6-ol (6 mg, 0.013 mmol) was treated with (4-(2-hydroxypropan-2-yl)phenyl)boronic acid (2.91 mg, 0.016 mmol) to provide 9-(2-(difluoromethoxy)phenyl)-2-(4-(2-hydroxypropan-2-yl)phenyl)-6-(pyridin-4-yl)-6,9-dihydro-7H-pyrano [4',3':4,5]imidazo[1,2-b]pyridazin-6-ol as a 4:1 mixture of two diastereomers (3.6 mg, 37% yield). LC/MS (M+1): 545.3; HPLC RT=0.69 min (analytical HPLC Method C); $^1$H NMR (400 MHz, CD$_3$OD) δ 8.83 (d, J=5.4 Hz, 2H), 8.55-8.20 (m, 2H), 8.11-7.98 (m, 1H), 7.91-7.79 (m, 1H), 7.73-7.48 (m, 5H), 7.42-7.21 (m, 3H), 6.91-6.55 (m, 2H), 4.44-4.12 (m, 2H), 1.60-1.47 (m, 6H).

Example 61

Cis-9-(2-(difluoromethoxy)phenyl)-2-(2-(2-hydroxypropan-2-yl)pyrimidin-5-yl)-6,9-dihydro-7H-pyrano[4',3':4,5]imidazo[1,2-b]pyridazin-6-ol

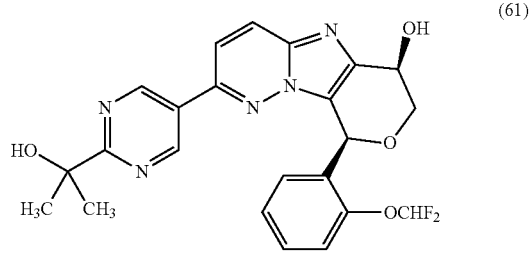 [SMILES: CC(C)(O)c1ncc(-c2ccc3nc4c(n3n2)[C@H](c2ccccc2OC(F)F)OC[C@@H]4O)cn1]

(61)

Example 61 was prepared according to the general procedure for the preparation of Example 57: Cis-2-chloro-9-(2-(difluoromethoxy)phenyl)-7,9-dihydro-6H-pyrano [4',3':4,5]imidazo[1,2-b]pyridazin-6-ol (8 mg, 0.022 mmol) was treated with 2-(5-(4,4,5,5-tetramethyl-1,3,2-dioxaborolan-2-yl)pyrimidin-2-yl)propan-2-ol (6.90 mg, 0.026 mmol) to provide cis-9-(2-(difluoromethoxy)phenyl)-2-(2-(2-hydroxypropan-2-yl) pyrimidin-5-yl)-6,9-dihydro-7H-pyrano [4',3':4,5]imidazo[1,2-b]pyridazin-6-ol (1.0 mg, 10% yield). LC/MS (M+1): 470.1; HPLC RT=1.18 min (analytical HPLC Method A). $^1$H NMR (500 MHz, DMSO-d$_6$) δ 9.00 (br. s, 2H), 8.39-8.22 (m, 1H), 7.94-7.81 (m, 1H), 7.55-6.98 (m, 6H), 6.36 (br. s., 1H), 4.88-4.69 (m, 1H), 4.11-3.96 (m, 2H), 1.49 (br. s, 6H).

Example 62

2-(4-(9-(2-(Difluoromethoxy)phenyl)-7,9-dihydro-6H-pyrano[4',3':4,5]imidazo[1,2-b]pyridazin-2-yl)phenyl)propan-2-ol

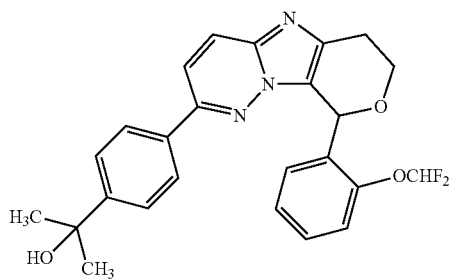

(62)

Intermediate 62A: Ethyl 2-(6-chloroimidazo[1,2-b]pyridazin-2-yl)acetate

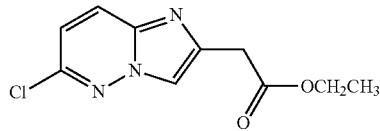

(62A)

A mixture of 6-chloropyridazin-3-amine (1.01 g, 7.80 mmol) and ethyl 4-bromo-3-oxobutanoate (2.12 g, 10.1 mmol) in ethanol (10 mL) was heated to 80° C. for 4 h. The reaction mixture was cooled to room temperature, basified with 1.0 N aqueous sodium hydroxide (8 mL), diluted with ethyl acetate (100 mL), washed with water (10 mL), brine (10 mL), dried (magnesium sulfate), filtered and concentrated under reduced pressure. Silica gel chromatography, eluting with zero to 60% ethyl acetate in hexanes, gave the desired ethyl 2-(6-chloroimidazo[1,2-b]pyridazin-2-yl)acetate (805 mg, 43% yield). LC/MS (M+1): 240.0; HPLC retention time: 0.69 min (analytical HPLC Method C); $^2$H NMR (400 MHz, CD$_3$OD) δ 8.10 (d, J=0.6 Hz, 1H), 7.97 (dd, J=9.5, 0.6 Hz, 1H), 7.30 (d, J=9.4 Hz, 1H), 4.21 (q, J=7.1 Hz, 2H), 3.90 (s, 2H), 1.31-1.23 (m, 3H).

Intermediate 62B: 2-(6-Chloroimidazo[1,2-b]pyridazin-2-yl)ethanol

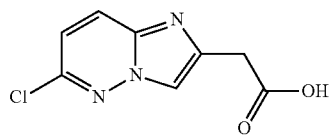

(62B)

Sodium borohydride (339 mg, 8.97 mmol) was added to a mixture of ethyl 2-(6-chloroimidazo[1,2-b]pyridazin-2-yl)acetate (430 mg, 1.794 mmol) in ethanol (5 mL) at 0° C. After stirring at room temperature for 2 h, the mixture was quenched with saturated ammonium chloride (5 mL), diluted with ethyl acetate (100 mL), washed with water (10 mL), brine (10 mL), dried (magnesium sulfate), filtered and concentrated under reduced pressure. Silica gel chromatography, eluting with 0-10% methanol in dichloromethane, gave the desired 2-(6-chloroimidazo[1,2-b]pyridazin-2-yl)ethanol (130 mg, 37% yield). LC/MS (M+1): 198.1; HPLC retention time: 0.45 min (analytical HPLC Method C). NMR indicated that it contained ~30% impurity. The impure material was converted to the next step without further purification.

Intermediate 62C: 2-Chloro-9-(2-(difluoromethoxy)phenyl)-7,9-dihydro-6H-pyrano[4',3':4,5]imidazo[1,2-b]pyridazine

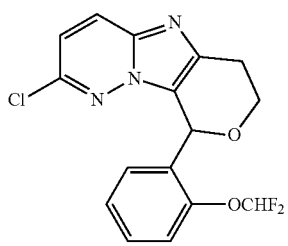

(62C)

A mixture of 2-(6-chloroimidazo[1,2-b]pyridazin-2-yl)ethanol (105 mg, 0.531 mmol), 2-(difluoromethoxy)benzaldehyde (137 mg, 0.797 mmol), pyridinium p-toluenesulfonate (1001 mg, 3.98 mmol) and sodium sulfate (377 mg, 2.66 mmol) in acetonitrile (2 mL) was heated at 80° C. in a sealed vial for 15 h. After cooling to room temperature, the reaction mixture was diluted with ethyl acetate (100 mL), washed with water (10 mL), brine (10 mL), dried (magnesium sulfate), filtered and concentrated under reduced pressure. Silica gel chromatography, eluting with 0-5% methanol in dichloromethane, gave the desired 2-chloro-9-(2-(difluoromethoxy)phenyl)-7,9-dihydro-6H-pyrano[4',3':4,5]imidazo[1,2-b]pyridazine (48 mg, 26% yield). LC/MS (M+1): 351.9; HPLC retention time: 0.83 min (analytical HPLC Method C). $^1$H NMR (400 MHz, CD$_3$OD) δ 7.99 (d, J=9.4 Hz, 1H), 7.43 (ddd, J=8.2, 7.4, 1.8 Hz, 1H), 7.35-7.11 (m, 3H), 7.13-6.60 (m, 2H), 6.42 (s, 1H), 4.22 (dt, J=11.6, 5.1 Hz, 1H), 4.04 (ddd, J=11.8, 7.4, 4.4 Hz, 1H), 3.18-3.07 (m, 1H), 3.05-2.91 (m, 1H).

Example 62

A mixture of 2-chloro-9-(2-(difluoromethoxy)phenyl)-7,9-dihydro-6H-pyrano [4',3':4,5]imidazo[1,2-b]pyridazine (10 mg, 0.028 mmol), (4-(2-hydroxypropan-2-yl) phenyl) boronic acid (6.14 mg, 0.034 mmol), PdCl$_2$(dppf)-CH$_2$Cl$_2$ adduct (4.64 mg, 5.69 μmol) and 2.0 M aqueous potassium phosphate (0.028 mL, 0.057 mmol) in N,N-dimethylformamide (0.8 mL) was degassed with nitrogen in a sealed vial and heated to 90° C. for 2 h. The mixture was cooled to room temperature and purified via preparative LC/MS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-100% B over 20 minutes, then a 5-minute hold at 100% B; Flow: 20 mL/min. Fractions containing the desired product were combined and dried via centrifugal evaporation to give 2-(4-(9-(2-(difluoromethoxy)phenyl)-7, 9-dihydro-6H-pyrano[4',3':4,5]imidazo[1,2-b]pyridazin-2-yl)phenyl)propan-2-ol (11.8 mg, 90% yield). LC/MS (M+1): 452.0; HPLC RT=1.60 min (analytical HPLC Method B). $^1$H NMR (500 MHz, DMSO-$d_6$) δ 8.11 (d, J=9.5 Hz, 1H), 7.71 (d, J=9.4 Hz, 1H), 7.62 (d, J=8.1 Hz, 2H), 7.55-7.41 (m, 3H), 7.41-7.22 (m, 2H), 7.22-7.06 (m, 2H), 6.40 (s, 1H), 4.18 (d, J=11.1 Hz, 1H), 4.00 (m, 1H), 3.11 (d, J=16.6 Hz, 1H), 3.01-2.81 (m, 1H), 1.42 (s, 6H).

Example 63

2-(5-(9-(2-(Difluoromethoxy)phenyl)-7,9-dihydro-6H-pyrano[4',3':4,5]imidazo[1,2-b]pyridazin-2-yl)pyrimidin-2-yl)propan-2-ol

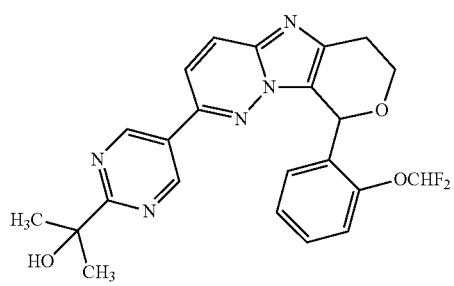

(63)

Following similar procedure as Step D of Example 11, 2-chloro-9-(2-(difluoromethoxy)phenyl)-7,9-dihydro-6H-pyrano[4',3':4,5]imidazo[1,2-b]pyridazine (12 mg, 0.034 mmol) was treated with 2-(5-(4,4,5,5-tetramethyl-1,3,2-dioxaborolan-2-yl)pyrimidin-2-yl)propan-2-ol (10.8 mg, 0.041 mmol) to provide 2-(5-(9-(2-(difluoromethoxy)phenyl)-7,9-dihydro-6H-pyrano[4',3':4,5]imidazo[1,2-b]pyridazin-2-yl)pyrimidin-2-yl)propan-2-ol (5.7 mg, 35% yield). LC/MS (M+1): 454.0; HPLC RT=1.17 min (analytical HPLC Method B). $^1$H NMR (500 MHz, DMSO-$d_6$) δ 9.00 (s, 2H), 8.28 (d, J=9.4 Hz, 1H), 7.90 (d, J=9.6 Hz, 1H), 7.57-7.41 (m, 1H), 7.37-6.96 (m, 4H), 6.41 (s, 1H), 4.18 (d, J=11.3 Hz, 1H), 4.01 (m., 1H), 3.18-3.03 (m, 1H), 2.96 (d, J=16.3 Hz, 1H), 1.46 (s, 6H).

Example 64

9-(2-(Difluoromethoxy)phenyl)-2-(1-methyl-1H-pyrazol-4-yl)-7,9-dihydro-6H-pyrano[4',3':4,5]imidazo[1,2-b]pyridazine

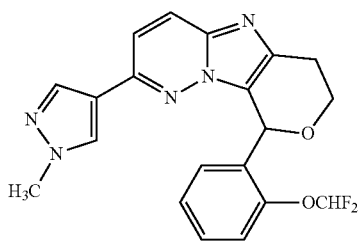

(64)

Following similar procedure as Step D of Example 11, 2-chloro-9-(2-(difluoromethoxy)phenyl)-7,9-dihydro-6H-pyrano[4',3':4,5]imidazo[1,2-b]pyridazine (12 mg, 0.034 mmol) was treated with 1-methyl-4-(4,4,5,5-tetramethyl-1,3,2-dioxaborolan-2-yl)-1H-pyrazole (8.52 mg, 0.041 mmol) to provide 9-(2-(difluoromethoxy)phenyl)-2-(1-methyl-1H-pyrazol-4-yl)-7,9-dihydro-6H-pyrano[4',3':4,5]imidazo[1,2-b]pyridazine (9.2 mg, 65% yield). LC/MS (M+1): 398.0; HPLC RT=1.08 min (analytical HPLC Method B). $^1$H NMR (500 MHz, DMSO-$d_6$) δ 8.13-7.96 (m, 2H), 7.61 (s, 1H), 7.49-7.39 (m, 2H), 7.34-7.24 (m, 2H), 7.20-7.02 (m, 2H), 6.35 (s, 1H), 4.15 (m, 1H), 3.97 (m, 1H), 3.48 (s, 3H), 3.09-3.01 (m, 1H), 2.88 (d, J=16.2 Hz, 1H).

Biological Assays

The pharmacological properties of the compounds of this invention may be confirmed by a number of biological assays. The exemplified biological assays, which follow, have been carried out with compounds of the invention.

TNF or CD40L-induced HEK-Blue Assay

Test compounds serially diluted in DMSO were plated in an assay plate (Labcyte, Cat. #LP-0200) at final concentrations ranging from 0.004 µM to 25µM. TNFα (final concentration 0.5 ng/ml) or CD40L (final concentration 30 ng/ml) in assay buffer [DMEM, 4.5 g/l glucose (Gibco, Cat. 21063-029), 10% FBS (Sigma, F4135), 1% Penicillin-Streptomycin (Gibco, Cat. 15140-122), 1% Anti-Anti (Gibco, Cat. 15240-112) and 2 mM L-glutamine (Gibco, Cat. 25030-081)] was then added to the assay plate. After a 30 minute pre-incubation at 37° C. and 5% $CO_2$, HEK-Blue-CD40L cells (InvivoGen, Cat. Code hkb-cd40) containing a NF-κB-driven secreted alkaline phosphatase reporter gene were seeded into the assay plate at a density of 20,000 cells per well. This plate was then incubated for 18 h at 37° C. and 5% $CO_2$. Secreted alkaline phosphatase expression was measured using QUANTI-Blue (InvivoGen, Cat. Code rep-qb1) according to manufacturer's specifications and the assay plate was read on a PerkinElmer Envision at 620 nm.

Inhibition data for the test compound over a range of concentrations was plotted as percentage inhibition of the test compound (100%=maximum inhibition). $IC_{50}$ values were determined after correcting for background [(sample read−mean of low control)/(mean of high control−mean of low control)] where by the low control is DMSO without stimulation and high control is DMSO with stimulation. The $IC_{50}$ is defined as the concentration of test compound which produces 50% inhibition and was quantified using the 4 parameter logistic equation to fit the data.

Table 3 lists the $IC_{50}$ values measured in the TNF induced HEK-Blue assay for Examples 1 to 64 of this invention. The results in Table 3 are reported as: "A" represents an $IC_{50}$ value of less than 1 µM; "B" represents an $IC_{50}$ value in the range of 1 µM to less than 10 µM; and "C" represents an $IC_{50}$ value in the range of 10 µM to 25 µM. The compounds of the present invention, as exemplified by Examples 1 to 64 showed $IC_{50}$ values measured in the TNF induced HEK-Blue assay of 25 µM or less.

TABLE 3

| Ex. No. | TNF induced HEK-Blue assay $IC_{50}$ value |
|---|---|
| 1 | A |
| 2 | A |
| 3 | B |
| 4 | A |
| 5 | B |
| 6 | A |
| 7 | B |

TABLE 3-continued

| Ex. No. | TNF induced HEK-Blue assay IC$_{50}$ value |
|---|---|
| 8 | A |
| 9 | B |
| 10 | B |
| 11 | C |
| 12 | A |
| 13 | A |
| 14 | B |
| 15 | B |
| 16 | B |
| 17 | B |
| 18 | C |
| 19 | B |
| 20 | C |
| 21 | B |
| 22 | B |
| 23 | B |
| 24 | A |
| 25 | B |
| 26 | A |
| 27 | B |
| 28 | B |
| 29 | B |
| 30 | B |
| 31 | B |
| 32 | B |
| 33 | A |
| 34 | B |
| 35 | B |
| 36 | B |
| 37 | B |
| 38 | B |
| 39 | A |
| 40 | B |
| 41 | B |
| 42 | A |
| 43 | B |
| 44 | A |
| 45 | B |
| 46 | B |
| 47 | B |
| 48 | C |
| 49 | B |
| 50 | B |
| 51 | C |
| 52 | B |
| 53 | B |
| 54 | B |
| 55 | B |
| 56 | B |
| 57 | B |
| 58 | A |
| 59 | B |
| 60 | B |
| 61 | C |
| 62 | A |
| 63 | A |
| 64 | B |

The invention claimed is:

1. A compound of Formula (I)

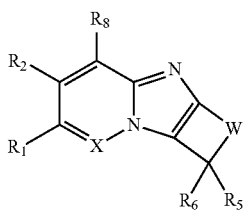

or a salt thereof, wherein:

X is N;

W is —CH$_2$CH$_2$—, —CH$_2$CH$_2$O—, —CH(OH)CH$_2$O—, —C(CH$_3$)(OH)CH$_2$O—, —C(OH)(pyridinyl)CH$_2$O—, —CH$_2$CH$_2$NH—, —CHFCH$_2$NH—, or —CH(OH)CH$_2$NH—;

R$_1$ is phenyl, pyridinyl, or pyrimidinyl, each substituted 1 to 2 substituents independently selected from Cl, —CH$_3$, —C(CH$_3$)$_2$OH, —C(CH$_2$CH$_3$)$_2$OH, —C(CH$_3$)(CH$_2$CH$_3$)OH, —CH(CH$_3$)OCH$_2$CH$_3$, —OCH$_3$, —OCH$_2$CH$_3$, —OCH$_2$CH$_2$CH$_3$, —OCH(CH$_3$)$_2$, —OCH$_2$C(CH$_3$)$_3$, —OCH$_2$CH(CH$_3$)$_2$, —OCH$_2$CH$_2$OCH$_3$, —OCH$_2$C(CH$_3$)$_2$OH, —OCH$_2$(methoxyphenyl), —S(O)$_2$CH$_3$, —S(O)$_2$NH$_2$, —S(O)$_2$NH(CH$_3$), —C(O)NH$_2$, —C(O)(morpholinyl), —C(O)(methoxyazetidinyl), —C(O)NH(cyclopropyl), hydroxycyclopropyl, morpholinyl, and carboxymethyl piperazinyl;

R$_2$ is H;

R$_5$ is phenyl substituted with 1 to 2 substituents independently selected from F, Cl, —CH$_3$, —CH$_2$CH$_3$, —CF$_3$, —OCH$_3$, —OCHF$_2$, and —OCF$_3$;

R$_6$ is H or —CH$_3$; and

R$_8$ is H.

2. The compound or a salt thereof, wherein said compound is:

(+/−)-9-(2-(difluoromethoxy)phenyl)-2-(6-methoxypyridin-3-yl)-6,7,8,9-tetrahydropyrido [4',3':4,5]imidazo[1,2-b]pyridazine (1); (+/−)-2-(4-(9-(2-(difluoromethoxy)phenyl)-6,7,8,9-tetrahydropyrido[4',3':4,5]imidazo[1,2-b]pyridazin-2-yl)phenyl)propan-2-ol (2); (+/−)-2-(5 (9-(2-(difluoromethoxy)phenyl)-6,7,8,9-tetrahydropyrido[4',3':4,5]imidazo[1,2]pyridazin-2-yl)pyrimidin-2-yl)propan-2-ol (3); (+/')-cis and trans-9-(2-(difluoromethoxy)phenyl)-2-(4-(2-hydroxypropan-2-yl)phenyl)-6,7,8,9-tetrahydropyrido[4',3':4,5]imidazo[1,2-b]pyridazin-6-ol (4 and 5); cis-(6R,9R)-9-(2-(difluoromethoxy)phenyl)-2-(4-(2-hydroxypropan-2-yl) phenyl)-6,7,8,9-tetrahydropyrido[4',3':4,5]imidazo[1,2-b]pyridazin-6-ol (6); cis-(6S,9S)-9-(2-(difluoromethoxy)phenyl)-2-(4-(2-hydroxypropan-2-yl)phenyl)-6,7,8,9-tetrahydropyrido [4',3':4,5]imidazo[1,2-b]pyridazin-6-ol (7); (+/−)-cis-2-(4-((6S,9S)-9-(2-(difluoromethoxy) phenyl)-6-fluoro-6,7,8,9-tetrahydropyrido[4',3':4,5]imidazo[1,2-b]pyridazin-2-yl)phenyl) propan-2-ol (8); (+/−)-trans-2-(4-(9-(2-(difluoromethoxy)phenyl)-6-fluoro-6,7,8,9-tetrahydropyrido[4',3':4,5]imidazo[1,2-b]pyridazin-2-yl)phenyl)propan-2-ol (9); (+/−)-cis-2-(5-(9-(2-(difluoromethoxy)phenyl)-6-fluoro-6,7,8,9-tetrahydropyrido[4',3':4,5]imidazo[1,2-b]pyridazin-2-yl)pyrimidin-2-yl)propan-2-ol (10); (+/−)-cis-9-(2-(difluoromethoxy)phenyl)-6-fluoro-2-(6-methoxypyridin-3-yl)-6,7,8,9-tetrahydropyrido[4',3':4,5]imidazo[1,2-b]pyridazine (11); cis-(1S,4S)-2-(4-(9-(2-(difluoromethoxy)phenyl)-6-fluoro-6,7,8,9-tetrahydropyrido[4',3':4,5]imidazo[1,2-b]pyridazin-2-yl)phenyl)propan-2-ol (12); cis-(1R,4R)-2-(4-(9-(2-(difluoromethoxy)phenyl)6-fluoro-6,7,8,9-tetrahydropyrido[',3':4,5]imidazo[1,2-b]pyridazin-2-yl)phenyl)propan-2-ol (13); trans-(6R,9S)-9-(2-(difluoromethoxy) phenyl)-2-(4-(2-hydroxypropan-2-yl)phenyl)-6,7,8,9-tetrahydropyrido[4',3':4,5]imidazo [1,2-b]pyridazin-6-ol (14); trans-(6S,9R)-9-(2-(difluoromethoxy)phenyl)-2-(4-(2-hydroxypropan-2-yl)phenyl)-6,7,8,9-tetrahydropyrido[4',3':4,5]imidazo [1,2-b]pyridazin-6-ol (15); cis-(6R,9S)-9-(2-

(difluoromethoxy)phenyl)-2-(6-methoxypyridin-3-yl)-6,7,8,9-tetrahydropyrido[4',3':4,5]imidazo[1,2-b]pyridazin-6-ol (16); 9-(2-(difluoromethoxy) phenyl)-2-(2-(2-hydroxypropan-2-yl)pyrimidin-5-yl)-6,7,8,9-tetrahydropyrido[4',3':4,5]imidazo[1,2-b]pyridazin-6-ol (17); (4-(9-(2-(difluoromethoxy)phenyl)-6-hydroxy-6,7,8,9-tetrahydropyrido[4',3 :4,5]imidazo[1,2-b]pyridazin-2-yl)phenyl)(3-methoxyazetidin-1-yl)methanone (18); (4-(9-(2-(difluoromethoxy)phenyl)-6-hydroxy-6,7,8,9-tetrahydropyrido [4',3':4,5]imidazo[1,2-b]pyridazin-2-yl)phenyl)(morpholino)methanone (19); N-cyclopropyl-4-(9-(2-(difluoromethoxy)phenyl)-6-hydroxy-6,7,8,9-tetrahydropyrido[4',3':4,5]imidazo[1,2-b]pyridazin-2-yl)benzamide (20); N-cyclopropyl-5-(9-(2-(difluoromethoxy) phenyl)-6-hydroxy-6,7,8,9-tetrahydropyrido[4',3':4,5]imidazo[1,2-b]pyridazin-2-yl) picolinamide (21); 2-(4-(5-(9-(2-(difluoromethoxy)phenyl)-6-hydroxy-6,7,8,9-tetrahydropyrido[4',3':4,5]imidazo[1,2-b]pyridazin-2-yl)pyrimidin-2-yl)piperazin-1-yl)acetic acid (22); (+/−)-trans-9-(4-fluoro-2-methoxyphenyl)-2-(4-(2-hydroxypropan-2-yl)phenyl)-6,7,8,9-tetrahydropyrido[4',3':4,5]imidazo[1,2-b]pyridazin-6-ol (23); (+/−)-trans-9-(2-ethylphenyl)-2-(4-(2-hydroxypropan-2-yl)phenyl)-6,7,8,9-tetrahydropyrido[4',3':4,5]imidazo[1,2-b]pyridazin-6-ol (24); (+/−)-cis-9-(2-ethylphenyl)-2-(4-(2-hydroxypropan-2-yl) phenyl)-6,7,8,9-tetrahydropyrido[4',3':4,5]imidazo[1,2-b]pyridazin-6-ol (25); 2-(4-(2-hydroxypropan-2-yl)phenyl)-9-(2-(trifluoromethoxy)phenyl)-6,7,8,9-tetrahydropyrido [4',3':4,5]imidazo[1,2-b]pyridazin-6-ol (26); (+/−)-cis-9-(2-(difluoromethoxy)phenyl)-2-(4-isobutoxyphenyl)-6,7,8,9-tetrahydropyrido[4',3':4,5]imidazo[1,2-b]pyridazin-6-ol (27); (+/−)-trans-9-(5-chloro-2-(difluoromethoxy)phenyl)-2-(4-(2-hydroxypropan-2-yl)phenyl)-6,7,8,9-tetrahydropyrido[4',3':4,5]imidazo[1,2-b]pyridazin-6-ol (28); (+/−)-cis-9-(2-(difluoromethoxy)phenyl)-2-(4-(2-hydroxy-2-methylpropoxy)phenyl)-6,7,8,9tetrahydropyrido[4',3':4,5]imidazo[1,2-b]pyridazin-6-ol (29); (+/−)-cis-9-(2-(difluoromethoxy)phenyl)-2-(4-(2-hydroxy-2-methylpropoxy)-3-methoxyphenyl)-6,7,8,9tetrahydropyrido[4',3':4,5]imidazo[1,2-b]pyridazin-6-ol (30); (+/−)-cis-9-(2-(difluoromethoxy)phenyl)-2-(4-ethoxyphenyl)-6,7,8,9-tetrahydropyrido[4',3':4,5] imidazo [1,2-b]pyridazin-6-ol (31); (+/−)-cis-9-(2-(difluoromethoxy)phenyl)-2-(4-isopropoxyphenyl)-6,7,8,9-tetrahydropyrido[4',3':4,5]imidazo[1,2-b]pyridazin-6-ol (32); (+/−)-cis-9-(2-(difluoromethoxy)phenyl)-2-(4-propoxyphenyl)-6,7,8,9-tetrahydropyrido [4',3':4,5]imidazo[1,2-b]pyridazin-6-ol (33); (+/−)-cis-9-(2-(difluoromethoxy)phenyl)-2-(4-(2-methoxyethoxy)phenyl)-6,7,8,9-tetrahydropyrido[4',3':4,5]imidazo[1,2-b]pyridazin-6-ol (34); (+/−)-cis-9-(2-(difluoromethoxy)phenyl)-2-(4-(1-ethoxyethyl)phenyl)-6,7,8,9-tetrahydropyrido[4',3':4,5]imidazo[1,2-b]pyridazin-6-ol (35); (+/−)-cis-9-(2-(difluoromethoxy)phenyl)-2-(4-(1-hydroxycyclopropyl)phenyl)-6,7,8,9-tetrahydropyrido [4',3':4,5]imidazo[1,2-b]pyridazin-6-ol (36); (+/−)-cis-9-(2-(difluoromethoxy)phenyl)-2-(4-((2-methoxybenzyl)oxy)phenyl)-6,7,8,9-tetrahydropyrido[4',3':4,5] imidazo[1,2-b]pyridazin-6-ol (37); (+/−)-trans-9-(4-fluoro-2-methoxyphenyl)-2-(4-(2-hydroxypropan-2-yl)phenyl)-6,7,8,9-tetrahydropyrido[4',3':4,5]imidazo[1,2-b]pyridazin-6-ol (38); (+/−)-cis-9-(4-fluoro-2-(trifluoromethyl)phenyl)-2-(4-(2-hydroxypropan-2-yl)phenyl)-6,7,8,9-tetrahydropyrido [4',3':4,5]imidazo[1,2-b]pyridazin-6-ol (39); (+/−)-cis-4-(9-(2-(difluoromethoxy)phenyl)-6-hydroxy-6,7,8,9-tetrahydropyrido[4',3':4,5]imidazo[1,2-b]pyridazin-2-yl)-N-methylbenzenesulfonamide (40); (+/−)-cis-9-(2-(difluoromethoxy)phenyl)-2-(4-(methylsulfonyl)phenyl)-6,7,8,9-tetrahydropyrido[4',3':4,5]imidazo[1,2-b]pyridazin-6-ol (41); (+/−)-cis-9-(2-(difluoromethoxy)phenyl)-2-(4-(neopentyloxy)phenyl)-6,7,8,9-tetrahydropyrido[4',3':4,5]imidazo[1,2-b]pyridazin-6-ol (42); (+/−)-cis-9-(4-fluoro-2-methylphenyl)-2-(4-(2-hydroxypropan-2-yl)phenyl)-6,7,8,9-tetrahydropyrido[4',3':4,5]imidazo[1,2-b]pyridazin-6-ol (43); (+/−)-trans-9-(4-fluoro-2-methylphenyl)-2-(4-(2-hydroxypropan-2-yl)phenyl)-6,7,8,9-tetrahydropyrido[4',3':4,5]imidazo[1,2-b]pyridazin-6-ol (44); (+/−)-cis-9-(2-(difluoromethoxy)phenyl)-2-(4-morpholinophenyl)-6,7,8,9-tetrahydropyrido[4',3':4,5]imidazo[1,2-b]pyridazin-6-ol (45); (+/−)-cis-4-(9-(2-(difluoromethoxy)phenyl)-6-hydroxy-6,7,8,9-tetrahydropyrido[4',3':4,5]imidazo[1,2-b]pyridazin-2-yl)benzenesulfonamide (46); (+/−)-cis-(2-chloro-4-(9-(2-(difluoromethoxy) phenyl)-6-hydroxy-6,7,8,9-tetrahydropyrido[4',3':4,5]imidazo[1,2-b]pyridazin-2-yl)phenyl)(morpholino)methanone (47); (+/−)-cis-2-chloro-4-(9-(2-(difluoromethoxy)phenyl)-6-hydroxy-6,7,8,9-tetrahydropyrido[4',3':4,5]imidazo[1,2-b]pyridazin-2-yl) benzamide (48); (+/−)-cis-9-(2-(difluoromethoxy)phenyl)-2-(4-(3-hydroxypentan-3-yl) phenyl)-6,7,8,9-tetrahydropyrido[4',3':4,5]imidazo[1,2-b]pyridazin-6-ol (49); (+/−) cis-9-(2-(difluoromethoxy)phenyl)-2-(4-(2-hydroxybutan-2-yl)phenyl)-6,7,8,9-tetrahydropyrido [4',3':4,5]imidazo[1,2-b]pyridazin-6-ol (50); (+/−)-trans-9-(2-(difluoromethoxy)phenyl)-2-(6-methoxypyridin-3-yl)-6,7,8,9-tetrahydropyrido[4',3':4,5]imidazo[1,2-b]pyridazin-6-ol (51); (+/−)trans-9-(2-(difluoromethoxy)phenyl)-2-(4-(2-hydroxy-2-methylpropoxy)phenyl)-6,7,8,9-tetrahydropyrido[4',3':4,5]imidazo[1,2-b]pyridazin-6-ol (52); (+/−)-trans-9-(2,5-dimethylphenyl)-2-(4-(2-hydroxypropan-2-yl)phenyl)-6,7,8,9-tetrahydropyrido[4',3':4,5]imidazo[1,2-b]pyridazin-6-ol (53); (+/−)-cis-9-(5-chloro-2-(difluoromethoxy)phenyl)-2-(4-(2-hydroxypropan-2-yl)phenyl)-6,7,8,9-tetrahydropyrido[4',3':4,5]imidazo [1,2-b]pyridazin-6-ol (54); (+/−)trans-9-(5-chloro-2-(trifluoromethyl)phenyl)-2-(4-(2-hydroxypropan-2-yl)phenyl)-6,7,8,9-tetrahydropyrido[4',3':4,5]imidazo[1,2-b]pyridazin-6-ol (55); (+/−)trans-9-(5-chloro-2-methoxyphenyl)-2-(4-(2-hydroxypropan-2-yl)phenyl)-6,7,8,9-tetrahydropyrido [4',3':4,5]imidazo[1,2-b]pyridazin-6-ol (56); rac-(6S,9S)-9-(2-(difluoromethoxy)phenyl)-2-(4-(2-hydroxypropan-2-yl)phenyl)-7,9-dihydro-6H-pyrano[4',3':4,5]imidazo[1,2-b]pyridazin-6-ol (57); cis-9-(2-(difluoromethoxy)phenyl)-2-(4-(2-hydroxypropan-2-yl)phenyl)-6,9-dihydro-7H-pyrano[4',3':4,5]imidazo[1,2-b]pyridazin-6-ol (58); 9-(2(difluoromethoxy) phenyl)-2-(4-(2-hydroxypropan-2-yl)phenyl)-6-methyl-6,9-dihydro-7H-pyrano[4',3':4,5] imidazo[1,2-b]pyridazin-6-ol (59); 9-(2-(difluoromethoxy)phenyl)-2-(4-(2-hydroxypropan-2-yl)phenyl)-6-(pyridin-4-yl)-6,9-dihydro-7H-pyrano[4',3':4,5]imidazo[1,2-b]pyridazin-6-ol (60); cis-9-(2-(difluoromethoxy)phenyl)-2-(2-(2-hydroxypropan-2-yl)pyrimidin-5-yl)-6,9-dihydro-7H-pyrano [4',3':4,5]imidazo[1,2-b]pyridazin-6-ol (61); cis-9-(2-(difluoromethoxy) phenyl)-2-(2-(2-hydroxypropan-2- yl)pyrimidin-5-yl)-6,9-dihydro-7H-pyrano[4',3':4,5]imidazo[1,2-b]pyridazin-6-ol (61); 2-(4-(9-(2-(difluoromethoxy)phenyl)-7,9-dihydro-6H-pyrano[4',3':4,5]imidazo[1,2-b]pyridazin-2-yl)phenyl)propan-2-ol (62); 2-(5-(9-(2-(difluoromethoxy)phenyl)-7,9-dihydro-6H-pyrano[4',3':4,5]imidazo[1,2-b]pyridazin-2-yl)pyrimidin-2-yl)propan-2-ol (63); or 9-(2-(difluoromethoxy)phenyl)-2-(1-methyl-1H-pyrazol-4yl)-7,9-dihydro-6H-pyrano[4',3':4,5]imidazo[1,2-b]pyridazine (64).

3. A pharmaceutical composition comprising one or more compounds according to claim 1 or a salt thereof; and a pharmaceutically acceptable carrier or diluent.

* * * * *

UNITED STATES PATENT AND TRADEMARK OFFICE
CERTIFICATE OF CORRECTION

PATENT NO. : 10,308,652 B2
APPLICATION NO. : 15/558708
DATED : June 4, 2019
INVENTOR(S) : Stephen T. Wrobleski et al.

It is certified that error appears in the above-identified patent and that said Letters Patent is hereby corrected as shown below:

On the Title Page

Column 2, (Other Publications) Line 14, delete "[3,4-a]" and insert -- [3,4-α] --, therefor.

In the Specification

Column 1, Line 8, Delete "371of" and insert -- 371 of --, therefor.

In the Claims

Claim 2, Column 82, Line 34, delete "(+/')" and insert -- (+/-) --, therefor.

Claim 2, Column 82, Line 59, delete "6-fluoro" and insert -- -6-fluoro --, therefor.

Claim 2, Column 82, Line 60, delete "[',3':4,5]" and insert -- [4',3':4,5] --, therefor.

Claim 2, Column 83, Line 7, delete "[4',3 :4,5]" and insert -- [4',3':4,5] --, therefor.

Claim 2, Column 83, Line 39, delete "9tetrahydropyrido" and insert -- 9-tetrahydropyrido --, therefor.

Claim 2, Column 83, Line 43, delete "9tetrahydropyrido" and insert -- 9-tetrahydropyrido --, therefor.

Claim 2, Column 83, Line 44, delete "2(difluoromethoxy)" and insert -- 2-(difluoromethoxy) --, therefor.

Claim 2, Column 84, Line 31, delete "(+/-) cis" and insert -- (+/-)-cis --, therefor.

Claim 2, Column 84, Line 37, delete "(+/-)trans" and insert -- (+/-)-trans --, therefor.

Claim 2, Column 84, Line 46, delete "(+/-)trans" and insert -- (+/-)-trans --, therefor.

Signed and Sealed this
Twenty-fourth Day of September, 2019

Andrei Iancu
*Director of the United States Patent and Trademark Office*

Claim 2, Column 84, Line 49, delete "(+/-)trans" and insert -- (+/-)-trans --, therefor.

Claim 2, Column 84, Line 58, delete "2(difluoromethoxy)" and insert -- 2-(difluoromethoxy) --, therefor.

Claim 2, Column 85, Line 9, delete "4yl)" and insert -- 4-yl) --, therefor.